US008158415B2

(12) United States Patent
Jo et al.

(10) Patent No.: US 8,158,415 B2
(45) Date of Patent: Apr. 17, 2012

(54) COMBINED USE OF CELL PERMEABLE NANOG AND OCT4 FOR INCREASING SELF-RENEWAL AND SUPPRESSING DIFFERENTIATION OF STEM CELLS

(75) Inventors: Dae Woong Jo, Gwangju (KR); Jin Sook Kim, Gwangsan-gu (KR); Yun Kyung Park, Buyeo-gun (KR)

(73) Assignee: Procell Therapeutics Inc., Seoul (KR)

( * ) Notice: Subject to any disclaimer, the term of this patent is extended or adjusted under 35 U.S.C. 154(b) by 378 days.

(21) Appl. No.: 12/528,919

(22) PCT Filed: Feb. 27, 2008

(86) PCT No.: PCT/KR2008/001134
§ 371 (c)(1),
(2), (4) Date: Aug. 27, 2009

(87) PCT Pub. No.: WO2008/105630
PCT Pub. Date: Sep. 4, 2008

(65) Prior Publication Data
US 2010/0099144 A1 Apr. 22, 2010

Related U.S. Application Data

(60) Provisional application No. 60/891,824, filed on Feb. 27, 2007.

(51) Int. Cl.
*C12N 15/00* (2006.01)
*C07H 21/02* (2006.01)
*C07K 14/00* (2006.01)
(52) U.S. Cl. ......... 435/320.1; 514/1; 536/23.1; 530/350
(58) Field of Classification Search ...... 514/1; 530/350; 536/23.1; 435/320.1
See application file for complete search history.

(56) References Cited

U.S. PATENT DOCUMENTS
2007/0026520 A1 2/2007 Kelly

FOREIGN PATENT DOCUMENTS
JP 2005-110565 4/2005
WO 95/34295 12/1995
WO 2008 093982 8/2008

OTHER PUBLICATIONS

Yao-Zhong Lin, et al., "Inhibition of Nuclear Translocation of Transcription Factor NF-κB by a Synthetic Peptide Containing a Ce I Membrane-permeable Motif and Nuclear Localization Sequence*", The Journal of Biological Chemistry, vol. 270, No. 24, XP 002050723, Jun. 16, 1995, pp. 14255-14258.
Hyun-Jin Do, et al., "An intact homeobox domain is required for complete nuclear localization of human Nanog", BBRC, vol. 353, XP 5762475A, 2007, pp. 770-775.
"Homeobox Transcription Factor Nanog", OMIM, XP-002578516, Retrieved from the Internet : URL:http://www.ncbi.nlm.nih.gov/entrez/dispomim.cgi?id=607937> [retrieved on Apr. 20, 2010], 7 pages.
Pan, G. et al., "A negative feedback loop of transcription factors that controls stem cell pluripotency and self-renewal", The FASEB Journal, vol. 20, pp. 1730-1732, Aug. 2006.
Wang, H. et al., "Roadmap to embryo implantation: clues from mouse models", Nature Reviews Genetics, vol. 7, No. 3, pp. 185-199, Mar. 2006.
Yuan, H. et al., "Developmental-specific activity of the FGF-4 enhancer requires the synergistic action of Sox2 and Oct-3", Genes & Development, vol. 9, pp. 2635-2645, Aug. 13, 1995.
Nanog: A New Recruit to the Embryonic Stem Cell Orchestra, CELL, vol. 113, pp. 551-552, May 30, 2003.
Nichols, J. et al., "Formation of Pluripotent Stem Cells in the Mammalian Embryo Depends on the POU Transcription Factor Oct4", vol. 95, pp. 379-391, Oct. 30, 1998.
Pan, G. et al. "Nanog and transcriptional networks in embryonic stem cell pluripotency", Cell Research, vol. 17, pp. 42-49, Jan. 9, 2007.
Hart, A. H. et al., "Identification, Cloning and Expression Analysis of the Pluripotency Promoting Nanog Genes in Mouse and Human", Developmental Dynamics, vol. 230, pp. 187-198, Mar. 31, 2004.
Chambers, I et al., "Functional Expression Cloning of Nanog, a Pluripotency Sustaining Factor in Embryonic Stem Cells", vol. 113, pp. 643-655, May 30, 2003.
Boyer, L. A. et al.,"Core Transcriptional Regulatory Circuitry in Human Embryonic Stem Cells", CELL, vol. 122, pp. 947-956, Sep. 23, 2005.
Pan, G J. et al., "Stem cell pluripotency and transcription factor Oct4", Cell Research, vol. 12, No. 5-6, pp. 321-329, 2002, (with English abstract).
Mitsui, K. et al. "The Homeoprotein Nanog Is Required for Maintenance of Pluripotency in Mouse Epiblast and ES Cells", CELL, vol. 113, pp. 631-642, May 30, 2003.

*Primary Examiner* — Karen Carlson
(74) *Attorney, Agent, or Firm* — Oblon, Spivak, McClelland, Maier & Neustadt, L.L.P.

(57) ABSTRACT

The present invention discloses cell permeable Nanog and Oct4 recombinant proteins that comprise a kaposi fibroblast growth factor 4 (kFGF4)-derived macromolecule transduction domain (MTD). Also disclosed are polynucleotides encoding the cell permeable Nanog and Oct4 recombinant proteins, a method of increasing self-renewal and suppressing differentiation of stem cells by treating the cells in combination with the cell permeable Nanog and Oct4 recombinant proteins, and the combined use of the cell permeable Nanog and Oct4 recombinant proteins for increasing self-renewal and suppressing differentiation of stem cells.

33 Claims, 17 Drawing Sheets

[Fig. 1]
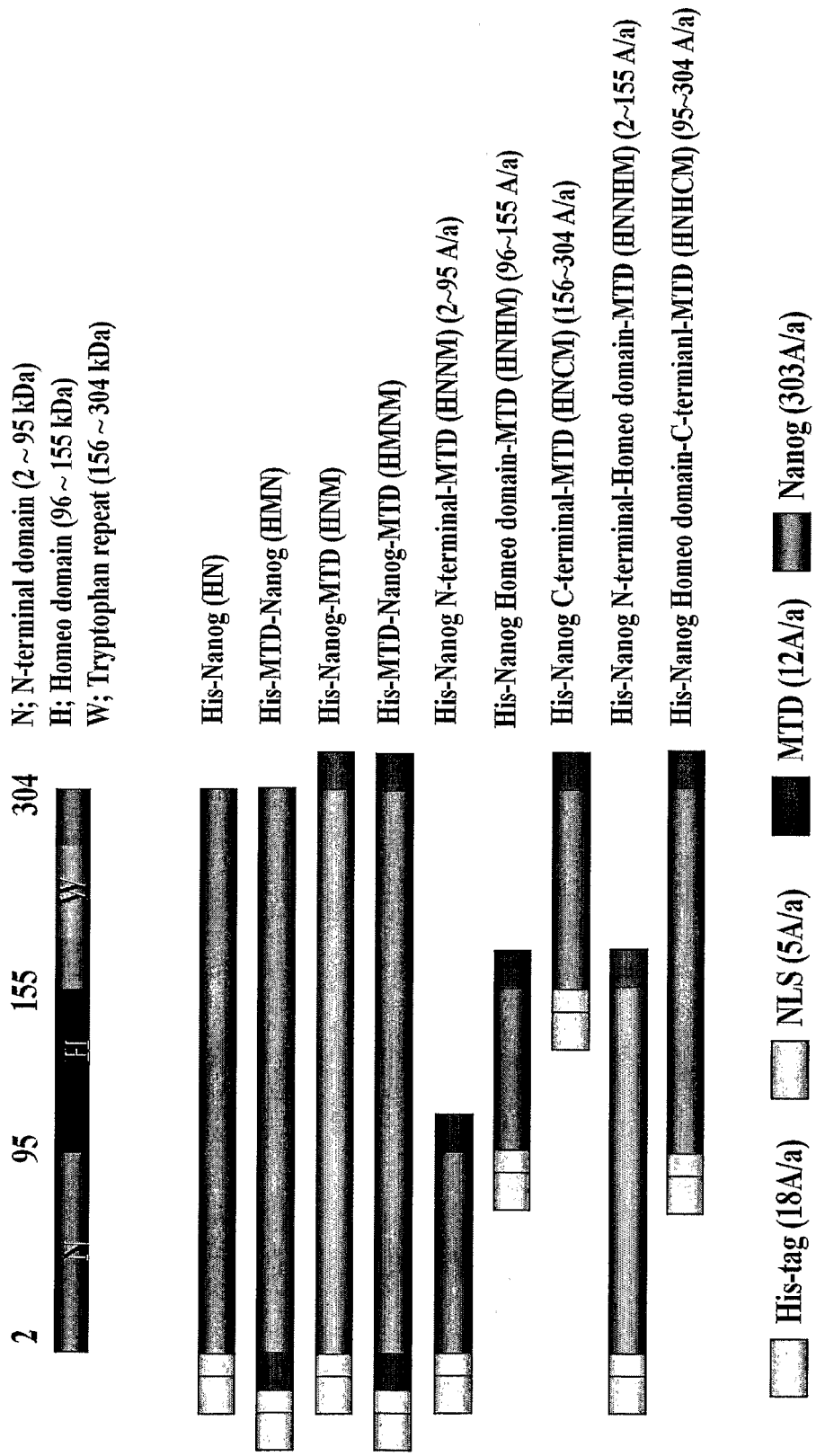

[Fig. 2]
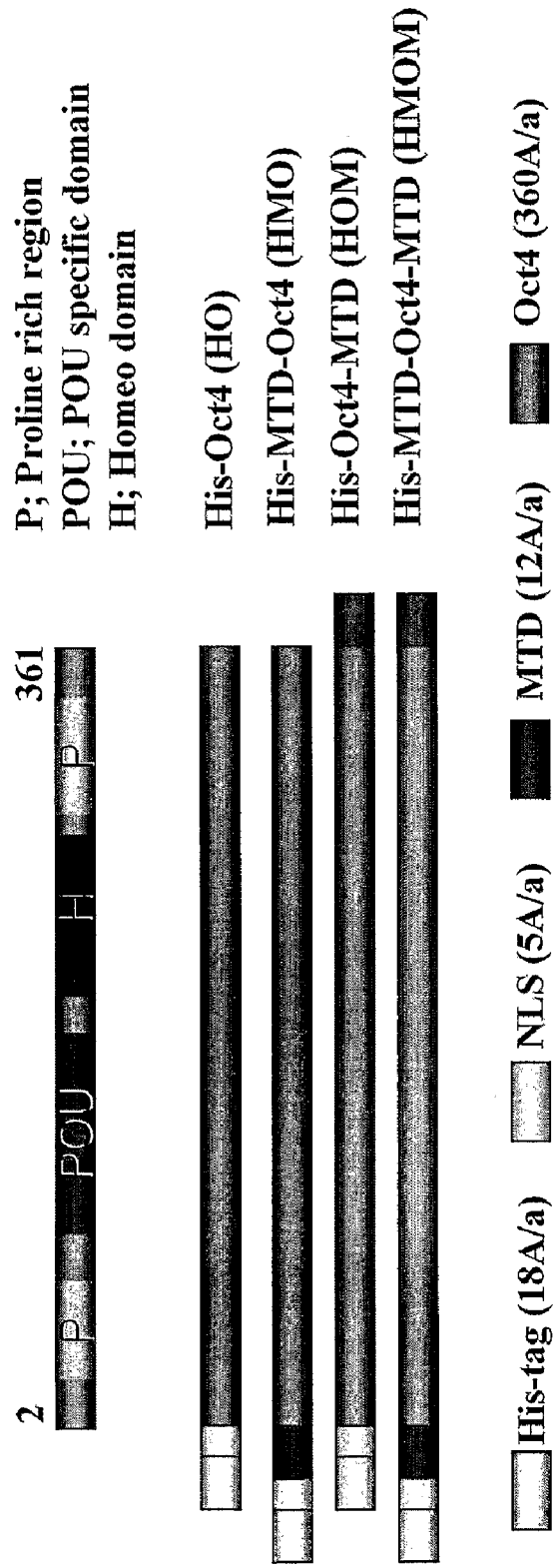

[Fig. 3]
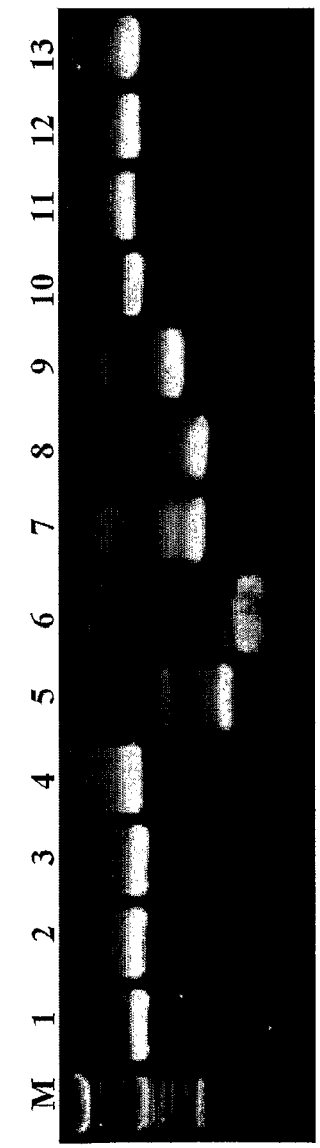
M; Marker
1; HN (969bp)
2; HMN (1005bp)
3; HNM (1005bp)
4; HMNM (1041bp)
5; HNNM (378bp)
6; HNHM (276bp)
7; HNCM (543bp)
8; HNNHM (558bp)
9; HNHCM (720bp)
10; HO (1140bp)
11; HMO (1176bp)
12; HOM (1176bp)
13; HMOM (1212bp)

[Fig. 4a]
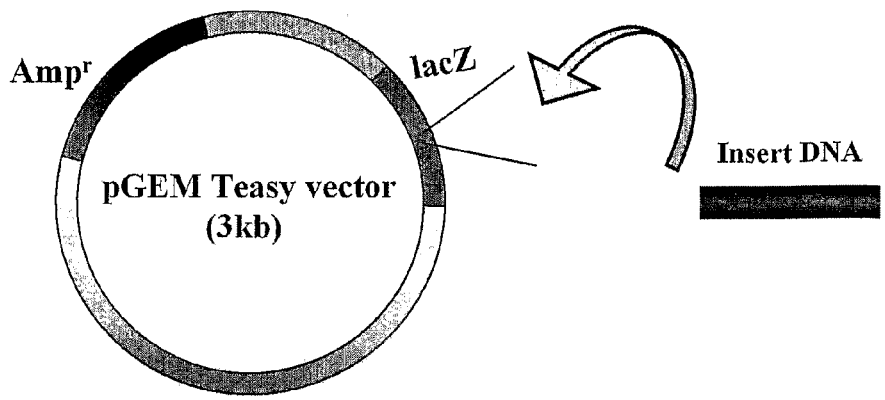
[Fig. 4b]
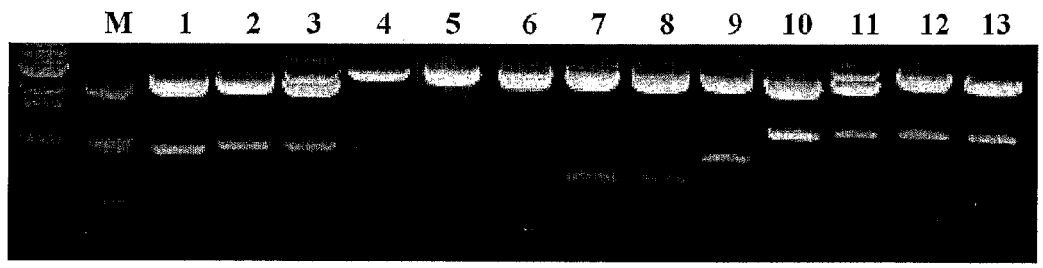
M; Marker
1; HN (969bp)
2; HMN (1005bp)
3; HNM (1005bp)
4; HMNM (1041bp)
5; HNNM (378bp)
6; HNHM (276bp)
7; HNCM (543bp)
8; HNNHM (558bp)
9; HNHCM (720bp)
10; HO (1140bp)
11; HMO (1176bp)
12; HOM (1176bp)
13; HMOM (1212bp)

[Fig. 5a]
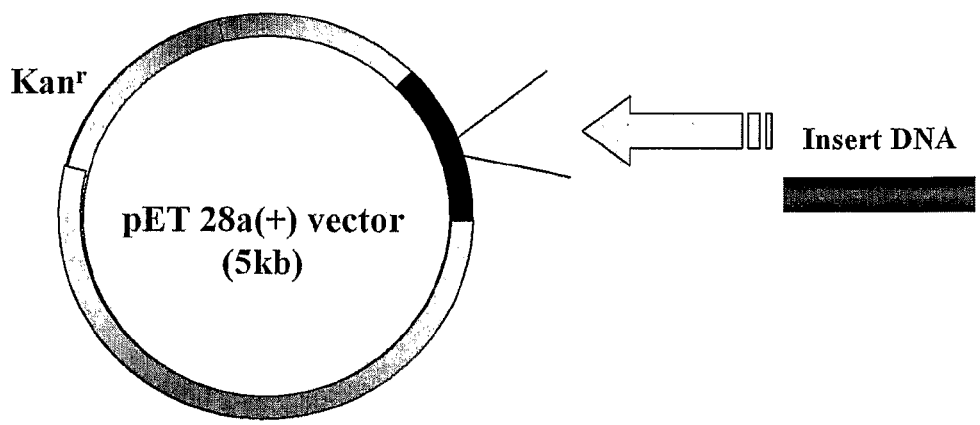
[Fig. 5b]
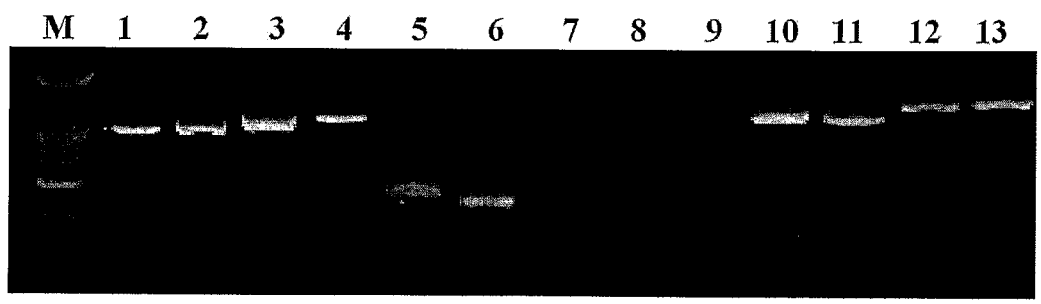
M; Marker
1; HN (969bp)
2; HMN (1005bp)
3; HNM (1005bp)
4; HMNM (1041bp)
5; HNNM (378bp)
6; HNHM (276bp)
7; HNCM (543bp)
8; HNNHM (558bp)
9; HNHCM (720bp)
10; HO (1140bp)
11; HMO (1176bp)
12; HOM (1176bp)
13; HMOM (1212bp)

[Fig. 6]
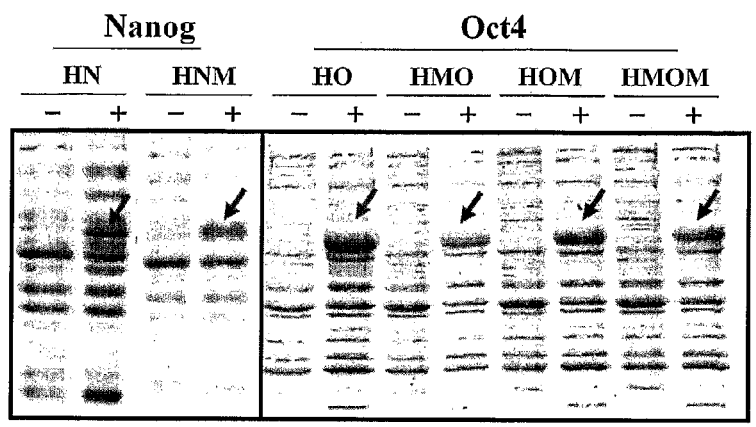
[Fig. 7]
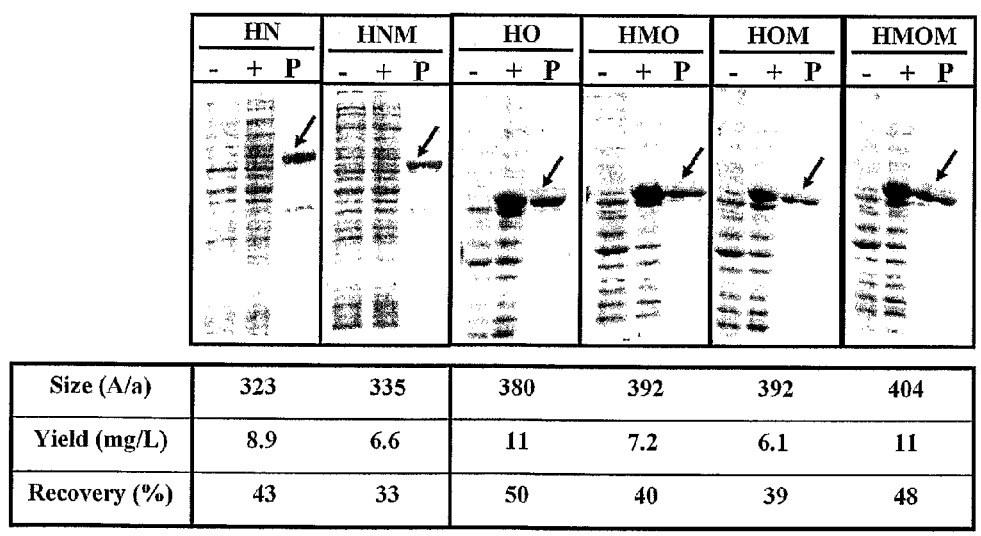

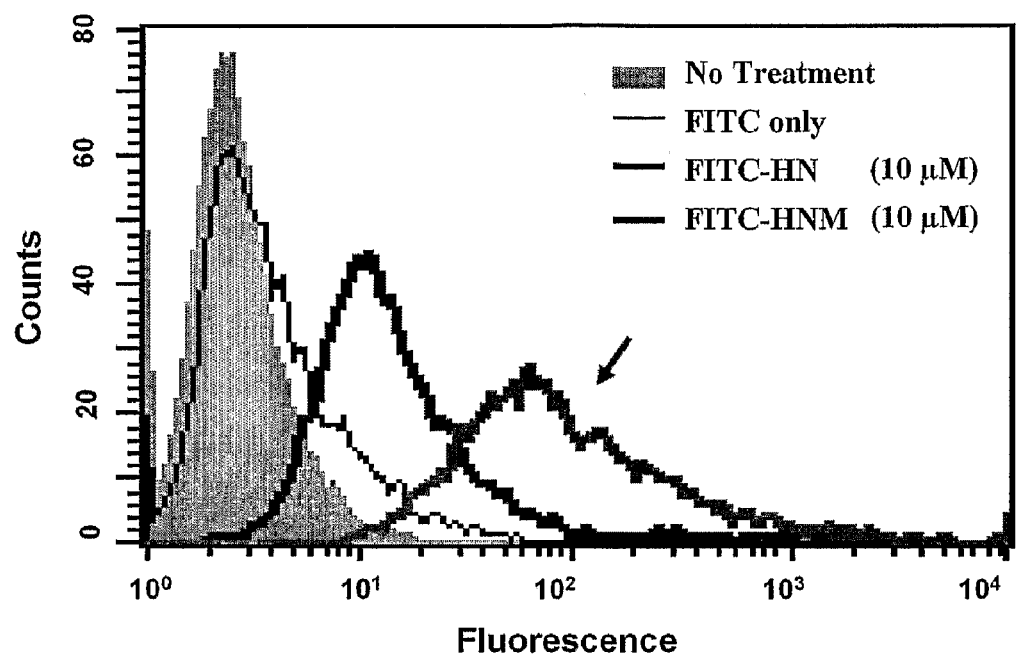
[Fig. 8]

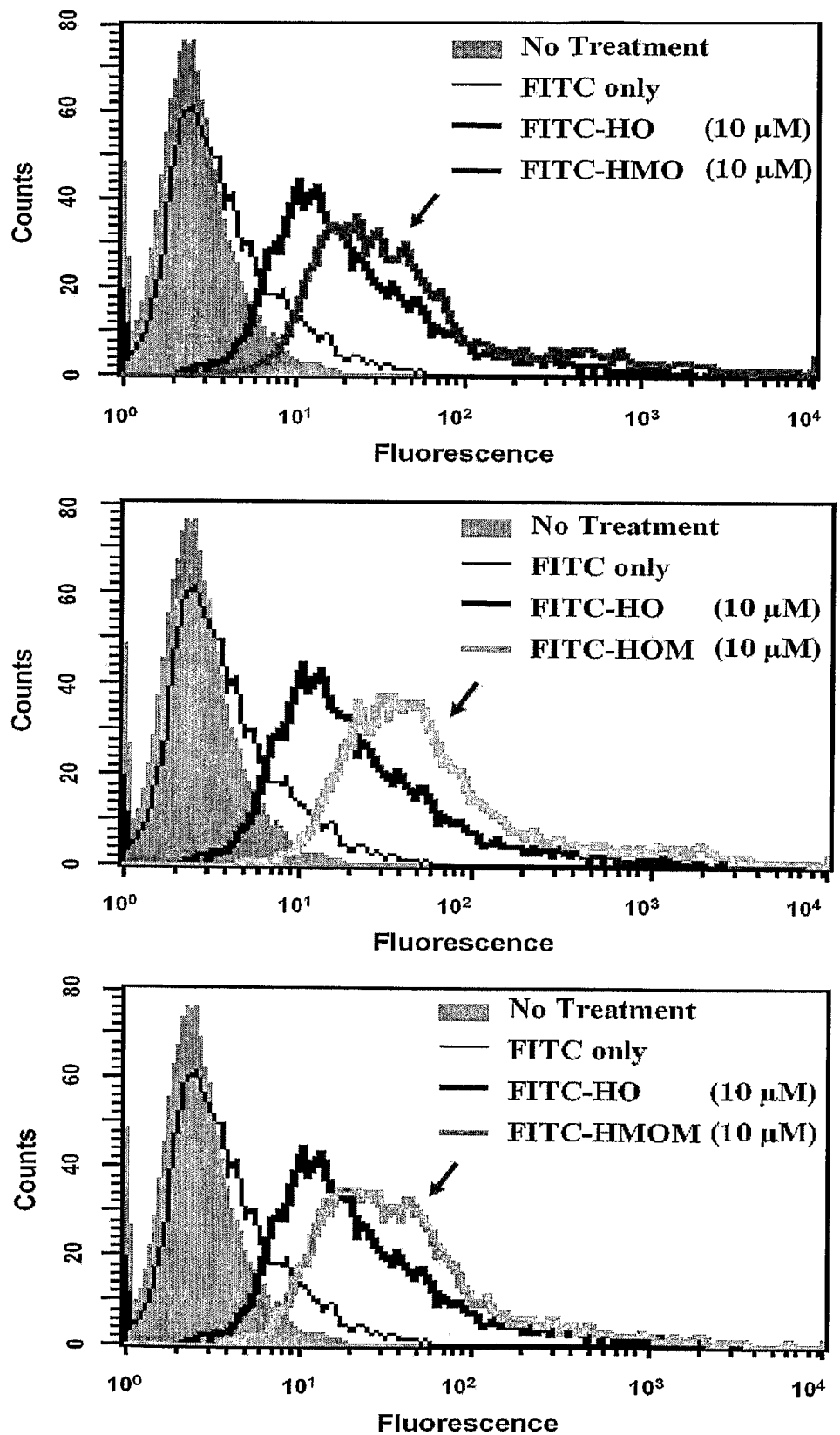
[Fig. 9]

[Fig. 10]
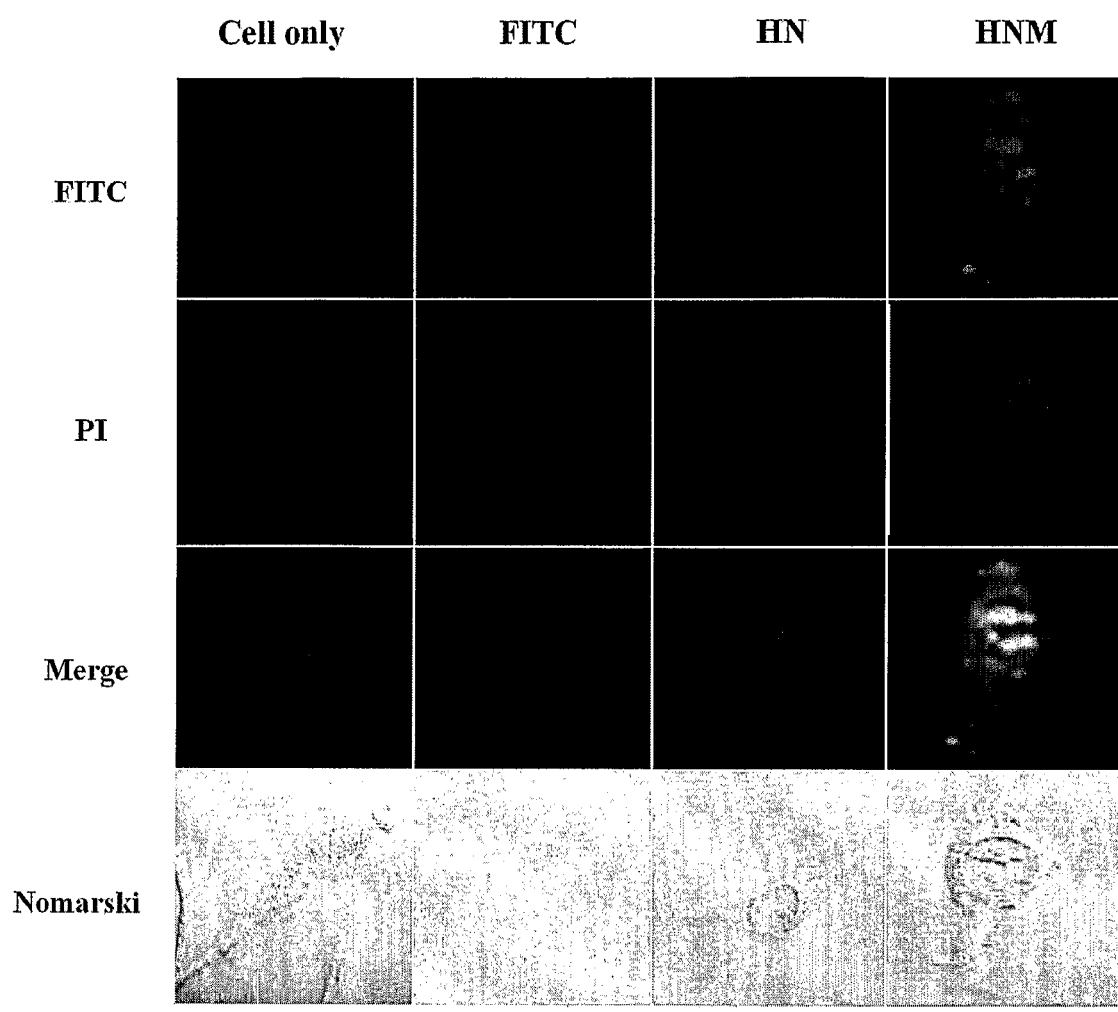

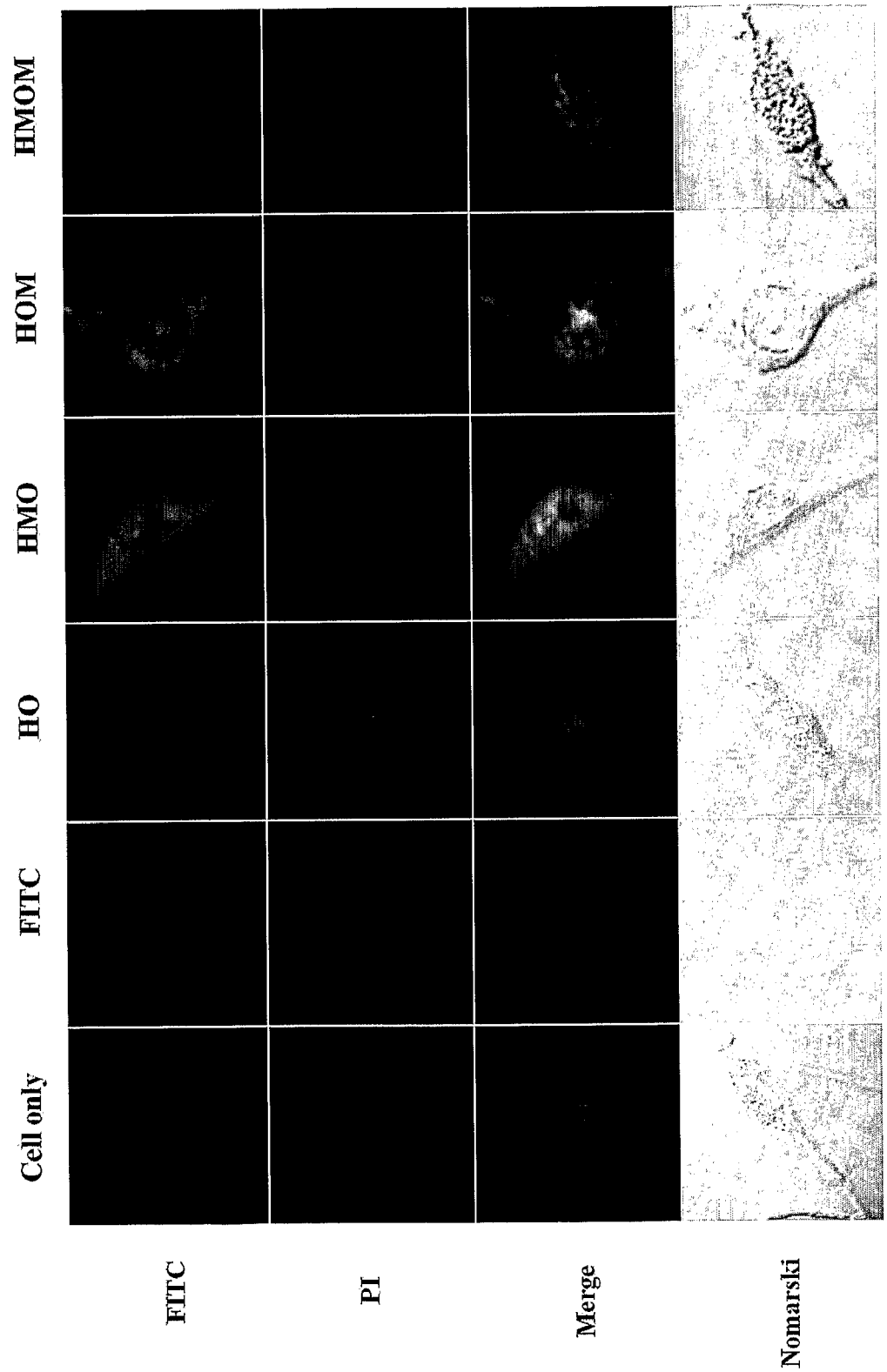
[Fig. 11]

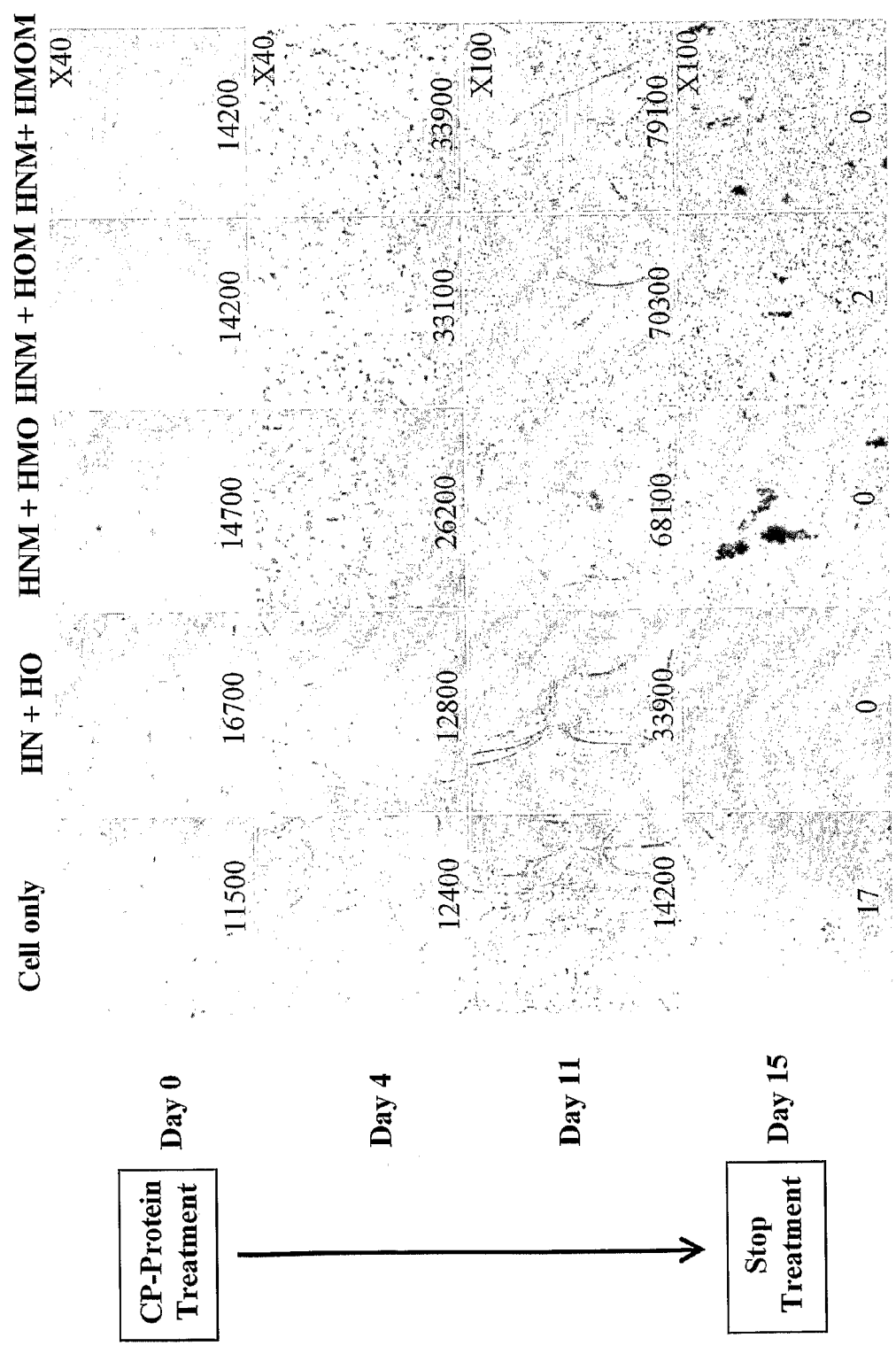
[Fig. 12]

[Fig. 13a]
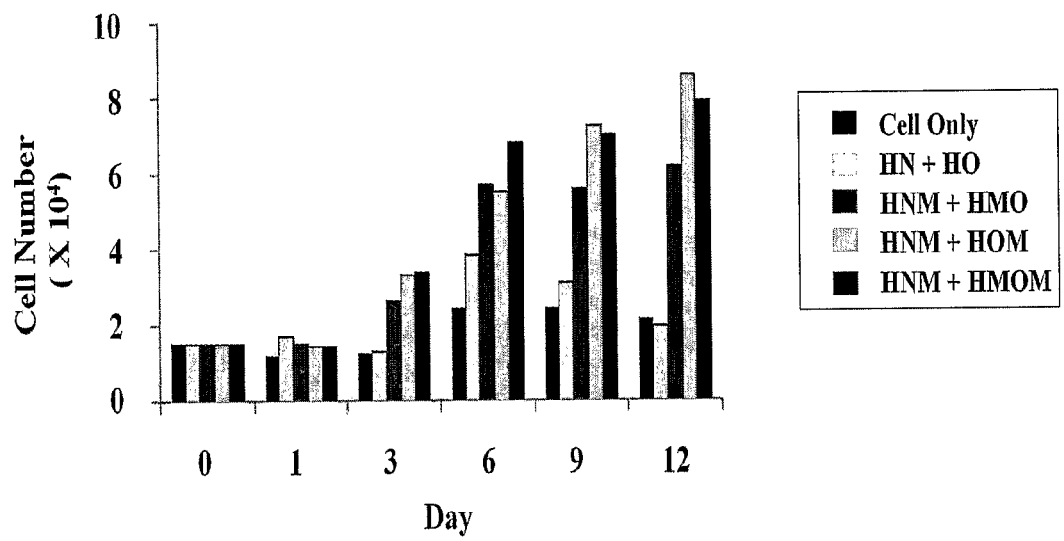
[Fig. 13b]
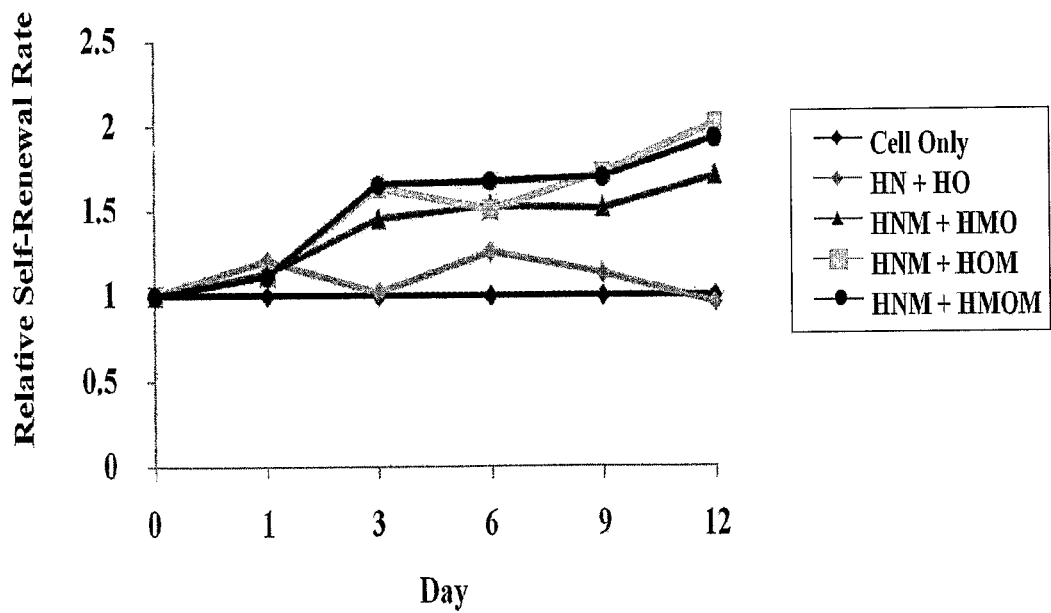

[Fig. 14]
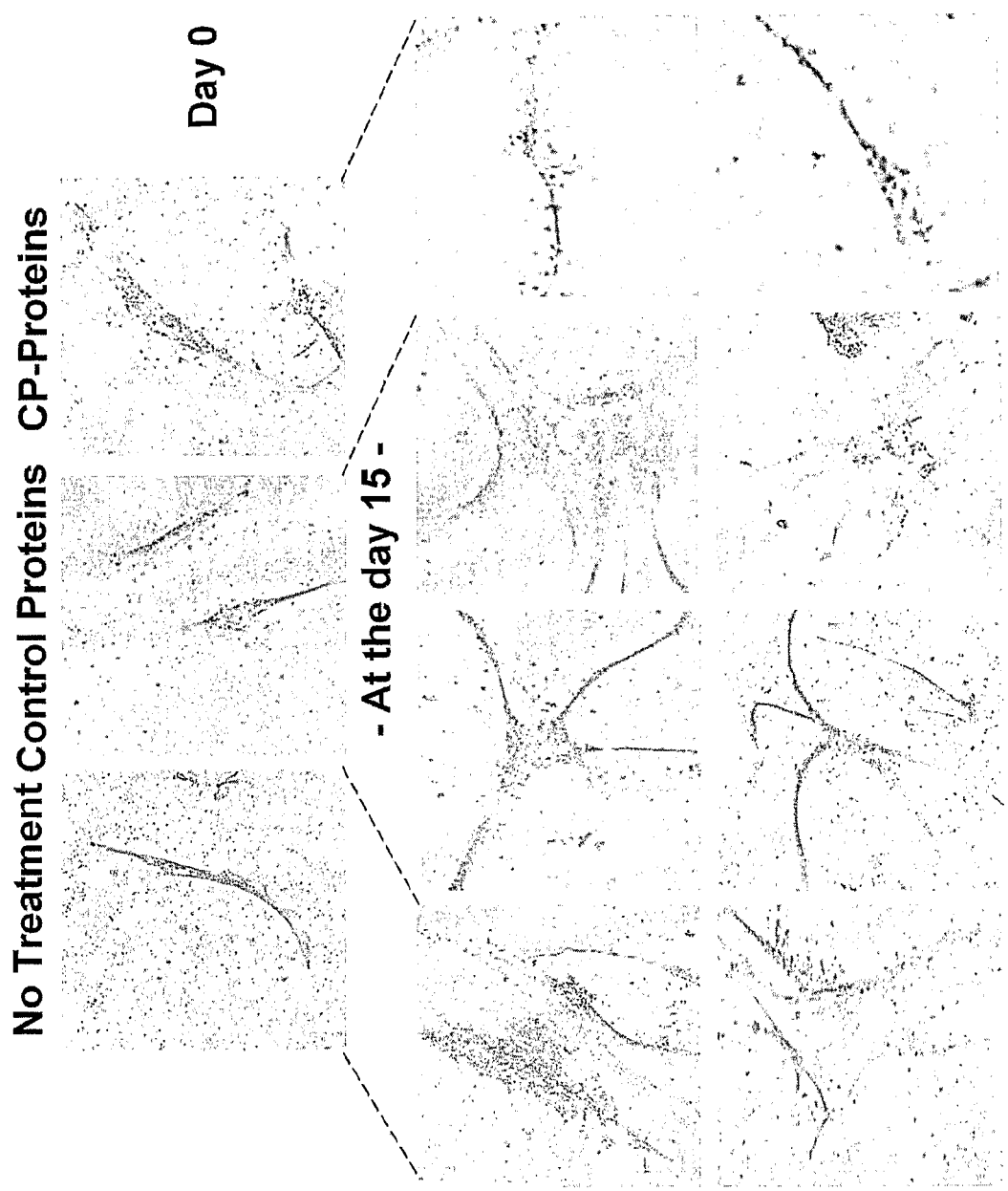

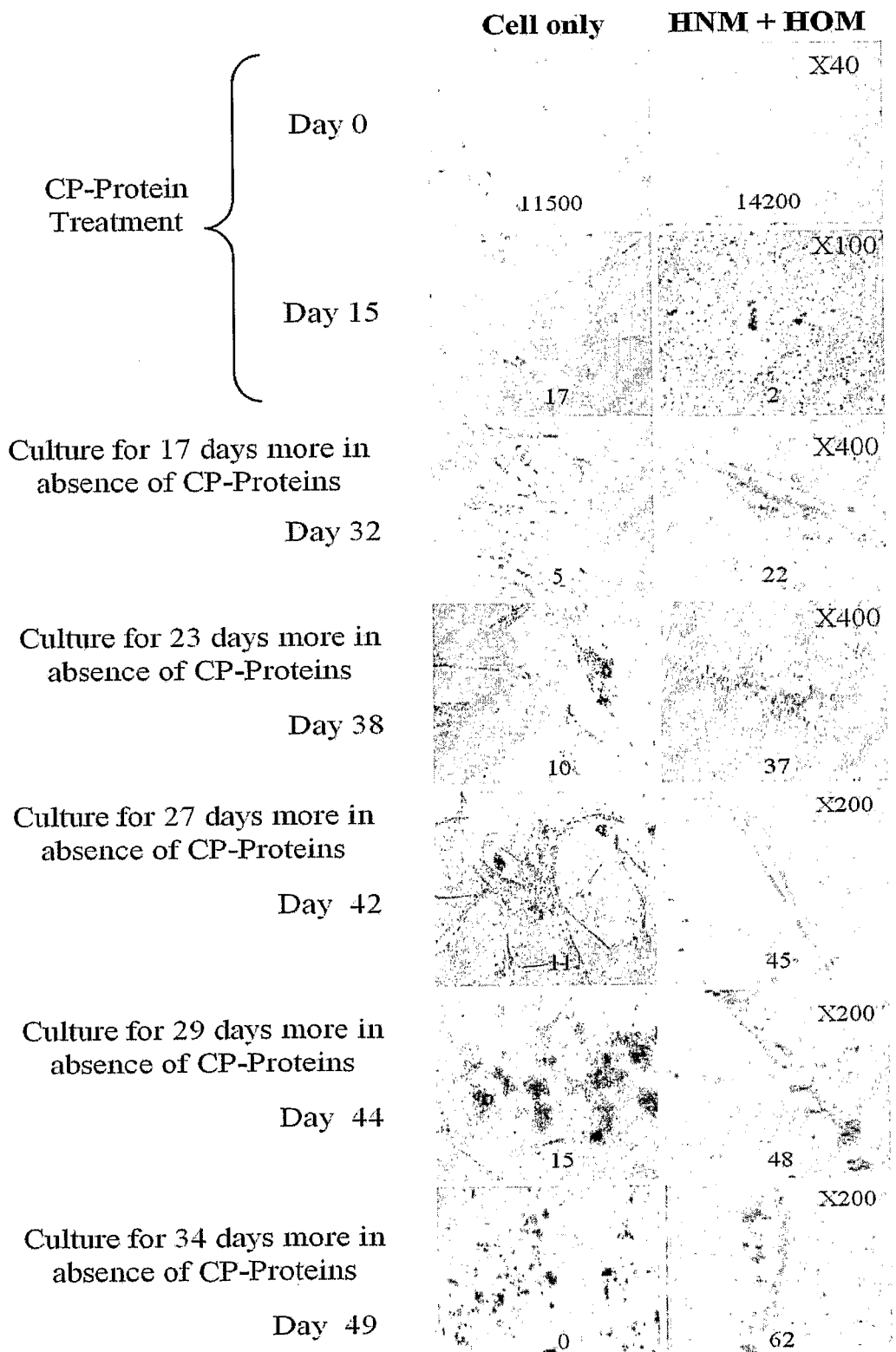
[Fig. 15a]

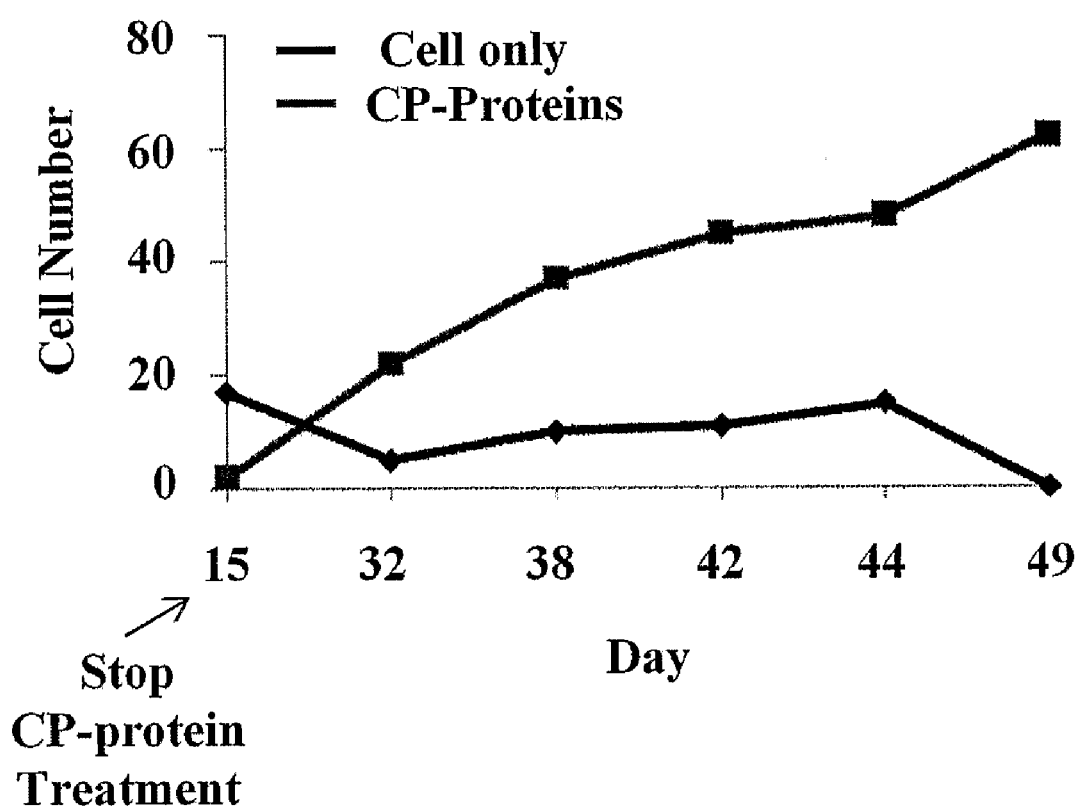
[Fig. 15b]

[Fig. 16]
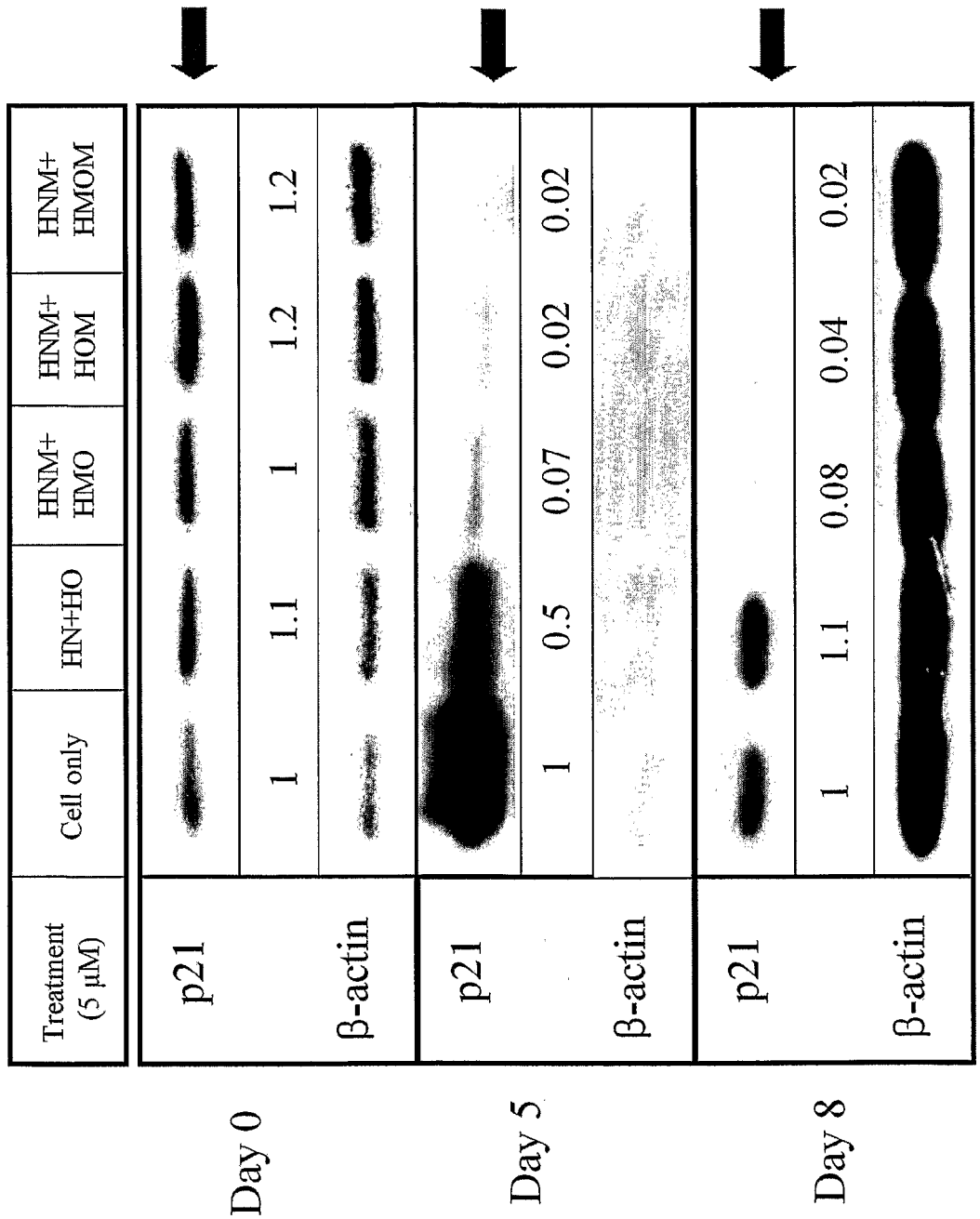

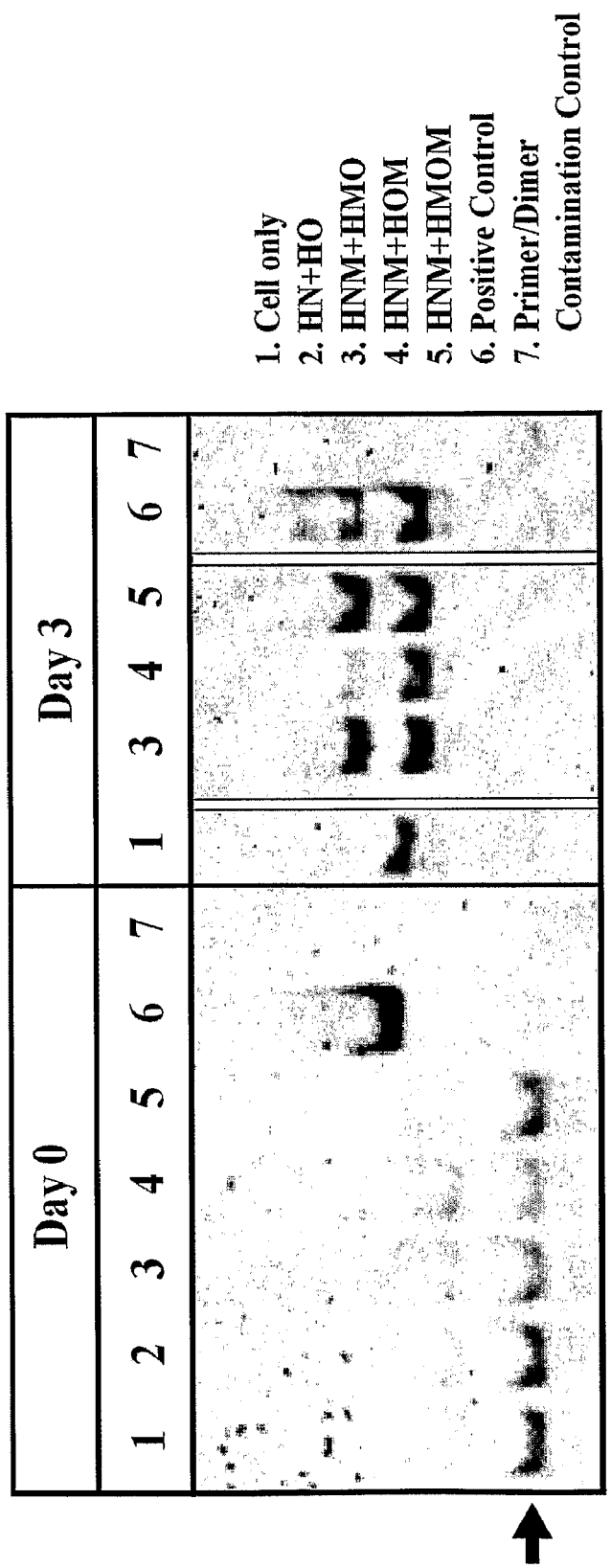
[Fig. 17]

COMBINED USE OF CELL PERMEABLE NANOG AND OCT4 FOR INCREASING SELF-RENEWAL AND SUPPRESSING DIFFERENTIATION OF STEM CELLS

CROSS-REFERENCE TO RELATED APPLICATIONS

The present application is a 35 U.S.C. §371 National Stage patent application of International patent application PCT/KR2008/001134, filed on Feb. 27, 2008, which claims priority to U.S. provisional patent application 60/891,824, filed on Feb. 27, 2007.

TECHNICAL FIELD

The present invention relates to the combined use of cell permeable Nanog (CP-Nanog) and cell permeable Oct4 (CP-Oct4) recombinant proteins for increasing self-renewal and suppressing the differentiation of stem cells.

BACKGROUND ART

Stem cells are cells found in all multicellular organisms. They retain the ability to renew themselves through mitotic cell division and can differentiate into a diverse range of specialized cell types. The classical definition of a stem cell requires that it possess two properties, self-renewal and potency. Self-renewal is defined as the ability to go through numerous cycles of cell division while maintaining an undifferentiated state, while potency is the capacity to differentiate into specialized cell types. In the strictest sense, this requires stem cells to be either totipotent or pluripotent, i.e., to be able to give rise to any mature cell type, although multipotent or unipotent progenitor cells are sometimes referred to as stem cells The two broad types of mammalian stem cells are embryonic stem cells, which are found in blastocysts, and adult stem cells, which are found in adult tissues.

Embryonic stem (ES) cells are cells derived from the epiblast tissue of the inner cell mass (ICM) of a blastocyst or earlier morula stage embryos. ES cells are pluripotent and give rise during development to all derivatives of the three primary germ layers, i.e., ectoderm, endoderm, and mesoderm. Thus, ES cells can develop into each of the more than 200 cell types of the adult body when given sufficient and necessary stimulation for a specific cell type.

A human embryonic stem cell is defined by the presence of several transcription factors and cell surface proteins. The transcription factors, Oct4, Nanog, and SOX2, form the core regulatory network that ensures the suppression of genes that lead to the differentiation and maintenance of pluripotency.

An adult stem cell is an undifferentiated cell found among differentiated cells in a tissue or organ. An adult stem cell can renew itself and can differentiate to yield the major specialized cell types of the tissue or organ. The primary role of adult stem cells in a living organism is to maintain and repair the tissue in which they are found. A great deal of adult stem cell research has focused on studying their capacity to divide or self-renew indefinitely and their differentiation potential. In mice, pluripotent stem cells are directly generated from adult fibroblast cultures.

While embryonic stem cell potential remains untested, adult stem cell treatments have been used for many years to successfully treat leukemia and related bone/blood cancers through bone marrow transplants. The use of adult stem cells in research and therapy is not as controversial as embryonic stem cells, because the production of adult stem cells does not require the destruction of an embryo.

Meanwhile, during mammalian embryo development, initial cellular differentiation becomes readily observable during compaction and blastocyst formation. At that time, the ES cells become committed to two distinct developmental pathways, i.e., the trophectoderm (TE), giving rise to extraembryonic tissues, and the inner cell mass (ICM), giving rise to the definitive germ layers of the embryo. This process of cellular differentiation is characterized by distinct alterations in gene and protein expression, including transcription factors involved in the determination of cell fate, cytokines involved in autocrine and paracrine signaling, and other structural and functional proteins involved in cell morphology and physiology.

An increasing number of transcription factors that are involved in the determination of cell fate at this key point in early embryonic development have been identified. Two of these transcription factors, Oct4 and Nanog, are thought to work in concert to maintain pluripotency and self-renewal in ICM and ES cells.

Oct4, a POU octamer-binding domain transcription factor, is known to be critical in mammalian embryonic development. Oct4 protein is expressed at the early blastocyst stage in both ICM and TE. However, expression is rapidly down-regulated in the TE and is generally limited to the ICM cells by the expanded blastocyst stage.

It has been demonstrated that Oct4 plays a pivotal role in establishing and maintaining cell lineage pluripotency, both in vivo and in vitro. The deletion of Oct4 causes early lethality in mouse at 3.5 days of gestation. A pluripotent ICM is not formed and the cells differentiate into a TE lineage. Conditional repression of Oct4 in mouse ES cells also resulted in differentiation into trophoblast lineage, while overexpression resulted in differentiation into primitive endoderm. These studies suggested that the level of Oct4 expression was a critical factor in the determination of cell lineage. It has also been proposed that Oct4 is necessary for the maintenance of ICM pluripotency and acts, in part, by repressing trophoblast lineages in the mouse.

The expression of a novel homeobox gene, Nanog, during early embryogenesis in the mouse has been reported. Nanog also plays a key role in self-renewal and the maintenance of pluripotency in mouse ICM and ES cells. Deletion of the gene for Nanog is an embryonic lethality and results in the loss of pluripotency in both ICM and ES cells. Nanog deficient ICM (Nanog -/-) and ES cells differentiate into extraembryonic endoderm. Nanog protein was detected as early as the morula stage. Strikingly, Nanog was strongly expressed in the inner apolar cells, but weakly or not expressed in the outer polar cells of the late morula. At the blastocyst stage, Nanog was only expressed in the ICM and was not expressed in the TE.

In sum, Oct4 and Nanog are essential factors for self-renewal and pluripotency of ICM and ES cells. Based on these facts, the present inventors have aimed to establish stem cells maintaining self-renewal potential and pluripotency in the undifferentiated state. As a result, the present inventors have developed a method of increasing self-renewal and suppressing differentiation of stem cells by treating them in combination with Nanog and Oct4, which are genetically engineered to have cell permeability.

DISCLOSURE

Technical Solution

The present invention relates to a cell permeable Nanog (CP-Nanog) recombinant protein comprising a macromolecule transduction domain (MTD) having cell permeability and a human transcription factor Nanog, said MTD being fused to N-terminus and/or C-terminus of the human Nanog protein.

Another aspect of the present invention relates to a cell permeable Oct4 (CP-Oct4) recombinant protein comprising a MTD having cell permeability and a human transcription factor Oct4, said MTD being fused to N-terminus and/or C-terminus of the human Oct4 protein.

The present invention also relates to isolated polynucleotides encoding each of the cell permeable Nanog and Oct4 recombinant proteins.

Another aspect of the present invention relates to an expression vector containing each of the isolated polynucleotide, and a transformant capable of producing each of the cell permeable Nanog and Oct4 recombinant proteins at high levels which is obtainable by transforming a host cell using the expression vector.

Still another aspect of the present invention relates to a method of producing the cell permeable Nanog and Oct4 recombinant proteins at high levels, respectively, which comprises the step of culturing the above transformant.

The present invention also relates to a combined use of the cell permeable Nanog and Oct4 recombinant proteins for increasing self-renewal and suppressing differentiation of stem cells.

Another aspect of the present invention relates to a method of increasing self-renewal and suppressing differentiation of stem cells which comprises the step of treating the stem cells in combination with the cell permeable Nanog and Oct4 recombinant proteins.

Still another aspect of the present invention relates to a method of establishing pluripotent stem cells maintaining self-renewal capacity and differentiation potential which comprises the step of treating the stem cells in combination with the cell permeable Nanog and Oct4 recombinant proteins.

Advantageous Effects

The cell permeable Nanog and Oct4 recombinant proteins of the present invention are capable of introducing Nanog and Oct4 into stem cells and, thus, can increase self-renewal and suppress differentiation of the stem cells. Therefore, the cell permeable Nanog and Oct4 recombinant proteins of the present invention can be effectively used in the establishment of a pluripotent stem cell line maintaining self-renewal capacity and differentiation potential which is useful for patient-specific or personally tailored stem cell therapy.

DESCRIPTION OF DRAWINGS

FIG. 1 is a schematic diagram illustrating the full-length and truncated forms of the cell permeable Nanog recombinant protein constructed according to the present invention.

FIG. 2 is a schematic diagram illustrating the full-length forms of the cell permeable Oct4 recombinant protein constructed according to the present invention.

FIG. 3 is a photograph of an agarose gel electrophoresis analysis showing DNA fragments encoding cell permeable Nanog and Oct4 recombinant proteins amplified by PCR according to the present invention.

FIG. 4a is a schematic diagram illustrating the subcloning of a DNA fragment encoding a cell permeable Nanog or Oct4 recombinant protein into the pGEM-Teasy vector according to the present invention.

FIG. 4b is a photograph of an agarose gel electrophoresis analysis showing DNA fragments encoding cell permeable Nanog and Oct4 recombinant proteins subcloned into pGEM-Teasy vector according to the present invention.

FIG. 5a is a schematic diagram illustrating the cloning of a DNA fragment encoding a cell permeable Nanog or Oct4 recombinant protein into the pET 28(+) vector according to the present invention.

FIG. 5b is a photograph of an agarose gel electrophoresis analysis showing DNA fragments encoding cell permeable Nanog and Oct4 recombinant proteins cloned into the pET 28(+) vector according to the present invention.

FIG. 6 is a photograph of a SDS-PAGE analysis illustrating the inducible expression of the cell permeable Nanog and Oct4 recombinant proteins according to the present invention.

FIG. 7 is a photograph of a SDS-PAGE analysis showing the purity of cell permeable Nanog and Oct4 recombinant proteins under denaturing conditions according to the present invention.

FIG. 8 is a graph illustrating the cell permeability of a cell permeable Nanog recombinant protein analyzed by flow cytometry according to the present invention.

FIG. 9 show graphs illustrating the cell permeabilities of cell permeable Oct4 recombinant proteins analyzed by flow cytometry according to the present invention.

FIG. 10 is a photograph visualizing the cell permeability of a cell permeable Nanog recombinant protein by confocal laser scanning microscopy according to the present invention.

FIG. 11 is a graph comparing the cell permeabilities of cell permeable Oct4 recombinant proteins according to the present invention, using a positive control.

FIG. 12 is a photograph visualizing the self-renewal and suppressive differentiation ability of human adult stem cells treated in combination with cell permeable Nanog and Oct4 recombinant proteins according to the present invention.

FIG. 13a is a graph illustrating the number of human adult stem cells treated in combination with the cell permeable Nanog and Oct4 recombinant proteins according to the present invention depending on the time course of the treatment.

FIG. 13b is a graph illustrating the self-renewal rate of human adult stem cells treated in combination with cell permeable Nanog and Oct4 recombinant proteins according to the present invention depending on the time course of the treatment.

FIG. 14 is a photograph visualizing the change in cell morphology of human adult stem cells treated in combination with cell permeable Nanog and Oct4 recombinant proteins according to the present invention depending on the time course of the treatment.

FIG. 15a is a photograph visualizing the self-renewal and suppressive differentiation ability of clonal adult stem cells selected after the combination treatment of cell permeable Nanog and Oct4 recombinant proteins is terminated.

FIG. 15b is a graph illustrating the number of clonal adult stem cells selected after the combination treatment of cell permeable Nanog and Oct4 recombinant proteins is terminated.

FIG. 16 is a photograph of a Western blot analysis illustrating the expression of p21 in adult stem cells treated in combination with cell permeable Nanog and Oct4 recombinant proteins according to the present invention depending on the time course of the treatment.

FIG. 17 is a photograph of a non-denaturing polyacrylamide gel electrophoresis analysis, illustrating an increase in telomerase activity of adult stem cells treated in combination with cell permeable Nanog and Oct4 recombinant proteins according to the present invention depending on the time course of the treatment.

DETAILED DESCRIPTION

The present invention is characterized by genetically engineering key transcription factors, Nanog and Oct4, which are essential for maintaining self-renewal and pluripotency of stem cells to have cell permeability, which is achieved by fusing a macromolecule transduction domain (MTD) having cell permeability to Nanog and Oct4, respectively.

In particular, the present invention provides a cell permeable Nanog (CP-Nanog) recombinant protein comprising a kaposi fibroblast growth factor 4 (kFGF4)-derived MTD and a transcription factor Nanog or a fragment thereof, said kFGF4-derived MTD being fused to the N-terminus, the C-terminus, or both of the transcription factor Nanog.

Another aspect of the present invention provides a cell permeable Oct4 (CP-Oct4) recombinant protein comprising a kFGF4-derived MTD and a transcription factor Oct4 or a fragment thereof, said kFGF4-derived MTD being fused to the N-terminus, the C-terminus, or both of the transcription factor Oct4.

As used herein, the term "macromolecule transduction domain (MTD)" refers to a peptide that facilitates the traverse of a biologically active molecule across the cell membrane.

The term "cell permeable recombinant protein" as used herein refers to a covalent binding complex bearing a macromolecule transduction domain (MTD) and a target biologically active molecule or a fragment thereof, where they are functionally linked by genetic fusion, chemical coupling non-covalent association or otherwise.

Nanog is a transcription factor critically involved in self-renewal of undifferentiated embryonic stem cells. Human Nanog protein (Accession Number NP_079141) is a 305 amino acid protein with a conserved homeodomain motif that is localized to the nuclear component of cells. The homeodomain facilitates DNA binding. There are an N-terminal domain, a homeodomain, and a C-terminal domain in human Nanog protein. Like murine Nanog, the N-terminal domain of human Nanog is rich in serine, threonine, and proline, while the C-terminal region contains tryptophan repeats.

Human Nanog protein has an amino acid sequence represented by SEQ ID NO: 2, and a polynucleotide encoding the same has a nucleotide sequence represented by SEQ ID NO: 1.

Oct4 is a homeodomain transcription factor of the POU family which is critically involved in the self-renewal of undifferentiated embryonic stem cells. Oct4 consists of the bipartite DNA-binding POU domain that is diagnostic of POU family members and has both N-terminal and C-terminal transactivation domains. The N-terminal domain is classified as a proline-rich transactivation domain, while the C-terminal domain is a serine/threonine-rich transactivation domain though it also has a high proline content.

Human Oct4 protein has an amino acid sequence represented by SEQ ID NO: 4, and a polynucleotide encoding the same has a nucleotide sequence represented by SEQ ID NO: 3.

The present invention employs a kaposi fibroblast growth factor 4 (kFGF4)-derived MTD as a macromolecular transduction domain capable of transporting the transcription factors Nanog and Oct4 through the cell membrane into a cell. The kFGF4-derived MTD of the present invention has an amino acid sequence represented by SEQ ID NO: 8, and a polynucleotide encoding the same has a nucleotide sequence represented by SEQ ID NO: 7.

First, the cell permeable Nanog recombinant protein of the present invention contains a kFGF4-derived MTD, a nuclear localization sequence (NLS; SEQ ID NO: 8) derived from SV40 large T antigen, a histidine-tag (His-Tag) for easy purification, and a transcription factor Nanog or a fragment thereof.

In a preferred embodiment of the present invention, the present invention constructs three full-length forms and five truncated forms of a cell permeable Nanog recombinant protein by using a kFGF4-derived MTD (see FIG. 1).

As used herein, the term "full-length form Nanog" refers to a construct including the entire N-terminal domain, a homeodomain, and a tryptophan repeat of the transcription factor Nanog, while the term "truncated form Nanog" refers to a construct lacking any one or more of the N-terminal domain, homeodomain, and C-terminal domain thereof.

Referring to FIG. 1, the full-length forms of a cell permeable Nanog recombinant protein are as follows:

1) His-MTD-Nanog (HMN), wherein a kFGF4-derived MTD is fused to the N-terminus of a full-length Nanog, 2) His-Nanog-MTD (HNM), wherein a kFGF4-derived MTD is fused to the C-terminus of a full-length Nanog, and 3) His-MTD-Nanog-MTD (HMNM), wherein a kFGF4-derived MTD is fused to both termini of a full-length Nanog, wherein a His-tag and a NLS derived from SV40 large T antigen are covalently coupled to the N-terminus of all constructs.

In the full-length forms of a cell permeable Nanog recombinant proteins as described above, His-MTD-Nanog (HMN) has an amino acid sequence represented by SEQ ID NO: 19 and a polynucleotide encoding the same has a nucleotide sequence represented by SEQ ID NO: 10; His-Nanog-MTD (HNM) has an amino acid sequence represented by SEQ ID NO: 20 and a polynucleotide encoding the same has a nucleotide sequence represented by SEQ ID NO: 11; His-MTD-Nanog-MTD (HMNM) has an amino acid sequence represented by SEQ ID NO: 21 and a polynucleotide encoding the same has a nucleotide sequence represented by SEQ ID NO: 12.

Further, the truncated forms of a cell permeable Nanog recombinant protein are as follows:

1) His-Nanog N-terminal-MTD (HNNM), wherein a kFGF4-derived MTD is fused to the C-terminus of a Nanog N-terminal domain fragment lacking a homeodomain and a tryptophan repeat, 2) His-Nanog homeodomain-MTD (HNHM), wherein a kFGF4-derived MTD is fused to the C-terminus of a Nanog homeodomain fragment lacking N-terminal and C-terminal domains, 3) His-Nanog C-terminal MTD (HNCM), wherein a kFGF4-derived MTD is fused to C-terminus of a Nanog C-terminal domain lacking an N-terminal domain and a homeodomain, 4) His-Nanog N-terminal-homeodomain-MTD (HNNHM), wherein a kFGF4-derived MTD is fused to the C-terminus of a Nanog N-terminal domain and homeodomain fragment lacking a C-terminal domain, and 5) His-Nanog homeodomain-C-terminal-MTD (HNHCM), wherein a kFGF4-derived MTD is fused to the C-terminus of a Nanog homeodomain and C-terminal domain fragment lacking an N-terminal domain, wherein a His-tag and a NLS derived from SV40 large T antigen are covalently coupled to the N-terminus of all constructs.

In the truncated forms of cell permeable Nanog recombinant proteins as described above, His-Nanog N-terminal-MTD (HNNM) has an amino acid sequence represented by SEQ ID NO: 22 and a polynucleotide encoding the same has a nucleotide sequence represented by SEQ ID NO: 13; His-Nanog homeodomain-MTD (HNHM) has an amino acid sequence represented by SEQ ID NO: 23 and a polynucleotide encoding the same has a nucleotide sequence represented by SEQ ID NO: 14; His-Nanog C-terminal MTD (HNCM) has an amino acid sequence represented by SEQ ID NO: 24 and a polynucleotide encoding the same has a nucleotide sequence represented by SEQ ID NO: 15; His-Nanog N-terminal-homeodomain-MTD (HNNHM) has an amino acid sequence represented by SEQ ID NO: 25 and a polynucleotide encoding the same has a nucleotide sequence represented by SEQ ID NO: 16; His-Nanog homeodomain-C-terminal-MTD (HNHCM) has an amino acid sequence represented by SEQ ID NO: 26 and a polynucleotide encoding the same has a nucleotide sequence represented by SEQ ID NO: 17.

As a control for the cell permeable Nanog recombinant proteins, His-Nanog (HN), wherein a full-length Nanog is fused only to a nuclear localization sequence (NLS) derived from SV40 large T antigen and a histidine-tag (His-Tag) without a kFGF4-derived MTD, is constructed. The control protein has an amino acid sequence represented by SEQ ID NO: 18 and a polynucleotide encoding the same has a nucleotide sequence represented by SEQ ID NO: 9.

Next, the cell permeable Oct4 recombinant protein of the present invention is composed of a kFGF4-derived MTD, a nuclear localization sequence (NLS) (SEQ ID NO: 8) derived from SV40 large T antigen, a histidine-tag (His-Tag) for easy purification, and a transcription factor Oct4.

In another preferred embodiment of the present invention, the present invention constructs three full-length forms of a cell permeable Oct4 recombinant protein by using a kFGF4-derived MTD (see FIG. 2).

As used herein, the term "full-length form Oct4" refers to a construct including the entire proline rich region, POU specific domain, and homeodomain of a transcription factor Oct4, while the term "truncated form Oct4" refers to a construct lacking any one or more of the proline rich region, POU specific domain, and homeodomain thereof.

Referring to FIG. 2, the full-length forms of a cell permeable Oct4 recombinant protein are as follows:

1) His-MTD-Oct4 (HMO), wherein a kFGF4-derived MTD is fused to the N-terminus of a full-length Oct4, 2) His-Oct4-MTD (HOM), wherein a kFGF4-derived MTD is fused to the C-terminus of a full-length Oct4, and 3) His-MTD-Oct4-MTD (HMOM), wherein a kFGF4-derived MTD is fused to both termini of a full-length Oct4, wherein a His-tag and a NLS derived from SV40 large T antigen are covalently coupled to the N-terminus of all constructs.

In the full-length forms of a cell permeable Nanog recombinant proteins as described above, His-MTD-Oct4 (HMO) has an amino acid sequence represented by SEQ ID NO: 32 and a polynucleotide encoding the same has a nucleotide sequence represented by SEQ ID NO: 28; His-Oct4-MTD (HOM) has an amino acid sequence represented by SEQ ID NO: 33 and a polynucleotide encoding the same has a nucleotide sequence represented by SEQ ID NO: 29; His-MTD-Oct4-MTD (HMOM) has an amino acid sequence represented by SEQ ID NO: 34 and a polynucleotide encoding the same has a nucleotide sequence represented by SEQ ID NO: 30.

As a control for the cell permeable Oct4 recombinant proteins, His-Nanog (HN), wherein a full-length Oct4 is fused only to a nuclear localization sequence (NLS) derived from SV40 large T antigen and a histidine-tag (His-Tag) without a kFGF4-derived MTD, is constructed. The control protein has an amino acid sequence represented by SEQ ID NO: 31 and a polynucleotide encoding the same has a nucleotide sequence represented by SEQ ID NO: 27.

Further, the present invention provides an expression vector containing the polynucleotide encoding one of the cell permeable Nanog and Oct4 recombinant proteins described above, and a transformant capable of producing each of the cell permeable Nanog and Oct4 recombinant proteins at high levels, which is obtainable by transforming a host cell using the expression vector.

As used herein, the term "expression vector" means a construct capable of in vivo or in vitro expression. Preferably, the expression vector is incorporated into the genome of a suitable host organism.

The term "incorporated" preferably covers stable incorporation into the genome.

The nucleotide sequence of the present invention may be present in a vector in which the nucleotide sequence is operably linked to regulatory sequences capable of providing for the expression of the nucleotide sequence by a suitable host organism. The vectors for use in the present invention may be transformed into a suitable host cell as described below to provide for expression of a polypeptide of the present invention.

The choice of vector e.g., a plasmid, cosmid, or phage vector will often depend on the host cell into which it is to be introduced. The vectors for use in the present invention may contain one or more selectable marker genes, such as a gene which confers antibiotic resistance, e.g., ampicillin, kanamycin, chloramphenicol, or tetracyclin resistance.

Vectors may be used in vitro, for example, for the production of RNA or used to transfect, transform, transduce or infect a host cell. Thus, in a further embodiment, the present invention provides a method of producing a polypeptide of the present invention by introducing a nucleotide sequence encoding the same into a replicable vector, introducing the vector into a compatible host cell, and growing the host cell under conditions which lead to the replication of the vector.

The vector may further comprise a nucleotide sequence enabling the vector to replicate in the host cell in question. Examples of such sequences include the origins of replication of plasmids pUC19, pACYC177, pUB110, pE194, pAMB1, and pIJ702.

In some applications, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e., the vector is an expression vector.

The term "operably linked" refers to a juxtaposition where the components described are in a relationship permitting them to function in their intended manner. A regulatory sequence "operably linked" to a coding sequence is ligated in such a way that expression of the coding sequence is achieved under conditions compatible with the control sequences.

The term "regulatory sequences" includes promoters, enhancers, and other expression regulation signals.

The term "promoter" is used in the normal sense of the art, e.g., an RNA polymerase binding site.

Enhanced expression of the nucleotide sequence encoding the cell permeable recombinant proteins of the present invention may also be achieved by the selection of heterologous regulatory regions, e.g. promoter, secretion leader and terminator regions. Preferably, the nucleotide sequence according to the present invention is operably linked to at least a promoter. Examples of suitable promoters for directing the transcription of the nucleotide sequence in a bacterial, fungal or yeast host are well known in the art.

In a preferred embodiment, the polynucleotide of the present invention is cloned into a pET-28a(+) vector (Novagen, USA) bearing a His-tag sequence so as to fuse six histidine residues (SEQ ID NO: 47) to the N-terminus of the cell permeable recombinant protein to allow a one-step purification.

Accordingly, the cell permeable recombinant protein expressed in the above expression vector has a structure where a kFGF4-derived MTD is fused to the full-length or truncated Nanog or Oct4, and a His-tag and NLS are linked to the N-terminus thereof.

Thus constructed expression vectors for expressing the cell permeable Nanog recombinant protein are designated pET28a(+)-HMN, pET28a(+)-HNM, pET28a(+)-HMNM, pET28a(+)-HNNM, pET28a(+)-HNHM, pET28a(+)-HNCM, and pET28a(+)-HNHCM, respectively. Further, the expression vectors for expressing the cell permeable Oct4 recombinant protein are designated pET28a(+)-HMO, pET28a(+)-HOM, and pET28a(+)-HMOM, respectively.

Among them, the expression vectors pET28a(+)-HNM containing His-Nanog-kFGF4-derived MTD construct; pET28a(+)-HMO containing His-kFGF4-derived MTD construct-Oct4; pET28a(+)-HOM containing His-Oct4-kFGF4-derived MTD construct; and pET28a(+)-HMOM containing His-kFGF4-derived MTD-Oct4-kFGF4-derived MTD construct were deposited under accession numbers KCTC 11278BP, KCTC 11279BP, KCTC 11280BP and KCTC 11281BP, respectively, with the Korean Collection for Type Cultures (KCTC), Korea Research Institute of Bioscience and Biotechnology (KRIBB), 52, Oun-Dong, Yusong-Ku, Taejon 305-333, Republic of Korea. All deposits referred to herein were made on Feb. 22, 2008 in accordance with the Budapest Treaty, and all restrictions imposed by the depositor on the availability to the public of the deposited biological material will be irrevocably removed upon the granting of the patent.

The present invention further provides a transformant capable of producing each of the CP-Nanog and CP-Oct4 recombinant proteins at high levels which is obtainable by transforming a host cell using the expression vector.

The term "host cell" in relation to the present invention includes any cell that comprises either the nucleotide sequence or an expression vector as described above and which is used in the production of a cell permeable recombinant protein having the specific properties as defined herein.

Thus, a further embodiment of the present invention provides host cells transformed or transfected with a nucleotide sequence that expresses the cell permeable recombinant proteins of the present invention. The cells will be chosen to be compatible with the vector and may be prokaryotic (e.g., bacterial), fungal, yeast, or plant cells. Preferably, the host cells are not human cells.

Examples of suitable bacterial host organisms are gram positive or gram negative bacterial species. Depending on the nature of the nucleotide sequence encoding the cell permeable recombinant proteins of the present invention and/or the desirability for further processing of the expressed protein, eukaryotic hosts, such as *E. coli*, may be preferred.

The use of suitable host cells, such as yeast, fungal, and plant host cells, may provide for post-translational modifications (e.g. myristoylation, glycosylation, truncation, lipidation, and tyrosine, serine, or threonine phosphorylation) as may be needed to confer optimal biological activity on recombinant expression products of the present invention.

The genotype of the host cell may be modified to improve expression. Examples of host cell modifications include protease deficiency, supplementation of rare tRNA, and modification of the reductive potential in the cytoplasm to enhance disulfide bond formation.

For example, the host cell *E. coli* may overexpress rare tRNA to improve expression of heterologous proteins as described in Kane (*Curr. Opin. Biotechnol.* 6:494-500 (1995)). The host cell may be deficient in a number of reducing enzymes, thus favouring formation of stable disulfide bonds as described in Bessette (*Proc. Natl. Acad. Sci. USA* 96:13703-13708 (1999)).

In a preferred embodiment of the present invention, *E. coli* used as a host cell is transformed with the expression vector containing the polynucleotide encoding one of the cell permeable recombinant proteins according to the present invention so as to produce the cell permeable recombinant protein at high levels. Methods for transforming bacterial cells are well known in the art, and include, but are not limited to, biochemical means as transformation, transfection, conjugation, protoplast fusion, calcium phosphate-precipitation, and application with polycations such as diethylaminoethyl (DEAE) dextran, and such mechanical means as electroporation, direct microinjection, microprojectile bombardment, calcium phosphate ($CaPO_4$) precipitation, calcium chloride ($CaCl_2$) precipitation, PEG-mediated fusion and liposome-mediated method.

The present invention provides a method of producing the cell permeable Nanog and Oct4 recombinant proteins at high levels, respectively, which comprises the step of culturing the above transformant.

The method of the present invention may be conducted by culturing the transformant in a suitable medium under suitable conditions for expressing a cell permeable recombinant protein of the present invention in the expression vector introduced into the transformant. Methods for expressing a recombinant protein by culturing a transformant are well known in the art, and for example, may be carried out by inoculating a transformant in a suitable medium for growing the transformant, performing a subculture, transferring the same to a main culture medium, culturing under suitable conditions, for example, supplemented with a gene expression inducer, isopropyl-β-D-thiogalactoside (IPTG) and, thereby, inducing the expression of a recombinant protein. After the culture is completed, it is possible to recover a "substantially pure" recombinant protein from the culture solution. The term "substantially pure" means that the recombinant protein and polynucleotide encoding the same of the present invention are essentially free of other substances with which they may be found in nature or in vivo systems to an extent practical and appropriate for their intended use. A "substantially pure" preparation or a substantially purified preparation would be about at least 85% pure, preferably about at least 95% pure. A "substantially pure" or "isolated" protein as described herein could be prepared by a variety of techniques well known to the skilled artisan.

A recombinant protein of the present invention obtained as above may be isolated from the inside or outside of host cells (e.g., medium), and purified as a substantially pure homogeneous polypeptide. The method for polypeptide isolation and purification is not limited to any specific method. In fact, any standard method may be used. For instance, column chromatography, filters, ultrafiltration, salting out, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the polypeptide.

For chromatography, for example, affinity chromatography, ion-exchange chromatography, hydrophobic chromatography, gel filtration chromatography, reverse phase chromatography, adsorption chromatography, etc. may be used (Strategies for Protein Purification and Characterization: A Laboratory Course Manual. Ed. Daniel R. Marshak et al., Cold Spring Harbor Laboratory Press (1996)). These chromatographies may be performed by liquid chromatographies, such as HPLC and FPLC. Thus, the present invention provides highly purified recombinant proteins produced by the above methods.

For isolation and purification of the recombinant protein of the present invention from a culture of the transformant for producing the recombinant protein of the present invention, conventional methods for the isolation and purification of proteins can be used.

For example, if the recombinant protein is accumulated as soluble forms in cells of the transformant for producing the same, the cells are recovered from the culture by centrifugation, then washed and disrupted with an ultrasonic disrupter, French Press, Manton-Gaulin homogenizer, Dynomill or the like, to obtain a cell-free extract.

A purified preparation can be obtained by centrifuging the cell free extract to obtain a supernatant, and then, by subjecting the supernatant to solvent extraction, salting-out or desalting with sulfate ammonium etc., precipitation with organic solvent, anion-exchange chromatography on resin, such as diethylaminoethyl (DEAE)-Sepharose, DIAION HPA-75 (Mitsubishi Chemical Industries Ltd., Tokyo, Japan) or the like, anion-exchange chromatography on resin such as S-Sepharose FF (Amersham Pharmacia Biotech, Uppsala, Sweden) or the like, hydrophobic chromatography on resin such as butyl Sepharose, phenyl Sepharose or the like, gel filtration using molecular sieve, affinity chromatography, chromatofocusing, and electrophoresis such as isoelectric focusing.

If the polypeptide is expressed as an inclusion body in cells, the cells are similarly recovered, disrupted and centrifuged to give a precipitated fraction. From the fraction, the polypeptide is then recovered in a usual manner, and the inclusion body of the polypeptide is solubilized with a polypeptide denaturating agent. The solubilized solution is then diluted with or dialyzed against a solution not containing the polypeptide denaturating agent or a solution containing the polypeptide denaturating agent at a low enough concentration not to denature the polypeptide whereby the solubilized polypeptide is renatured to have a normal tertiary structure, and its purified preparation can be obtained by using the same isolation and purification methods as described above.

If said polypeptide is extracellularly secreted, the culture is subjected to means, such as centrifugation, to give a soluble fraction. From the soluble fraction, a purified preparation of the polypeptide can be obtained in the same manner as for isolation and purification from the cell-free extract as described above.

In a preferred embodiment, it has been found that the cell permeable recombinant protein of the present invention mostly exists in the insoluble fraction as an inclusion body. In order to purify the recombinant protein from the insoluble fraction, the insoluble fraction is dissolved in a lysis buffer containing 8 M urea (100 mM $NaH_2PO_4$, 10 mM Tris-HCl, 8 M Urea, pH 8.0) subjected to ultrasonification, and then centrifuged to separate the precipitate. Thus separated precipitate is dissolved in a buffer supplemented with urea as a denaturant and centrifuged to separate the supernatant. The recombinant protein eluted from the insoluble fraction by using urea is purified by means of a His-bind purification kit and subjected to ultrafiltration on an amicon filter for salt removal and protein refolding, thereby obtaining a purified recombinant protein of the present invention.

Further, the present invention provides the combined use of the cell permeable Nanog and Oct4 recombinant proteins for increasing self-renewal and suppressing differentiation of stem cells.

Another aspect of the present invention provides a method of increasing self-renewal and suppressing differentiation of stem cells which comprises the step of treating the stem cells in combination with the cell permeable Nanog and Oct4 recombinant proteins.

The stem cell used in the method of the invention can be any pluripotent or multipotent mammalian stem cell.

Pluripotent cells have the ability to develop into any cell derived from the three main germ cell layers. Adult stem cells, placenta stem cells, fetal stem cells and umbilical stem cells may all be used, but preferred stem cells are embryonic stem (ES) cells, embryonic carcinoma (EC) cells or embryonic germ (EG) cells (U.S. Pat. No. 6,090,622; Donovan & amp; Gearhart, *Nature* 414:92-97 (2001)). Somatic, bone marrow and cord blood stem cells may be used, particularly where autologous AE2 cells are desired.

Representative examples of the stem cells may include, but are not limited to, inner cell mass (ICM)-derived embryonic stem cells, blastocyst-derived embryonic stem cells, adipocyte-derived mesenchymal stem cells, bone marrow-derived haematopoietic stem cells, umbilical cord blood-derived haematopoietic stem cells, placenta-derived haematopoietic stem cells, mobilized peripheral blood-derived haematopoietic stem cells, adult brain subventricular zone-derived neural stem cells, adult neocortex-derived neural stem cells, bone marrow-derived endothelial stem cells, olfactory mucosa-derived olfactory stem cells, testicle spermatogonial progenitor-derived testicular cells, mammary gland-derived mammary stem cells, somatic cell reprogramming-derived induced pluripotent stem cells and the like.

Methods for obtaining suitable stem cells and for maintaining them (e.g., in an undifferentiated state) prior to use in the process of the invention are well known.

ES cells are cells derived from embryos which can propagate indefinitely in vitro culture. ES cells are pluripotent i.e., they have the ability to give rise in vivo to all cell types which comprise the adult animal. Murine ES cells (U.S. Pat. No. 5,670,372) and human ES cells (U.S. Pat. No. 6,200,806; Thomson et al., *Science* 282:1145-7 (1998)) are readily available and conditions for their undifferentiated growth are well known (Smith et al., *Ann. Rev. Cell Dev. Biol.* 17:435-62 (2001); Wobus et al., *Mol. Aspects. Med.* 22:149-64 (2001); Tessarollo et al., *Methods Mol. Biol.* 158:47-63 (2001); Marshall et al., *Methods Mol. Biol.* 158:11-18 (2001); Wobus et al., *Cells Tissues Organs* 166:1-5 (2000); Pera et al., *J. Cell Sci.* 113:5-10 (2000); Embryonic Stem Cells: Methods and Protocols (ed. Turksen) (2002) ISBN 0896038815). ES cells are properly referred to as pluripotent rather than totipotent, as they are incapable of forming some non-embryonic cell types.

In order to ensure compatibility with human patients, human stem cells, and human ES cells in particular, are preferred for use according to the invention. Although it has not yet reached the levels of murine ES cells, knowledge on the growth and differentiation of human ES cells is advanced (Zhang et al. (2001) *Nature Biotechnol.* 19: 1129-1133; Donovan et al., *Nature* 414:92-97 (2001); Pera, *Curr Opin. Genet. Dev.* 11:595-599 (2001)). Where non-human patients are to be treated or studied, however, stem cells from other organisms (e.g., from non-human primates or from mice) may be used. Non-human stem cells may also be used with humans in conjunction with xenotransplantation compatibility techniques.

For administration to humans, it may be preferred to use autologous ES cells. These may be prepared by, for instance, preparing an embryo by somatic cell nuclear transfer from a patient, and deriving ES cells from the embryo. Autologous somatic stems cells may also be used.

Because the provision of large quantities of material for therapeutic use is advantageous, the stem cell is preferably capable of prolonged proliferation in vitro.

According to the present invention as described above, cell permeability is conferred upon Nanog and Oct4 by the expression of a recombinant protein with a kFGF4-derived MTD fused to the N-terminus and/or C-terminus of the expressed polypeptide.

Stem cells are not capable of keeping their identity ex vivo which is a unique capability for self-renewal and differentiation to all types of cells. For stem cell therapy, embryonic or adult stem cells have to be amplified in their cell population ex vivo while maintaining their unique identity. However, as the duration of the ex vivo culture is extended, their self-renewal and pluripotency are extremely hampered. Further, the ex vivo culture of prepared or isolated stem cells to increase their cell population easily induces aging and differentiation into various cell types, resulting in losing their stem cell identity.

In order to establish a personally tailored stem cell line, current research is focused on developing a method for maintaining the stem cell identity by increasing self-renewal and suppressing differentiation thereof. Therefore, the way to increase cell population and to inhibit differentiation of an isolated primary stem cell ex vivo culture is crucial to realize patient-specific or personally tailored stein cell therapy.

For this, the present invention uses in combination with the cell permeable Nanog and Oct4 recombinant proteins for increasing self-renewal and suppressing differentiation of stem cell.

If stem cells are treated in combination with the cell permeable Nanog and Oct4 recombinant proteins of the present invention, Nanog and Oct are successfully introduced into the nucleus of the cells, and thereby, increase self-renewal capability and suppress differentiation potential thereof while maintaining their undifferentiated state.

The stein cells characterized in terms of their unique identity, self-renewal capability, and differentiation potential, can be effectively used for treatment of diseases. The identification of such cells with the potential and ability to differentiate into any cell type present in an organism initially garnered interest in the treatment of autoimmune diseases and cancer, due to the immediate correlation with hematopoiesis and suitability for genetic modification of a pluripotent precursor, but has since expanded into nearly all areas of human disease. In addition to bone marrow restoration treatments for cancers, such as leukemia, as well as autoimmune diseases, stem cell therapies are also under consideration for treatments including repair of organ tissues following disease on injury. These proposed stem cell therapies involve the administration of primary stem cells and/or modified stem cells to a specific tissue site in an organism. Notable areas of application include diabetes, hepatic disease, spinal cord regeneration, bone regeneration, ocular regeneration, and cardiac repair.

As can be appreciated, there is great interest in isolating and growing stem cells from different species, particularly from primates and especially from humans, since such stem cells could provide a supply of readily available cells and tissues of all types for use in transplantation, cell regeneration and replacement therapy, drug discovery, generation of model systems for studying mammalian development, and gene therapy.

Unless defined otherwise, all technical and scientific terms used herein have the same meaning as commonly understood by one of ordinary skill in the art to which this invention belongs. Although any method and material similar or equivalent to those described herein can also be used in the practice or testing of the present invention, specific methods and materials are now described. All publications mentioned herein are incorporated herein by reference in their entirety to disclose and describe the methods and/or materials in connection with which the publications are cited.

It must be noted that as used herein and in the appended claims, the singular forms "a," "an," and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are presented to aid practitioners of the invention, provide experimental support for the invention, and to provide model protocols. In no way are these examples to be understood to limit the invention.

Example 1

Construction of Cell Permeable Recombinant Proteins

<1-1> Cell Permeable Nanog (CP-Nanog) Recombinant Protein

In order to construct a cell permeable Nanog (CP-Nanog) recombinant protein by using a kFGF4-derived MTD, three full-length and five truncated forms of CP-Nanog recombinant constructs were contrived.

The cell permeable Nanog recombinant protein of the present invention was composed of a kFGF4-derived MTD (SEQ ID NO: 6), a nuclear localization sequence (NLS) (SEQ ID NO: 8) derived from SV40 large T antigen, a histidine-tag (His-Tag) for easy purification, and a transcription factor Nanog (SEQ ID NO: 2).

Referring to FIG. 1, the full-length forms of a CP-Nanog recombinant constructs were as follows:

1) His-MTD-Nanog (HMN) wherein a kFGF4-derived MTD is fused to the N-terminus of a full-length Nanog;

2) His-Nanog-MTD (HNM) wherein a kFGF4-derived MTD is fused to the C-terminus of a full-length Nanog; and 3) His-MTD-Nanog-MTD (HMNM) wherein a kFGF4-derived MTD is fused to both termini of a full-length Nanog; wherein a His-tag and a NLS derived from SV40 large T antigen are covalently coupled to the N-terminus of all constructs.

In order to prepare the full-length CP-Nanog recombinant constructs, polymerase chain reaction (PCR) was carried out by using the oligonucleotides described in Table 1 below as a primer pair specific for each recombinant construct and a human Nanog cDNA (SEQ ID NO: 1) as a template. At this time, forward and reverse primers for amplifying His-MTD-Nanog (HMN) have nucleotide sequences represented by SEQ ID NOS: 36 and 39, respectively; those for amplifying His-Nanog-MTD (HNM) have nucleotide sequences represented by SEQ ID NOS: 35 and 40, respectively; those for amplifying His-MTD-Nanog-MTD (HMNM) have nucleotide sequences represented by SEQ ID NOS: 36 and 40, respectively.

Further, the truncate forms of a cell permeable Nanog recombinant protein were as follows:

1) His-Nanog N-terminal-MTD (HNNM) wherein a kFGF4-derived MTD is fused to the C-terminus of a Nanog N-terminal domain fragment lacking a homeodomain and a tryptophan repeat;

2) His-Nanog homeodomain-MTD (HNHM) wherein a kFGF4-derived MTD is fused to the C-terminus of a Nanog homeodomain fragment lacking N-terminal and C-terminal domains;

3) His-Nanog C-terminal MTD (HNCM) wherein a kFGF4-derived MTD is fused to C-terminus of a Nanog C-terminal domain lacking an N-terminal domain and a homeodomain;

4) His-Nanog N-terminal-homeodomain-MTD (HNNHM) wherein a kFGF4-derived MTD is fused to the C-terminus of a Nanog N-terminal domain and homeodomain fragment lacking a C-terminal domain; and 5) His-Nanog homeodomain-C-terminal-MTD (HNHCM) wherein a kFGF4-derived MTD is fused to the C-terminus of a Nanog homeodomain and C-terminal domain fragment lacking an N-terminal domain;

wherein a His-tag and a NLS derived from SV40 large T antigen are covalently coupled to the N-terminus of all constructs.

In order to prepare the truncated CP-Nanog recombinant proteins, PCR was carried out by using the oligonucleotides described in Table 1 below as a primer set specific for each recombinant protein and a human Nanog cDNA (SEQ ID NO: 1) as a template. At this time, forward and reverse primers for amplifying His-Nanog N-terminal-MTD (HNNM) have nucleotide sequences represented by SEQ ID NOS: 35 and 41, respectively; those for amplifying His-Nanog homeodomain-MTD (HNHM) have nucleotide sequences represented by SEQ ID NOS: 37 and 41, respectively; those for amplifying His-Nanog C-terminal MTD (HNCM) have nucleotide sequences represented by SEQ ID NOS: 38 and 41, respectively; those for amplifying His-Nanog N-terminal-homeodomain-MTD (HNNHM) have nucleotide sequences represented by SEQ ID NOS: 35 and 41, respectively; those for amplifying His-Nanog homeodomain-C-terminal-MTD (HNHCM) have nucleotide sequences represented by SEQ ID NOS: 37 and 40, respectively.

TABLE 1

| Primer | Sequence | SEQ ID NO |
|---|---|---|
| HN-5' (45 nts) | 5'-CCG CAT ATG AAG AAG AAG AGG AAG AGT GTG GAT CCA GCT TGT CCC-3' | 35 |
| HMN-5' (84 nts) | 5'-CCG CAT ATG AAG AAG AAG AGG AAG GCA GCC GTT CTT CTC CCT GTT CTT CTT GCC GCA CCC AGT GTG GAT CCA GCT TGT CCC CAA-3' | 36 |
| HNH-5' (51 nts) | 5'-CCG CAT ATG AAG AAG AAG AGG AAG CAG AAG ACC AGA ACT GTG TTC TCT TCC-3' | 37 |
| HNC-5' (51 nts) | 5'-CCG CAT ATG AAG AAG AAG AGG AAG AAC AAC TGG CCG AAG AAT AGC AAT GGT-3' | 38 |
| HN-3' (36 nts) | 5'-CCG CAT ATG TCA CAC GTC TTC AGG TTG CAT GTT CAT-3' | 39 |
| HNM-3' (72 nts) | 5'-CCG CAT ATG TCA GGG TGC GGC AAG AAG AAC AGG GAG AAG AAC GGC TGC CAC GTC TTC AGG TTG CAT GTT CAT-3' | 40 |
| HNHM-3' (72 nts) | 5'-CCG CAT ATG TCA GGG TGC GGC AAG AAG AAC AGG GAG AAG AAC GGC TGC TTT CTG CCA CCT CTT AGA TTT CAT-3' | 41 |
| HNNM-3' (75 nts) | 5'-CCG CAT ATG TCA GGG TGC GGC AAG AAG AAC AGG GAG AAG AAC GGC TGC TTT CTT GAC TGG GAC CTT GTC TTC CTT-3' | 42 |

PCR was performed in a 50 μl reaction containing 100 ng of human Nanog cDNA as a template, 0.2 mM dNTP mixture (dGTP, dATP, dTTP, and dCTP, each at 2 mM), 0.6 μM of each primer, 5 μl of 10× Taq buffer, 1 μl of Taq polymerase (Takara, Japan). The PCR reaction was performed 25 cycles at 94° C. for 45 seconds, 53° C. for 45 seconds and 72° C. for 45 seconds after the initial denaturation of 94° C. for 2 minutes, followed by the final extension of 72° C. for 5 minutes. After the PCR reaction was completed, the amplified PCR product was digested with restriction enzyme NdeI and loaded onto a 1.0% agarose gel and fractionated. As shown in FIG. 3, it was confirmed that the expected fragment for each recombinant construct fused to a kFGF4-derived MTD was successfully amplified.

The DNA band of expected size was excised from the gel, eluted and purified by using a QIAquick Gel extraction kit (Qiagen, USA). The eluted DNA was precipitated with ethanol and resuspended in 6 μl of distilled water for ligation.

As shown in FIG. 4, the PCR amplified DNA fragment containing the coding region was subcloned into a pGEM-T Easy vector (Promega, Madison Wis., USA) with a T4 ligase according to the TA cloning method, and then, followed by transforming E. coli DH5α competent cells with the pGEM-T Easy vector. The cells were plated onto LB plate media supplemented with 50 μg/ml of ampicillin and cultured at 37° C. for overnight. After the recombinant fragment inserted pGEM-T Easy vector was isolated by treating with restriction enzyme NdeI, it was subjected to 0.8% agarose gel electrophoresis. As shown in FIG. 4, DNA fragments of about 1 kb for the full-length form and about 0.3 to 0.7 kb for the truncated forms and vector fragments of about 3 kb were detected, which confirms that the insert DNA of Cp-Nanog recombinant construct was appropriately subcloned into pGEM-T Easy vector.

A pET-28(+)a vector (Novagen, Madison, Wis.) bearing a histidine-tag and a T7 promoter was digested with a restriction enzyme NdeI (Enzynomics, Korea). The pET-28a(+) plasmid is designed to facilitate His-tag fusions at either the N-terminus or C-terminus and to provide strong expression of the genes in E. coli from the T7 phage promoter. Each of the isolated insert DNA fragments encoding MTD-Nanog recombinant constructs was cloned into the pre-treated pET-28a(+) as described above. At the 3' end of each CP-Nanog encoding gene, the coding sequence was fused in frame at the NdeI site to the His-tag sequence followed by a translation stop codon, resulting in the production of CP-Nanog recombinant proteins with six histidine residues (SEQ ID NO: 47) added to the C-terminus for the sake of easy purification on nickel columns.

After the clones were treated with the restriction enzyme NdeI and subjected to 0.8% agarose gel electrophoresis, it was verified that DNA fragments of about 1 kb for the full-length form and about 0.3 to 0.7 kb for the truncated forms and vector fragments of about 5 kb were detected, which confirms the cloning of the insert DNA of CP-Nanog recombinant construct into pET-28a(+) vector, as shown in FIG. 5.

The successfully cloned expression vectors for expressing cell permeable Nanog recombinant proteins was designated pET28a(+)-HMN, pET28a(+)-HNM, pET28a(+)-HMNM, pET28a(+)-HNNM, pET28a(+)-HNHM, pET28a(+)-HNCM, pET28a(+)-HNNHM, and pET28a(+)-HNHCM, respectively.

Among them, the expression vector pET28a(+)-HNM containing His-Nanog-kFGF4-derived MTD construct was deposited on Feb. 22, 2008 in accordance with the Budapest Treaty under accession numbers KCTC 11278BP with the Korean Collection for Type Cultures (KCTC), Korea Research Institute of Bioscience and Biotechnology (KRIBB), 52, Oun-Dong, Yusong-Ku, Taejon 305-333, Republic of Korea.

In the cell permeable Nanog recombinant proteins in a full-length form as constructed above, His-MTD-Nanog (HMN) has an amino acid sequence represented by SEQ ID NO: 19 and a polynucleotide encoding the same has a nucleotide sequence represented by SEQ ID NO: 10; His-Nanog-MTD (HNM) has an amino acid sequence represented by SEQ 1D NO: 20 and a polynucleotide encoding the same has a nucleotide sequence represented by SEQ ID NO: 11; His-MTD-Nanog-MTD (HMNM) has an amino acid sequence represented by SEQ ID NO: 21 and a polynucleotide encoding the same has a nucleotide sequence represented by SEQ ID NO: 12.

Further, in the cell permeable Nanog recombinant proteins in a truncated form for as constructed above, His-Nanog N-terminal-MTD (HNNM) has an amino acid sequence represented by SEQ ID NO: 22 and a polynucleotide encoding the same has a nucleotide sequence represented by SEQ ID NO: 13; His-Nanog homeodomain-MTD (HNHM) has an amino acid sequence represented by SEQ ID NO: 23 and a polynucleotide encoding the same has a nucleotide sequence represented by SEQ ID NO: 14; His-Nanog C-terminal MTD (HNCM) has an amino acid sequence represented by SEQ ID NO: 24 and a polynucleotide encoding the same has a nucleotide sequence represented by SEQ ID NO: 15; His-Nanog N-terminal-homeodomain-MTD (HNNHM) has an amino acid sequence represented by SEQ ID NO: 25 and a polynucleotide encoding the same has a nucleotide sequence represented by SEQ ID NO: 16; His-Nanog homeodomain-C-terminal-MTD (HNHCM) has an amino acid sequence represented by SEQ ID NO: 26 and a polynucleotide encoding the same has a nucleotide sequence represented by SEQ ID NO: 17.

As a control for the cell permeable Nanog recombinant proteins, His-Nanog (HN), where a full-length Nanog is fused to only a nuclear localization sequence (NLS) derived from SV40 large T antigen and a histidine-tag (His-Tag) lacking a kFGF4-derived MTD, was constructed. The control protein has an amino acid sequence represented by SEQ ID NO: 18 and a polynucleotide encoding the same has a nucleotide sequence represented by SEQ ID NO: 9.

<1-2> Cell Permeable Oct4 (CP-Oct4) Recombinant Protein

In order to construct a cell permeable Oct4 (CP-Oct4) recombinant protein by using a kFGF4-derived MTD, three full-length forms of CP-Oct4 recombinant constructs were contrived.

The cell permeable Oct4 recombinant protein of the present invention contains a kFGF4-derived MTD (SEQ ID NO: 6), a nuclear localization sequence (NLS) (SEQ ID NO: 8) derived from SV40 large T antigen, a histidine-tag (His-Tag) for easy purification, and a transcription factor Nanog (SEQ ID NO: 4).

Referring to FIG. 2, the full-length forms of a CP-Oct4 recombinant constructs were as follows:

1) His-MTD-Oct4 (HMO) wherein a kFGF4-derived MTD is fused to the N-terminus of a full-length Oct4;

2) His-Oct4-MTD (HOM) wherein a kFGF4-derived MTD is fused to the C-terminus of a full-length Oct4; and 3) His-MTD-Oct4-MTD (HMOM) wherein a kFGF4-derived MTD is fused to both termini of a full-length Oct4;

wherein a His-tag and a NLS derived from SV40 large T antigen are covalently coupled to the N-terminus of all constructs.

In order to prepare the full-length CP-Oct4 recombinant proteins, PCR was carried out by using the oligonucleotides described in Table 2 below as a primer set specific for each recombinant protein and a human Oct4 cDNA (SEQ ID NO: 3) as a template. At this time, forward and reverse primers for amplifying His-MTD-Oct4 (HMO) have nucleotide sequences represented by SEQ ID NOS: 44 and 45, respectively; those for amplifying His-Oct4-MTD (HOM) have nucleotide sequences represented by SEQ ID NOS: 43 and 46, respectively; those for amplifying His-MTD-Oct4-MTD (HMOM) have nucleotide sequences represented by SEQ ID NOS: 44 and 46, respectively.

TABLE 2

| Primer | Sequence | SEQ ID NO |
|---|---|---|
| HO-5' (45 nts) | 5'-CCG CAT ATG AAG AAG AAG AGG AAG GCG GGA CAC CTG GCT TCG GAT-3' | 43 |
| HMO-5' (84 nts) | 5'-CCG CAT ATG AAG AAG AAG AGG AAG GCA GCC GTT CTT CTC CCT GTT CTT CTT GCC GCA CCC GCG GGA CAC CTG GCT TCG GAT TTC-3' | 44 |
| HO-3' (36 nts) | 5'-CCG CAT ATG TCA GTT TGA ATG CAT GGG AGA GCC CAG-3' | 45 |
| HOM-3' (72 nts) | 5'-CCG CAT ATG TCA GGG TGC GGC AAG AAG AAC AGG GAG AAG AAC GGC TGC GTT TGA ATG CAT GGG AGA GCC CAG-3' | 46 |

PCR was performed in a 50 µl reaction containing 100 ng of human Nanog cDNA as a template, 0.2 mM dNTP mixture (dGTP, dATP, dTTP, and dCTP, each at 2 mM), 0.6 µM of each primer, 5 µl of 10× Taq buffer, 1 µl of Taq polymerase (Takara, Japan). The PCR reaction was performed 25 cycles at 94° C. for 45 seconds, 53° C. for 45 seconds and 72° C. for 45 seconds after the initial denaturation of 94° C. for 2 minutes, followed by the final extension of 72° C. for 5 minutes. After the PCR reaction was completed, the amplified PCR product was digested with restriction enzyme NdeI and loaded onto a 1.0% agarose gel and fractionated. As shown in FIG. 3, it was confirmed that the expected fragment for each recombinant construct fused to a kFGF4-derived MTD was successfully amplified.

The DNA band of expected size was excised from the gel, eluted and purified by using a QIAquick Gel extraction kit (Qiagen, USA). The eluted DNA was precipitated with ethanol and resuspended in 6 µl of distilled water for ligation.

As shown in FIG. 4, the PCR amplified DNA fragment containing the coding region was subcloned into a pGEM-T Easy vector (Promega, Madison Wis., USA) with a T4 ligase according to the TA cloning method, and then, followed by transforming E. coli DH5α competent cells with the pGEM-T Easy vector. The cells were plated onto LB plate media supplemented with 50 µg/ml of ampicillin and cultured at 37° C. for overnight. After the recombinant fragment inserted pGEM-T Easy vector was isolated by treating with restriction enzyme NdeI, it was subjected to 0.8% agarose gel electrophoresis. As shown in FIG. 4, DNA fragments of about 1.1 kb and vector fragments of about 3 kb were detected, which confirms that the insert DNA of CP-Oct4 recombinant construct was appropriately subcloned into pGEM-T Easy vector.

A pET-28(+)a vector (Novagen, Madison, Wis.) bearing a histidine-tag and a T7 promoter was digested with a restriction enzyme NdeI (Enzynomics, Korea). Each of the isolated insert DNA fragments encoding MTD-Nanog was cloned into the pre-treated pET-28a(+) as described above. At the 3' end of each CP-Oct4 encoding gene, the coding sequence was fused in frame at the NdeI site to the His-tag sequence followed by a translation stop codon, resulting in the production of CP-Oct4 recombinant proteins with six histidine residues (SEQ ID NO: 47) added to the C-terminus for the sake of easy purification on nickel columns.

After the clones were treated with the restriction enzyme NdeI and subjected to 0.8% agarose gel electrophoresis, it was verified that DNA fragments of about 1.1 kb and vector fragments of about 5 kb were detected, which confirms the cloning of the insert DNA of CP-Oct4 recombinant construct into pET-28a(+) vector, as shown in FIG. 5.

The successfully cloned expression vectors for expressing cell permeable Oct4 recombinant proteins were designated pET28a(+)-HMO, pET28a(+)-HOM and pET28a(+)-HMOM, respectively.

The expression vectors pET28a(+)-HMO containing His-kFGF4-derived MTD construct-Oct4; pET28a(+)-HOM containing His-Oct4-kFGF4-derived MTD construct; and pET28a(+)-HMOM containing His-kFGF4-derived MTD-Oct4-kFGF4-derived MTD construct was deposited on Feb. 22, 2008 in accordance with the Budapest Treaty under accession numbers KCTC 11279BP, KCTC 11280BP and KCTC 11281BP, respectively, with the Korean Collection for Type Cultures (KCTC), Korea Research Institute of Bioscience and Biotechnology (KRIBB), 52, Oun-Dong, Yusong-Ku, Taejon 305-333, Republic of Korea.

In the cell permeable Oct4 recombinant proteins in a full-length form as constructed above, His-MTD-Oct4 (HMO) has an amino acid sequence represented by SEQ ID NO: 32 and a polynucleotide encoding the same has a nucleotide sequence represented by SEQ ID NO: 28; His-Oct4-MTD (HOM) has an amino acid sequence represented by SEQ ID NO: 33 and a polynucleotide encoding the same has a nucleotide sequence represented by SEQ ID NO: 29; His-MTD-Oct4-MTD (HMOM) has an amino acid sequence represented by SEQ ID NO: 34 and a polynucleotide encoding the same has a nucleotide sequence represented by SEQ ID NO: 30.

As a control for the cell permeable Oct4 recombinant proteins, His-Nanog (HN), where a full-length Oct4 is fused to only a nuclear localization sequence (NLS) derived from SV40 large T antigen and a histidine-tag (His-Tag) lacking a kFGF4-derived MTD, was constructed. The control protein has an amino acid sequence represented by SEQ ID NO: 31, and a polynucleotide encoding the same has a nucleotide sequence represented by SEQ ID NO: 27.

Example 2

Inducible Expression of Cell Permeable Nanog and Oct4 Recombinant Proteins

<2-1> Selection of an Optimal Bacterial Strain

To choose the best bacterial strain for the expression of cell permeable Nanog and Oct4 recombinant proteins fused to a kFGF4-derived MTD prepared as described in Example 1 above, the expression vectors comprising each of His-Nonag-MTD (HN), His-MTD-Oct4 (HMO), His-Oct4-MTD (HOM), His-MTD-Oct4-MTD (HMOM) recombinant constructs were transfected in E. coli BL21 (DE3), BL21-Gold (DE3), BL21-CodonPlus (DE3) and BL21-GoldpLysS (DE3) strains, respectively. At this time, the His-Nanog (HN) and His-Oct4 (HO) expression vectors having no kFGF4-derived MTD were used as a control.

After the transfection, cells were grown at 37° C. in an LB medium containing kanamycin (30 μg/ml) with vigorous shaking until the optical density 600 ($OD_{600}$) reached between 0.4 and 0.6. IPTG (isoprophyl-β-D-thiogalactoside) was then added thereto at a final concentration of 0.7 mM to induce the expression of the CP-Nanog and CP-Oct4 recombinant proteins. Protein induction was prolonged for 3 hours at 37° C. The CP-Nanog and CP-Oct4 recombinant proteins expressed in said *E. coli* strains with IPTG were loaded on a SDS-PAGE gel, stained with Coomassie Brilliant Blue, and then destained. The most CP-Nanog and CP-Oct4 recombinant proteins were expressed at high levels in BL21-Gold-pLysS (DE3). However, some CP-Nanog recombinant proteins were not expressed in BL21-GoldpLysS (DE3).

From these results, BL21-GoldpLysS (DE3) was selected as an optimal strain for the expression of cell permeable recombinant proteins according to the present invention.

<2-2> Expression of Cell Permeable Nanog and Oct4 Recombinant Proteins

According to the same method as described in Example <2-1>, the expression vectors comprising each of the His-Nonag-MTD (HN), His-MTD-Oct4 (HMO), His-Oct4-MTD (HOM), His-MTD-Oct4-MTD (HMOM) recombinant constructs were transfected in BL21-GoldpLysS (DE3), selected as an optimal strain for their expression in Example <2-1>, respectively, the cells were cultured, and then, IPTG was added thereto. After the IPTG induction was completed, the culture solution was centrifuged to separate soluble and insoluble fractions. Thus obtained soluble and insoluble fractions of CP-Nanog and CP-Oct4 recombinant proteins expressed in the *E. coli* strain with IPTG were loaded on a SDS-PAGE gel.

As shown in FIG. 6, it was confirmed that the majority of the cell permeable Nanog and Oct4 recombinant proteins were included in the insoluble fraction as an inclusion body, and their expression was significantly increased in the presence of IPTG.

Example 3

Purification of Cell Permeable Nanog and Oct4 Recombinant Proteins

The inducible expression of cell permeable Nanog and Oct4 recombinant proteins in an *E. coli* system leads to the formation of insoluble aggregates, which are known as inclusion bodies. To completely solubilize these inclusion bodies, all of the above expressed proteins were denatured by dissolving them in 8 M urea. Denatured CP-Nanog and CP-Oct4 recombinant proteins were purified by histidine-tag affinity chromatography, using a nickel nitrilotriacetate resin (Qiagen, Hilden, Germany). Since strong denaturants, such as 8 M urea, completely solubilize the inclusion bodies, the purification method was carried out under pH-dependent denaturing conditions.

The *E. coli* culture solutions were harvested by centrifugation at 4,000×g for 20 minutes, resuspended in a lysis buffer (100 mM $NaH_2PO_4$, 10 mM Tris-HCl, 8 M Urea, pH 8.0), and subjected to ultrasonication on ice using a sonicator equipped with a probe. The cell lysates were centrifuged at 7,000×g for 20 minutes, so as to separate the supernatant and the cellular debris pellet. The supernatant was taken out and then incubated with a Ni-NTA resin equilibrated with the lysis buffer by gently shaking (using a rotary shaker) for 2 hours to overnight. After washing with a washing buffer (100 mM $NaH_2PO_4$, Tris-HCl, 8 M Urea, pH 6.3) five times, the proteins bound to the resin were eluted with an elution buffer (100 mM $NaH_2PO_4$, Tris-HCl, 8 M Urea, pH 4.5). The CP-Nanog and CP-Oct4 recombinant proteins purified under the denaturing conditions described above were analyzed on a SDS-PAGE gel and stained with Coomassie Brilliant Blue, where the results thereof are shown in FIG. 7.

In order to renature the His-tagged recombinant proteins purified above, the denatured proteins were refolded by removing the denaturant. Urea was removed from the proteins by dialyzing them against a refolding buffer (0.55 M Guanidine HCl, 0.44 M L-Arginine, 50 mM Tris-HCl, 150 mM NaCl, 1 mM EDTA, 100 mM NDSB, 2 mM Glutathione Oxidized, and 0.2 mM Glutathione Reduced). All of the refolded recombinant proteins were dialyzed for 9 hours against a physiological buffer, such as a cell culture medium (e.g., α-minimum essential medium: α-MEM) supplemented with 1% penicillin/streptomycin at 4° C. After the replacement of the refolding buffer with α-MEM, the cell permeabilities of all of the purified recombinant proteins were ready to be determined in vitro and in vivo.

According to the SDS-PAGE analysis results shown in FIG. 7, the cell permeable Nanog and Oct4 recombinant proteins were detected as a single band corresponding to about 37 and 43 kDa, respectively, which confirms that the cell permeable recombinant proteins of the present invention were purely purified from the insoluble fraction.

Example 4

Determination of Quantitative Cell Permeability of Cell Permeable Nanog and Oct4 Recombinant Proteins In order to quantitatively determine the cell permeability of the Nanog and Oct4 recombinant proteins fused to kFGF4-derived MTD according to the present invention in mammalian cells, cellular uptake of each recombinant protein was compared with that of a control lacking said MTD.

First, the four CP-Nanog and CP-Oct4 recombinant proteins (HNM, HMO, HOM, and HMOM) purified in a soluble form, as described in Example 3 above, were mixed with 0.7 μg/μl of fluorescein isothiocyanate (FITC) and reacted at room temperature for 1 hours by stirring. The reaction solution was subjected to a dialysis against Dulbecco's modified Eagle's medium (DMEM; WelGENE Inc., Korea) for 2 days until the FITC was completely removed to thereby obtain FITC-conjugated recombinant proteins. RAW 264.7 cells derived from mouse macrophage were maintained in DMEM supplemented with 10% fetal bovine serum and 1% penicillin (500 mg/ml, WelGENE Inc.) and incubated at 37° C. in a humidified atmosphere of 5% $CO_2$ in air. After the incubation, the cells were incubated with 10 μM of each of the FITC-conjugated recombinant proteins prepared above for 1 hour at 37° C., followed by treating them with Trypsin/EDTA (T/E, Invitrogen, Carlsbad, Calif.) to remove cell surface bound proteins and washing with cold PBS three times.

The cells treated with the FITC-conjugated recombinant proteins of the present invention were subjected to fluorescence-activated cell sorting (FACS) analysis (FACS Calibur, Beckton-Dickinson, San Diego, Calif.). For each sample, the cells ($1×10^4$) were analyzed by using the CellQuest Pro cytometric analysis software. Each experiment was conducted at least twice. The cell permeable potency of each CP-Nanog and CP-Oct4 recombinant protein fused to kFGF4-derived MTD was visually compared to that of a control protein lacking the MTD.

FIGS. 8 and 9 show the results of a flow cytometry analysis where the gray filled curve represents cell only, the black curve represents FITC only, the blue curve represents the cell permeability of a control (HN and HO), and the red curve represents the cell permeability of each recombinant protein (HNM, HMO, HOM and HMOM).

Referring to the results shown in FIGS. 8 and 9, it was found that all of the cell permeable Nanog and Oct4 recombinant proteins according to the present invention exhibit significantly higher levels of plasma membrane-penetrating ability than a control.

Example 5

Determination of Cell Permeability and Intracellular Localization of Cell Permeable Nanog and Oct4 Recombinant Proteins To visualize intracellular localization of delivered human Nanog and Oct4 proteins into a cell, NIH 3T3 cells were treated without (cell only) or with FITC (FITC only), or FITC-conjugated recombinant proteins lacking kFGF4-derived MTD (control: HN and HO) or FITC-conjugated recombinant proteins fused to kFGF4-derived MTD (HNM, HMO, HOM, and HMOM), and visualized by confocal laser scanning microscopy.

NIH 3T3 cells were cultured for 24 hours in an 8-well chamber slide (LabTek, Nalgen Nunc, Rochester N.Y.). Cells were maintained in DMEM supplemented with 10% fetal bovine serum, 1% penicillin and streptomycin in 5% $CO_2$ at 37° C. The cells were washed with PBS three times, and then treated for 1 hour with serum-free DMEM, serum-free DMEM plus free FITC, or serum-free DMEM containing 10 μM FITC-conjugated recombinant proteins in 5% $CO_2$ at 37° C. One hour after the treatment, the cells were fixed in 4% paraformaldehyde (PFA) for 20 minutes at room temperature for observation.

For the direct detection of FITC-conjugated recombinant proteins that were internalized, the cells were washed with PBS three times and counterstained with a nuclear fluorescent stain solution, propidium iodide (PI, Sigma-Aldrich, St. Louis, Mo.), at a concentration of 1 μg/ml. After PI staining for 5 minutes, the cells were washed with PBS three times and fixed by polyvinyl alcohol mountain medium with DABCO (Fluca, St Louis, Mo.). The intracellular distribution of the fluorescence was determined at the middle of a single cell analyzed by confocal laser scanning microscopy, where the results are shown in FIGS. 10 and 11. Parameters specific for each fluorochrome were followed as FITC: excited at 488 nm light, detected with a 530 nm bandpass filter.

Surprisingly, as shown in FIGS. 10 and 11, the FITC-conjugated CP-Nanog and CP-Oct4 recombinant proteins were well distributed largely in the nucleus as compared with the cell only, FITC only and a control lacking a kFGF4-derived MTD. Intracellular nuclear localization of cell permeable Nanog and Oct4 recombinant proteins fused to SV40 Large T antigen-derived NLS and kFGF4-derived MTD completely coincided with the cellular uptake efficiency of the proteins determined by flow cytometry.

Example 6

Increase in Cell Population and Suppression of Cell Differentiation of Adult Stem Cells Treated in Combination with Cell Permeable Nanog and Oct4 Recombinant Proteins Two transcription factors, Nanog and Oct4 are thought to work in concert to maintain pluripotency and self-renewal in the inner cell mass (ICM) and embryonic stem (ES) cells. Accordingly, it was examined whether adult stem cells can maintain their self-renewing and differentiation ability by combinedly treating with the cell permeable Nanog and Oct4 recombinant proteins of the present invention as follows.

As human adult stem cells, employed were mesenchymal stem cells (MSCs) prepared from liposuction-derived adipocytes. The stem cells were cultured in α-minimum essential media (α-MEM) supplemented with 10% fetal bovine serum (FBS) at 37° C. in humidified atmosphere of 5% $CO_2$ for 24 hours. The cells were distributed to five 6-mm culture dishes containing 5 ml of α-MEM at a concentration of $1.5 \times 10^4$ cells per dish, respectively, and combinedly treated with the cell permeable Nanog and Oct4 recombinant proteins (HNM+HMO, HNM+HOM, or HNM+HMOM) at each concentration of 10 μM at 3-day intervals for 15 days. At this time, the cells treated without the recombinant proteins (cell only) were used as a negative control, and they treated in combination with the Nanog and Oct4 control proteins lacking a kFGF4-derived MTD (HN+HO) were used as a positive control. The number of cells was counted under inverted microscope (Nikon Eclipse TS100, Kawasaki, Japan) before the treatment (Day 0), and 4, 11, and 15 days after the treatment in selected nine circular areas (r=1 mm) three times and averaged.

As illustrated in FIGS. 12 and 13, until Day 12 after the treatment, the number of cells treated in combination with CP-Nanog and CP-Oct4 recombinant proteins was significantly increased compared to that of cells having no treatment (cell only) and treatment in combination with Nanog and Oct4 control proteins (HN+NO), which suggests that Nanog and Oct4 are successfully introduced into the nucleus of MSCs, thereby maintaining self-renewing activity during ex vivo cultivation. Regardless of the protein treatment, all cultured cells were suddenly died at Day 15, which was presumably due to the end of replicative life-span of the cells. Only in the combined treatment group of HNM+HOM, 2 cells survived and were isolated as a primary stem cell, suggesting potential establishment of a stem cell line maintaining its unique identity, self-renewal capability and differentiation potential. On the other hand, 7 cells survived in the group having no treatment at Day 11 after the culture were completely changed their cell morphology, which suggests differentiation into other cell types and aging, as depicted in FIG. 14.

Further, FIG. 12 showed that Day 11 after the treatment, the cells from the no treatment group (cell only) and HN+HO treatment group were differentiated, leading to certain morphological change into different cell types, while the cells of the combined CP-Nanog and CP-Oct4 treatment groups (HN+HO, HNM+HMO and HNM+HMOM) still maintained the characteristic morphology of mesenchymal stem cells and kept it at least for 34 days even after the termination of the protein treatment.

To examine whether the combined treatment of CP-Nanog and CP-Oct4 recombinant proteins can inhibit differentiation and aging of the isolated stem cells, the combined treatment was terminated at Day 15, the two isolated cells survived in the group of HNM+HOM and seven isolated cells survived in the group having no treatment (cell only) were further cultured for 34 days in the absence of CP-Proteins after the termination of the treatment.

FIG. 15a is a photograph of inverted microscope (Nikon Eclipse TS100, Kawasaki, Japan) visualizing the self-renewal and suppressive differentiation ability of clonal adult stem cells selected after the combination treatment of cell permeable Nanog and Oct4 recombinant proteins is terminated, and FIG. 15b is a graph illustrating the number of clonal adult stem cells selected after the same treatment. As shown in FIGS. 15a and 15b, the number of cells selected from the group of HNM+HOM was significantly increased (62 cells) as time goes, as compared with that of cells selected from the cell only group (15 cells) at Day 44 (when the cells were further cultured for 29 days after the termination of the treatment). At Day 49 when the cells were further cultured for 34 days after the termination of the treatment, all cells derived from the cell only group died. However, the cells derived from the HNM+HOM treated group still survived without any morphological change.

These results suggest that the combined treatment of CP-Nanog and CP-Oct4 recombinant proteins according to the present invention can significantly increase the number of stem cells and potentially inhibit cell differentiation and cellular aging.

Example 7

Inhibition of p21 Expression in Adult Stein Cells Treated in Combination with Cell Permeable Nanog and Oct4 Recombinant Proteins To evaluate the biochemical function of CP-Nanog and CP-Oct4 recombinant proteins on mesenchymal stem cells (MSCs), a Western blot analysis was performed as follows.

The cells were harvested from the five experimental groups of cell only, combined treatment of Nanog and Oct control proteins lacking kFGF4-derived MTD (HN+HO) and combined treatment of CP-Nanog and CP-Oct4 recombinant proteins (HNM+HMO, HNM+HOM and HNM+HMOM) at Day 0, Day 5, and Day 8, respectively, according to Example 6 above, and washed with PBS. The cells were then lysed in RIPA buffer (20 mM Tris-HCl [pH 8], 137 mM NaCl, 10% Glycerol, 1% Triton X-100, 2 mM EDTA) containing Protease Inhibitor Cocktail (Roche Molecular Biochemicals, GmbH, Mannheim, Germany) and incubated on ice for 20 minutes, to thereby obtain a cell lysate. The cell lysate was centrifuged at 4° C. for 10 minutes at 13,000 rpm to separate a supernatant. Thus obtained supernatant was resolved on a 12% sodium dodecyl sulfate-polyacrylamide gel (SDS-PAGE) and transferred onto a PDVF membrane (immobilon-P$^{SQ}$) (Bedford, Mass., USA) using the Trans-Blot system of NuPAGE (Invitrogen, Carlsbad, Calif., USA). The PVDF membrane was blocked with 5% non-fat dry milk in TBST (10 mM Tris, 100 mM NaCl, 0.1% Tween 20, pH 7.5), followed by incubation with an anti-p21 antibody (Santa Cruz Biotechnology, Santa Cruz, Calif.) diluted 1:1000 in 5% TBST for 1 hour at room temperature. The membrane was washed with TBST and incubated with a horseradish peroxidase-conjugated secondary antibody (Santa Cruz Biotechnology, Santa Cruz, Calif.), diluted 1:1000 in TBST, for 1 hour at room temperature. After washing with TBST, the membrane was stained using the ECL plus system (Amersham Pharmacia Biotech, Uppsala, Sweden) to visualize the antigen/antibody interaction.

As shown in FIG. 16, p21 expression was inhibited almost completely in the cells treated with combined CP-Nanog and CP-Oct4 recombinant proteins (HNM+HMO, HNM+HOM and HNM+HMOM), as compared with those treated with nothing (cell only) or with control proteins (HN+HO). Significantly decreased expression of p21, which is a cycline dependent kinase (CDK) inhibitor, suggests that the combination treatment of CP-Nanog and CP-Oct4 according to the present invention strongly induce cell cycle progression for self-renewal of the treated stem cells.

Example 8

Increase in Telomerase Activity of Adult Stem Cells Treated in Combination with Cell Permeable Nanog and Oct4 Recombinant Proteins To determine whether adult stem cells treated with combined CP-Nanog and CP-Oct4 recombinant proteins have the characteristics of established stem cell lines, telomerase activity was measured. Immortal cells, such as germ cells, express very high level of telomerase activity. Telomerase is a ribonucleoprotein which is involved in maintaining telomere length by adding telomere repeats to chromosome ends, resulting in extending replicative life-span.

Telomerase activity of mesenchymal stem cells treated in combination with CP-Nanog and CP-Oct4 recombinant proteins were determined by Telomeric Repeat Amplication Protocol (TRAP) assay using TRAPEZE® Telomerase Detection Kit (Chemicon international Inc., Temecula, Calif.). The cells treated with nothing (cell only), with Nanog and Oct4 control proteins (HN+NO) and Cp-Nanog and CP-Oct4 recombinant proteins (HNM+HMO, HNM+HOM and HNM+HMOM) were harvested at Day 0 and Day 3 after the treatment. Cell pellets were suspended in 1×CHAPS lysis buffer (10 mM Tris-HCl pH 7.5, 1 mM MgCl$_2$, 1 mM EGTA, 0.1 mM (3-mercaptoethanol, 0.5% CHAPS, 10% Glycerol) and incubated on ice for 30, followed by centrifuging for 20 minutes at 13,000 rpm to separate supernatants. Thus, obtained supernatants were used for PCR under the conditions as followed: 30 cycles at 94° C. for 30 seconds, 59° C. for 30 seconds, and 72° C. for 1 minute. The amplified PCR products were loaded on 12.5% non-denaturing polyacrylamide gel in 0.5×TBE buffer, stained with ethidium-bromide (EtBr) and destained. A 36-base pair internal control for amplification efficiency and quantitative analysis was run for each reaction as indicated by the arrow (FIG. 17).

As shown in FIG. 17, the combined treatment of CP-Nanog and CP-Oct4 recombinant proteins induced high level of telomerase activity. At Day 3, the telomerase activity in the cells treated with combined CP-Nanog and CP-Oct4 recombinant proteins was significantly increased, as compared with that of the cells having no treatment at Day 3 (At Day 3, since the cells treated with control proteins (HN+HO) were very sick and easily died, cell extracts could not be prepared enough for analysis). The high telomerase activity in the cells treated with combined CP-Nanog and CP-Oct4 recombinant proteins suggests that such a combined treatment increase replicative life-span of the cells.

The present invention has been described in detail with reference to specific embodiments thereof. However, it will be appreciated by those skilled in the art that changes may be made in these embodiments without departing from the principles and spirit of the invention, the scope of which is defined in the appended claims and their equivalents.

The invention claimed is:

1. An isolated cell permeable Nanog recombinant protein comprising a kaposi fibroblast growth factor 4 (kFGF4)-derived macromolecule transduction domain (MTD) and a human transcription factor Nanog, said kFGF4-derived MTD being fused to N-terminus and/or C-terminus of the human Nanog protein.

2. The isolated recombinant protein Nanog according to claim 1, wherein the kFGF4-derived MTD has an amino acid sequence represented by SEQ ID NO: 8.

3. The isolated cell permeable Nanog recombinant protein according to claim 1, wherein the human transcription factor Nanog is in a full-length form having an amino acid sequence represented by SEQ ID NO: 2 which includes all of an N-terminal domain, a homeodomain and a tryptophan repeat, or a truncated form lacking one or more of the N-terminal domain, homeodomain and tryptophan repeat.

4. The isolated cell permeable Nanog recombinant protein according to claim 1, which further comprises a nuclear localization sequence (NLS), said nuclear localization sequence being covalently coupled to one end of the recombinant protein.

5. The isolated cell permeable Nanog recombinant protein according to claim 4, wherein the nuclear localization sequence has an amino acid sequence represented by SEQ ID NO: 6.

6. The isolated cell permeable Nanog recombinant protein according to claim 1, which further comprises a histidine-tag (His-Tag) affinity domain, said histidine-tag affinity domain being covalently coupled to the N-terminus of the recombinant protein.

7. The isolated cell permeable Nanog recombinant protein according to claim 1, which is a recombinant protein selected from the group consisting of:

His-MTD-Nanog (HMN) wherein a kFGF4-derived MTD is fused to the N-terminus of a full-length Nanog, His-Nanog-MTD (HNM) wherein a kFGF4-derived MTD is fused to the C-terminus of a full-length Nanog, His-MTD-Nanog-MTD (HMNM) wherein a kFGF4-derived MTD is fused to both termini of a full-length Nanog, His-Nanog N-terminal-MTD (HNNM) wherein a kFGF4-derived MTD is fused to the C-terminus of a Nanog N-terminal domain fragment lacking a homeodomain and a tryptophan repeat, His-Nanog homeodomain-MTD (HNHM) wherein a kFGF4-derived MTD is fused to the C-terminus of a Nanog homeodomain fragment lacking N-terminal and C-terminal domains, His-Nanog C-terminal MTD (HNCM) wherein a kFGF4-derived MTD is fused to C-terminus of a Nanog C-terminal domain lacking an N-terminal domain and a homeodomain, His-Nanog N-terminal-homeodomain-MTD (HNNHM) wherein a kFGF4-derived MTD is fused to the C-terminus of a Nanog N-terminal domain and homeodomain fragment lacking a C-terminal domain, and His-Nanog homeodomain-C-terminal-MTD (HNHCM) wherein a kFGF4-derived MTD is fused to the C-terminus of a Nanog homeodomain and C-terminal domain fragment lacking an N-terminal domain, wherein a His-tag and a NLS derived from SV40 large T antigen are covalently coupled to the N-terminus of all recombinant proteins.

8. The isolated cell permeable Nanog recombinant protein according to claim 7, wherein
His-MTD-Nanog (HMN) has an amino acid sequence represented by SEQ ID NO: 19;
His-Nanog-MTD (HNM) has an amino acid sequence represented by SEQ ID NO: 20;
His-MTD-Nanog-MTD (HMNM) has an amino acid sequence represented by SEQ ID NO: 21;
His-Nanog N-terminal-MTD (HNNM) has an amino acid sequence represented by SEQ ID NO: 22;
His-Nanog homeodomain-MTD (HNHM) has an amino acid sequence represented by SEQ ID NO: 23;
His-Nanog C-terminal MTD (HNCM) has an amino acid sequence represented by SEQ ID NO: 24;
His-Nanog N-terminal-homeodomain-MTD (HNNHM) has an amino acid sequence represented by SEQ ID NO: 25; and
His-Nanog homeodomain-C-terminal-MTD (HNHCM) has an amino acid sequence represented by SEQ ID NO: 26.

9. An isolated polynucleotide encoding the cell permeable Nanog recombinant protein according to claim 1.

10. The isolated polynucleotide according to claim 9, which has a nucleotide sequence selected from the group consisting of SEQ ID NOS: 10 to 17.

11. An expression vector containing the polynucleotide according to claim 9.

12. The expression vector according to claim 11, which is pET28a(+)-HNM (Accession NO: KCTC 11278BP).

13. An expression vector containing the polynucleotide according to claim 10.

14. A transformant capable of producing a cell permeable Nanog recombinant protein at high levels which is obtained by transforming a host cell using the expression vector according to claim 11.

15. A method of producing the cell permeable Nanog recombinant protein at high levels which comprises culturing the transformant according to claim 14.

16. An isolated cell permeable Oct4 recombinant protein comprising a kaposi fibroblast growth factor 4 (kFGF4)-derived macromolecule transduction domain (MTD) peptide and a human transcription factor Oct4, said kFGF4-derived MTD being fused to N-terminus and/or C-terminus of the human Oct4 protein.

17. The isolated cell permeable Oct4 recombinant protein according to claim 16, wherein the kFGF4-derived MTD has an amino acid sequence represented by SEQ ID NO: 8.

18. The isolated cell permeable Oct4 recombinant protein according to claim 16, wherein the human transcription factor Oct4 is in a full-length form having an amino acid sequence represented by SEQ ID NO: 4 which includes all of a proline rich region, a POU specific domain and a homeodomain, or a truncated form lacking one or more of the proline rich region, POU specific domain and homeodomain.

19. The isolated cell permeable Oct4 recombinant protein according to claim 16, which further comprises a nuclear localization sequence (NLS), said nuclear localization sequence being covalently coupled to the N-terminus of the recombinant protein.

20. The isolated cell permeable Oct4 recombinant protein according to claim 19, wherein the nuclear localization sequence has an amino acid sequence represented by SEQ ID NO: 6.

21. The isolated cell permeable Oct4 recombinant protein according to claim 16, which further comprises a histidine-tag (His-Tag) affinity domain, said histidine-tag affinity domain being covalently coupled to one end of the recombinant protein.

22. The isolated cell permeable Oct4 recombinant protein according to claim 16, which is a recombinant protein selected from the group consisting of:
His-MTD-Oct4 (HMO) wherein a kFGF4-derived MTD is fused to the N-terminus of a full-length Oct4,
His-Oct4-MTD (HOM) wherein a kFGF4-derived MTD is fused to the C-terminus of a full-length Oct4, and
His-MTD-Oct4-MTD (HMOM) wherein a kFGF4-derived MTD is fused to both termini of a full-length Oct4,
wherein a His-tag and a NLS derived from SV40 large T antigen are covalently coupled to the N-terminus of all recombinant proteins.

23. The isolated cell permeable Oct4 recombinant protein according to claim 22, wherein
His-MTD-Oct4 (HMO) has an amino acid sequence represented by SEQ ID NO: 32;
His-Oct4-MTD (HOM) has an amino acid sequence represented by SEQ ID NO: 33; and
His-MTD-Oct4-MTD (HMOM) has an amino acid sequence represented by SEQ ID NO: 34.

24. An isolated polynucleotide encoding the cell permeable Oct4 recombinant protein according to claim 16.

25. The isolated polynucleotide according to claim 24, which has a nucleotide sequence selected from the group consisting of SEQ ID NOS: 28 to 30.

26. An expression vector containing the polynucleotide according to claim 24.

27. The expression vector according to claim 26, which is pET28a(+)-HMO (Accession NO: KCTC 11279BP), pET28a(+)-HOM (Accession NO: KCTC 11280BP) or pET28a(+)-HMOM (Accession NO: KCTC 11281BP).

28. An expression vector containing the polynucleotide according to claim 25.

29. A transformant capable of producing a cell permeable Oct4 recombinant protein at high levels which is obtained by transforming a host cell using the expression vector according to claim 26.

30. A method of producing the cell permeable Oct4 recombinant protein at high levels which comprises culturing the transformant according to claim 29.

31. A method of increasing self-renewal and suppressing differentiation of stem cells which comprises the step of treating the stem cells in combination with the cell permeable Nanog recombinant protein comprising a Kaposi fibroblast growth factor 4 (kFGF4)-derived macromolecule transduction domain (MTD) and a human transcription factor Nanog, said kFGF4-derived MTD being fused to N-terminus and/or C-terminus of the human Nanog protein and cell permeable Oct4 recombinant protein comprising a Kaposi fibroblast growth factor 4 (kFGF4)-derived macromolecule transduction domain (MTD) peptide and a human transcription factor Oct4, said kFGF4-derived MTD being fused to N-terminus and/or C-terminus of the human Oct4 protein.

32. The method according to claim 31, wherein the stem cell is an adult stem cell, a placenta stem cell, a fetal stem cells or an umbilical stem cell.

33. The method according to claim 31, wherein the stem cell is an embryonic stem (ES) cell, an embryonic carcinoma (EC) cell or an embryonic germ (EG) cell.

* * * * *

SEQUENCE LISTING

<160> NUMBER OF SEQ ID NOS: 47

<210> SEQ ID NO 1
<211> LENGTH: 918
<212> TYPE: DNA
<213> ORGANISM: Homo sapiens

<400> SEQUENCE: 1

```
atgagtgtgg atccagcttg tccccaaagc ttgccttgct ttgaagcatc cgactgtaaa      60
gaatcttcac ctatgcctgt gatttgtggg cctgaagaaa actatccatc cttgcaaatg     120
tcttctgctg agatgcctca cacggagact gtctctcctc ttccctcctc catggatctg     180
cttattcagg acagccctga ttcttccacc agtcccaaag caaacaacc cacttctgca      240
gagaatagtg tcgcaaaaaa ggaagacaag gtcccagtca agaaacagaa gaccagaact     300
gtgttctctt ccacccagct gtgtgtactc aatgatagat tcagagaca gaaatacctc      360
agcctccagc agatgcaaga actctccaac atcctgaacc tcagctacaa acaggtgaag     420
acctggttcc agaaccagag aatgaaatct aagaggtggc agaaaaacaa ctggccgaag     480
aatagcaatg gtgtgacgca gaaggcctca gcacctacct accccagcct ctactcttcc     540
taccaccagg gatgcctggt gaacccgact gggaaccttc aatgtggag caaccagacc       600
tggaacaatt caacctggag caaccagacc cagaacatcc agtcctggag caaccactcc     660
tggaacactc agacctggtg cacccaatcc tggaacaatc aggcctggaa cagtcccttc     720
tataactgtg gagaggaatc tctgcagtcc tgcatgcagt ccagccaaa ttctcctgcc      780
agtgacttgg aggctgcttt ggaagctgct ggggaaggcc ttaatgtaat acagcagacc     840
actaggtatt ttagtactcc acaaaccatg gatttattcc taaactactc catgaacatg     900
caacctgaag acgtgtga                                                    918
```

<210> SEQ ID NO 2
<211> LENGTH: 305
<212> TYPE: PRT
<213> ORGANISM: Homo sapiens

<400> SEQUENCE: 2

Met Ser Val Asp Pro Ala Cys Pro Gln Ser Leu Pro Cys Phe Glu Ala
1               5                   10                  15

Ser Asp Cys Lys Glu Ser Ser Pro Met Pro Val Ile Cys Gly Pro Glu
            20                  25                  30

Glu Asn Tyr Pro Ser Leu Gln Met Ser Ser Ala Glu Met Pro His Thr
        35                  40                  45

Glu Thr Val Ser Pro Leu Pro Ser Ser Met Asp Leu Leu Ile Gln Asp
    50                  55                  60

Ser Pro Asp Ser Ser Thr Ser Pro Lys Gly Lys Gln Pro Thr Ser Ala
65                  70                  75                  80

Glu Asn Ser Val Ala Lys Lys Glu Asp Lys Val Pro Val Lys Lys Gln
                85                  90                  95

Lys Thr Arg Thr Val Phe Ser Ser Thr Gln Leu Cys Val Leu Asn Asp
            100                 105                 110

Arg Phe Gln Arg Gln Lys Tyr Leu Ser Leu Gln Met Gln Glu Leu
        115                 120                 125

Ser Asn Ile Leu Asn Leu Ser Tyr Lys Gln Val Lys Thr Trp Phe Gln
    130                 135                 140

Asn Gln Arg Met Lys Ser Lys Arg Trp Gln Lys Asn Asn Trp Pro Lys

```
                145                 150                 155                 160
Asn Ser Asn Gly Val Thr Gln Lys Ala Ser Ala Pro Thr Tyr Pro Ser
                    165                 170                 175

Leu Tyr Ser Ser Tyr His Gln Gly Cys Leu Val Asn Pro Thr Gly Asn
                    180                 185                 190

Leu Pro Met Trp Ser Asn Gln Thr Trp Asn Asn Ser Thr Trp Ser Asn
                    195                 200                 205

Gln Thr Gln Asn Ile Gln Ser Trp Ser Asn His Ser Trp Asn Thr Gln
                    210                 215                 220

Thr Trp Cys Thr Gln Ser Trp Asn Asn Gln Ala Trp Asn Ser Pro Phe
225                 230                 235                 240

Tyr Asn Cys Gly Glu Glu Ser Leu Gln Ser Cys Met Gln Phe Gln Pro
                    245                 250                 255

Asn Ser Pro Ala Ser Asp Leu Glu Ala Ala Leu Glu Ala Ala Gly Glu
                    260                 265                 270

Gly Leu Asn Val Ile Gln Gln Thr Thr Arg Tyr Phe Ser Thr Pro Gln
                    275                 280                 285

Thr Met Asp Leu Phe Leu Asn Tyr Ser Met Asn Met Gln Pro Glu Asp
                    290                 295                 300

Val
305

<210> SEQ ID NO 3
<211> LENGTH: 1083
<212> TYPE: DNA
<213> ORGANISM: Homo sapiens

<400> SEQUENCE: 3
atggcgggac acctggcttc ggatttcgcc ttctcgcccc ctccaggtgg tggaggtgat      60
gggccagggg ggccggagcc gggctgggtt gatcctcgga cctggctaag cttccaaggc     120
cctcctggag ggccaggaat cgggccgggg gttgggccag ctctgaggt gtggggga tt     180 cccccatgcc ccccgccgta tgagttctgt gggggga tgg cgtactgtgg ccccaggtt     240 ggagtggggc tagtgcccca aggcggcttg agacctctc agcctgaggg cgaagcagga     300
gtcggggtgg agagcaactc cgatggggcc tccccggagc cctgcaccgt caccctggt     360 gccgtgaagc tggagaagga gaagctggag caaaacccgg aggagtccca ggacatcaaa     420
gctctgcaga agaactcga gcaatttgcc aagctcctga gcagaagag gatcaccctg      480 ggatataca ggccgatgt ggggctcacc ctgggggtt c tatttgggaa ggtattcagc      540
caaacgacca tctgccgctt tgaggctctg cagcttagct tcaagaacat tgtgtaagctg    600 cggcccttgc tgcagaagtg ggtggaggaa gctgacaaca tgaaaatctt tcaggagata    660
tgcaaagcag aaaccctcgt gcaggcccga agagaaagc gaaccagtat cgagaaccga    720
gtgagaggca acctggagaa tttgttcctg cagtgcccga aacccacact gcagcagatc    780
agccacatcg cccagcagct tgggctcgag aaggatgtgg tccgagtgtg gttctgtaac    840
cggcgccaga agggcaagcg atcaagcagc gactatgcac aacgagagga ttttgaggct    900
gctgggtctc ctttctcagg gggaccagtg tcctttcctc tggccccagg ccccattttt    960
ggtaccccag gctatgggag ccctcacttc actgcactgt actcctcggt ccctttccct   1020 gaggggaag cctttccccc tgtctccgtc accactctgg gctctcccat gcattcaaac   1080
tga                                                                 1083

<210> SEQ ID NO 4
```

```
<211> LENGTH: 360
<212> TYPE: PRT
<213> ORGANISM: Homo sapiens

<400> SEQUENCE: 4

Met Ala Gly His Leu Ala Ser Asp Phe Ala Phe Ser Pro Pro Pro Gly
1               5                   10                  15

Gly Gly Gly Asp Gly Pro Gly Pro Glu Pro Gly Trp Val Asp Pro
            20                  25                  30

Arg Thr Trp Leu Ser Phe Gln Gly Pro Pro Gly Gly Pro Gly Ile Gly
        35                  40                  45

Pro Gly Val Gly Pro Gly Ser Glu Val Trp Gly Ile Pro Pro Cys Pro
50                  55                  60

Pro Pro Tyr Glu Phe Cys Gly Gly Met Ala Tyr Cys Gly Pro Gln Val
65              70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
        115                 120                 125

Leu Glu Gln Asn Pro Glu Glu Ser Gln Asp Ile Lys Ala Leu Gln Lys
130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
        195                 200                 205

Glu Glu Ala Asp Asn Asn Glu Asn Leu Gln Glu Ile Cys Lys Ala Glu
210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
        275                 280                 285

Ser Ser Asp Tyr Ala Gln Arg Glu Asp Phe Glu Ala Ala Gly Ser Pro
290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn
        355                 360

<210> SEQ ID NO 5
<211> LENGTH: 15
<212> TYPE: DNA
<213> ORGANISM: Unknown
```

```
<220> FEATURE:
<223> OTHER INFORMATION: Description of Unknown: SV40 Large T
      Antigen-derived NLS oligonucleotide

<400> SEQUENCE: 5
aagaagaaga ggaag                                                          15

<210> SEQ ID NO 6
<211> LENGTH: 5
<212> TYPE: PRT
<213> ORGANISM: Unknown
<220> FEATURE:
<223> OTHER INFORMATION: Description of Unknown: SV40 Large T
      Antigen-derived NLS oligonucleotide

<400> SEQUENCE: 6

Lys Lys Lys Arg Lys
1               5

<210> SEQ ID NO 7
<211> LENGTH: 36
<212> TYPE: DNA
<213> ORGANISM: Unknown
<220> FEATURE:
<223> OTHER INFORMATION: Description of Unknown: kFGF4-Derived MTD
      peptide

<400> SEQUENCE: 7
gcagccgttc ttctccctgt tcttcttgcc gcaccc                                   36

<210> SEQ ID NO 8
<211> LENGTH: 12
<212> TYPE: PRT
<213> ORGANISM: Unknown
<220> FEATURE:
<223> OTHER INFORMATION: Description of Unknown: kFGF4-Derived MTD
      peptide

<400> SEQUENCE: 8

Ala Ala Val Leu Leu Pro Val Leu Leu Ala Ala Pro
1               5                   10

<210> SEQ ID NO 9
<211> LENGTH: 993
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
atgggcagca gccatcatca tcatcatcac agcagcggcc tggtgccgcg cggcagccat          60
atgaagaaga agaggaagag tgtggatcca gcttgtcccc aaagcttgcc ttgctttgaa         120
gcatccgact gtaaagaatc ttcacctatg cctgtgattt gtgggcctga agaaaactat         180
ccatccttgc aaatgtcttc tgctgagatg cctcacacgg agactgtctc tcctcttccc         240
tcctccatgg atctgcttat tcaggacagc cctgattctt ccaccagtcc aaaggcaaa          300 caacccactt ctgcagagaa tagtgtcgca aaaaaggaag acaaggtccc agtcaagaaa         360
cagaagacca gaactgtgtt ctcttccacc agctgtgtg tactcaatga tagatttcag         420
agacagaaat acctcagcct ccagcagatg caagaactct ccaacatcct gaacctcagc         480
tacaaacagg tgaagacctg gttccagaac cagagaatga aatctaagag gtggcagaaa         540
aacaactggc cgaagaatag caatggtgtg acgcagaagg cctcagcacc tacctacccc         600
```

```
agcctctact cttcctacca ccagggatgc ctggtgaacc cgactgggaa ccttccaatg    660
tggagcaacc agacctggaa caattcaacc tggagcaacc agacccagaa catccagtcc    720
tggagcaacc actcctggaa cactcagacc tggtgcaccc aatcctggaa caatcaggcc    780
tggaacagtc ccttctataa ctgtggagag gaatctctgc agtcctgcat gcagttccag    840
ccaaattctc ctgccagtga cttggaggct gctttggaag ctgctgggga aggccttaat    900
gtaatacagc agaccactag gtattttagt actccacaaa ccatggattt attcctaaac    960
tactccatga acatgcaacc tgaagacgtg tga                                 993

<210> SEQ ID NO 10
<211> LENGTH: 1028
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
atgggcagca gccatcatca tcatcatcac agcagcggcc tggtgccgcg cggcagccat     60
atgaagaaga agaggaaggc agccgttctt ctccctgttc ttcttgccgc acccagtgtg    120
gatccagctt gtccccaaag cttgccttgc tttgaagcat ccgactgtaa agaatcttca    180
cctatgcctg tgatttgtgg gcctgaagaa aactatccat ccttgcaaat gtcttctgct    240
gagatgcctc acacggagac tgtctctcct cttccctcct ccatggatct gcttattcag    300
gacagccctg attcttccac cagtcccaaa ggcaaacaac ccacttctgc agagaatagt    360
gtcgcaaaaa aggaagacaa ggtcccagtc aagaaacaga agaccagaac tgtgttctct    420
tccacccagc tgtgtgtact caatgataga tttcagagac agaaatacct cagcctccag    480
cagatgcaag aactctccaa catcctgaac ctcagctaca aacaggtgaa gacctggttc    540
cagaaccaga gaatgaaatc taagaggtgg cagaaaaaca ctggccgaa gaatagcaat    600 ggtgtgacgc agaaggcctc agcacctacc taccccagcc tctactcttc ctaccaccag    660
ggatgcctgg tgaacccgac tgggaacctt ccaatgtgga gcaaccagac ctggaacaat    720
tcaacctgga gcaaccagac ccagaacatc cagtcctgga gcaaccactc ctggaacact    780
cagacctggt gcacccaatc ctggaacaat caggcctgga acagtccctt ctataactgt    840
ggagaggaat ctctgcagtc ctgcatgcag ttccagccaa attctcctgc cagtgacttg    900
gaggctgctt tggaagctgc tggggaaggc cttaatgtaa tacagcagac cactaggtat    960
tttagtactc cacaaaccat ggatttattc ctaaactact ccatgaacat gcaacctgaa   1020
gacgtgtg                                                           1028

<210> SEQ ID NO 11
<211> LENGTH: 1029
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
atgggcagca gccatcatca tcatcatcac agcagcggcc tggtgccgcg cggcagccat     60
atgaagaaga agaggaagag tgtggatcca gcttgtcccc aaagcttgcc ttgctttgaa    120
gcatccgact gtaaagaatc ttcacctatg cctgtgattt gtgggcctga agaaaactat    180
ccatccttgc aaatgtcttc tgctgagatg cctcacacgg agactgtctc tcctcttccc    240
```

```
tcctccatgg atctgcttat tcaggacagc cctgattctt ccaccagtcc caaaggcaaa      300
caacccactt ctgcagagaa tagtgtcgca aaaaaggaag acaaggtccc agtcaagaaa      360
cagaagacca gaactgtgtt ctcttccacc cagctgtgtg tactcaatga tagatttcag      420
agacagaaat acctcagcct ccagcagatg caagaactct ccaacatcct gaacctcagc      480
tacaaacagg tgaagacctg gttccagaac agagaatga aatctaagag gtggcagaaa       540
```

```
aacaactggc cgaagaatag caatggtgtg acgcagaagg cctcagcacc tacctacccc      600
agcctctact cttcctacca ccagggatgc ctggtgaacc cgactgggaa ccttccaatg      660
tggagcaacc agacctggaa caattcaacc tggagcaacc agacccagaa catccagtcc      720
tggagcaacc actcctggaa cactcagacc tggtgcaccc aatcctggaa caatcaggcc      780
tggaacagtc ccttctataa ctgtggagag aatctctgc agtcctgcat gcagttccag       840
```

```
ccaaattctc ctgccagtga cttggaggct gctttggaag ctgctgggga aggccttaat      900
gtaatacagc agaccactag gtattttagt actccacaaa ccatggattt attcctaaac      960
tactccatga acatgcaacc tgaagacgtg gcagccgttc ttctccctgt tcttcttgcc     1020
gcaccctga                                                             1029
```

<210> SEQ ID NO 12
<211> LENGTH: 1065
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
atgggcagca gccatcatca tcatcatcac agcagcggcc tggtgccgcg cggcagccat       60
atgaagaaga gaggaaggc agccgttctt ctccctgttc ttcttgccgc acccagtgtg      120
gatccagctt gtccccaaag cttgccttgc tttgaagcat ccgactgtaa agaatcttca      180
cctatgcctg tgatttgtgg gcctgaagaa actatccat ccttgcaaat gtcttctgct       240
gagatgcctc acacggagac tgtctctcct cttccctcct ccatggatct gcttattcag      300
gacagccctg attcttccac cagtcccaaa ggcaaacaac ccacttctgc agagaatagt      360
gtcgcaaaaa aggaagacaa ggtcccagtc aagaaacaga agaccagaac tgtgttctct     420
tccacccagc tgtgtgtact caatgataga tttcagagac agaaatacct cagcctccag      480
cagatgcaag aactctccaa catcctgaac ctcagctaca acaggtgaa gacctggttc       540
```

```
cagaaccaga gaatgaaatc taagaggtgg cagaaaaaca ctggccgaa gaatagcaat        600 ggtgtgacgc agaaggcctc agcacctacc taccccagcc tctactcttc ctaccaccag      660
ggatgcctgg tgaacccgac tgggaacctt ccaatgtgga gcaaccagac ctggaacaat      720
tcaacctgga gcaaccagac ccagaacatc cagtcctgga gcaaccactc ctggaacact      780
cagacctggt gcacccaatc ctggaacaat caggcctgga acagtccctt ctataactgt      840
ggagaggaat ctctgcagtc ctgcatgcag ttccagccaa attctcctgc cagtgacttg      900
gaggctgctt tggaagctgc tggggaaggc cttaatgtaa tacagcagac cactaggtat      960
tttagtactc cacaaaccat ggatttattc ctaaactact ccatgaacat gcaacctgaa     1020
gacgtggcag ccgttcttct ccctgttctt cttgccgcac cctga                     1065
```

<210> SEQ ID NO 13
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

| | | | | | |
|---|---|---|---|---|---|
| atgggcagca | gccatcatca | tcatcatcac | agcagcggcc | tggtgccgcg | cggcagccat | 60 |
| atgaagaaga | agaggaagag | tgtggatcca | gcttgtcccc | aaagcttgcc | ttgctttgaa | 120 |
| gcatccgact | gtaaagaatc | ttcacctatg | cctgtgattt | gtgggcctga | agaaaactat | 180 |
| ccatccttgc | aaatgtcttc | tgctgagatg | cctcacacgg | agactgtctc | tcctcttccc | 240 |
| tcctccatgg | atctgcttat | tcaggacagc | cctgattctt | ccaccagtcc | caaaggcaaa | 300 |
| caacccactt | ctgcagagaa | tagtgtcgca | aaaaaggaag | acaaggtccc | agtcaagaaa | 360 |
| gcagccgttc | ttctccctgt | tcttcttgcc | gcaccctga | | | 399 |

<210> SEQ ID NO 14
<211> LENGTH: 297
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

| | | | | | |
|---|---|---|---|---|---|
| atgggcagca | gccatcatca | tcatcatcac | agcagcggcc | tggtgccgcg | cggcagccat | 60 |
| atgaagaaga | agaggaagca | gaagaccaga | actgtgttct | cttccaccca | gctgtgtgta | 120 |
| ctcaatgata | gatttcagag | acagaaatac | ctcagcctcc | agcagatgca | agaactctcc | 180 |
| aacatcctga | acctcagcta | caaacaggtg | aagacctggt | tccagaacca | gagaatgaaa | 240 |
| tctaagaggt | ggcagaaagc | agccgttctt | ctccctgttc | ttcttgccgc | accctga | 297 |

<210> SEQ ID NO 15
<211> LENGTH: 567
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

| | | | | | |
|---|---|---|---|---|---|
| atgggcagca | gccatcatca | tcatcatcac | agcagcggcc | tggtgccgcg | cggcagccat | 60 |
| atgaagaaga | agaggaagaa | caactggccg | aagaatagca | atggtgtgac | gcagaaggcc | 120 |
| tcagcaccta | cctaccccag | cctctactct | tcctaccacc | agggatgcct | ggtgaacccg | 180 |
| actgggaacc | ttccaatgtg | gagcaaccag | acctggaaca | attcaacctg | gagcaaccag | 240 |
| acccagaaca | tccagtcctg | gagcaaccac | tcctggaaca | ctcagacctg | gtgcaccccaa | 300 |
| tcctggaaca | atcaggcctg | gaacagtccc | ttctataact | gtggagagga | atctctgcag | 360 |
| tcctgcatgc | agttccagcc | aaattctcct | gccagtgact | tggaggctgc | tttggaagct | 420 |
| gctggggaag | gccttaatgt | aatacagcag | accactaggt | attttagtac | tccacaaacc | 480 |
| atggatttat | tcctaaacta | ctccatgaac | atgcaacctg | aagacgtggc | agccgttctt | 540 |
| ctccctgttc | ttcttgccgc | accctga | | | | 567 |

<210> SEQ ID NO 16
<211> LENGTH: 579
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
atgggcagca gccatcatca tcatcatcac agcagcggcc tggtgccgcg cggcagccat      60
atgaagaaga agaggaagag tgtggatcca gcttgtcccc aaagcttgcc ttgctttgaa     120
gcatccgact gtaaagaatc ttcacctatg cctgtgattt gtgggcctga agaaaactat     180
ccatccttgc aaatgtcttc tgctgagatg cctcacacgg agactgtctc tcctcttccc     240
tcctccatgg atctgcttat tcaggacagc cctgattctt ccaccagtcc caaaggcaaa     300
caacccactt ctgcagagaa tagtgtcgca aaaaaggaag acaaggtccc agtcaagaaa     360
cagaagacca gaactgtgtt ctcttccacc agctgtgtg tactcaatga tagatttcag      420
agacagaaat acctcagcct ccagcagatg caagaactct ccaacatcct gaacctcagc     480
tacaaacagg tgaagacctg gttccagaac cagagaatga atctaagag gtggcagaaa      540
gcagccgttc ttctccctgt tcttcttgcc gcaccctga                            579
```

<210> SEQ ID NO 17
<211> LENGTH: 747
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
atgggcagca gccatcatca tcatcatcac agcagcggcc tggtgccgcg cggcagccat      60
atgaagaaga agaggaagca gaagaccaga actgtgttct cttccaccca gctgtgtgta     120
ctcaatgata gatttcagag acagaaatac ctcagcctcc agcagatgca agaactctcc     180
aacatcctga acctcagcta caaacaggtg aagacctggt tccagaacca gagaatgaaa     240
tctaagaggt ggcagaaaaa caactggccg aagaatagca atggtgtgac gcagaaggcc     300
tcagcaccta cctaccccag cctctactct tcctaccacc agggatgcct ggtgaacccg     360
actgggaacc ttccaatgtg gagcaaccag acctggaaca attcaacctg gagcaaccag     420
acccagaaca tccagtcctg gagcaaccac tcctggaaca ctcagacctg gtgcacccaa     480
tcctggaaca tcaggcctg gaacagtccc ttctataact gtggagagga atctctgcag      540
tcctgcatgc agttccagcc aaattctcct gccagtgact ggaggctgc tttggaagct      600
gctggggaag gccttaatgt aatacagcag accactaggt attttagtac tccacaaacc     660
atggatttat tcctaaacta ctccatgaac atgcaacctg aagacgtggc agccgttctt     720
ctccctgttc ttcttgccgc accctga                                         747
```

<210> SEQ ID NO 18
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

```
Met Gly Ser Ser His His His His His His Ser Ser Gly Leu Val Pro
1               5                   10                  15

Arg Gly Ser His Met Lys Lys Lys Arg Lys Ser Val Asp Pro Ala Cys
            20                  25                  30

Pro Gln Ser Leu Pro Cys Phe Glu Ala Ser Asp Cys Lys Glu Ser Ser
        35                  40                  45
```

```
Pro Met Pro Val Ile Cys Gly Pro Glu Glu Asn Tyr Pro Ser Leu Gln
    50              55                  60
Met Ser Ser Ala Glu Met Pro His Thr Glu Thr Val Ser Pro Leu Pro
 65              70                  75                  80
Ser Ser Met Asp Leu Leu Ile Gln Asp Ser Pro Asp Ser Ser Thr Ser
                 85                  90                  95
Pro Lys Gly Lys Gln Pro Thr Ser Ala Glu Asn Ser Val Ala Lys Lys
                100                 105                 110
Glu Asp Lys Val Pro Val Lys Lys Gln Lys Thr Arg Thr Val Phe Ser
            115                 120                 125
Ser Thr Gln Leu Cys Val Leu Asn Asp Arg Phe Gln Arg Gln Lys Tyr
    130                 135                 140
Leu Ser Leu Gln Gln Met Gln Glu Leu Ser Asn Ile Leu Asn Leu Ser
145                 150                 155                 160
Tyr Lys Gln Val Lys Thr Trp Phe Gln Asn Gln Arg Met Lys Ser Lys
                165                 170                 175
Arg Trp Gln Lys Asn Asn Trp Pro Lys Asn Ser Asn Gly Val Thr Gln
                180                 185                 190
Lys Ala Ser Ala Pro Thr Tyr Pro Ser Leu Tyr Ser Ser Tyr His Gln
            195                 200                 205
Gly Cys Leu Val Asn Pro Thr Gly Asn Leu Pro Met Trp Ser Asn Gln
    210                 215                 220
Thr Trp Asn Asn Ser Thr Trp Ser Asn Gln Thr Gln Asn Ile Gln Ser
225                 230                 235                 240
Trp Ser Asn His Ser Trp Asn Thr Gln Thr Trp Cys Thr Gln Ser Trp
                245                 250                 255
Asn Asn Gln Ala Trp Asn Ser Pro Phe Tyr Asn Cys Gly Glu Glu Ser
                260                 265                 270
Leu Gln Ser Cys Met Gln Phe Gln Pro Asn Ser Pro Ala Ser Asp Leu
            275                 280                 285
Glu Ala Ala Leu Glu Ala Ala Gly Glu Gly Leu Asn Val Ile Gln Gln
            290                 295                 300
Thr Thr Arg Tyr Phe Ser Thr Pro Gln Thr Met Asp Leu Phe Leu Asn
305                 310                 315                 320
Tyr Ser Met Asn Met Gln Pro Glu Asp Val
                325                 330

<210> SEQ ID NO 19
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Gly Ser Ser His His His His His His Ser Ser Gly Leu Val Pro
  1               5                  10                  15
Arg Gly Ser His Met Lys Lys Arg Lys Ala Ala Val Leu Leu Pro
             20                  25                  30
Val Leu Leu Ala Ala Pro Ser Val Asp Pro Ala Cys Pro Gln Ser Leu
                 35                  40                  45
Pro Cys Phe Glu Ala Ser Asp Cys Lys Glu Ser Ser Pro Met Pro Val
    50                  55                  60
Ile Cys Gly Pro Glu Glu Asn Tyr Pro Ser Leu Gln Met Ser Ser Ala
 65                  70                  75                  80
```

```
Glu Met Pro His Thr Glu Thr Val Ser Pro Leu Pro Ser Ser Met Asp
                85                  90                  95

Leu Leu Ile Gln Asp Ser Pro Asp Ser Ser Thr Ser Pro Lys Gly Lys
            100                 105                 110

Gln Pro Thr Ser Ala Glu Asn Ser Val Ala Lys Lys Glu Asp Lys Val
        115                 120                 125

Pro Val Lys Lys Gln Lys Thr Arg Thr Val Phe Ser Ser Thr Gln Leu
    130                 135                 140

Cys Val Leu Asn Asp Arg Phe Gln Arg Gln Lys Tyr Leu Ser Leu Gln
145                 150                 155                 160

Gln Met Gln Glu Leu Ser Asn Ile Leu Asn Leu Ser Tyr Lys Gln Val
                165                 170                 175

Lys Thr Trp Phe Gln Asn Gln Arg Met Lys Ser Lys Arg Trp Gln Lys
            180                 185                 190

Asn Asn Trp Pro Lys Asn Ser Asn Gly Val Thr Gln Lys Ala Ser Ala
        195                 200                 205

Pro Thr Tyr Pro Ser Leu Tyr Ser Ser Tyr His Gln Gly Cys Leu Val
    210                 215                 220

Asn Pro Thr Gly Asn Leu Pro Met Trp Ser Asn Gln Thr Trp Asn Asn
225                 230                 235                 240

Ser Thr Trp Ser Asn Gln Thr Gln Asn Ile Gln Ser Trp Ser Asn His
                245                 250                 255

Ser Trp Asn Thr Gln Thr Trp Cys Thr Gln Ser Trp Asn Asn Gln Ala
            260                 265                 270

Trp Asn Ser Pro Phe Tyr Asn Cys Gly Glu Glu Ser Leu Gln Ser Cys
        275                 280                 285

Met Gln Phe Gln Pro Asn Ser Pro Ala Ser Asp Leu Glu Ala Ala Leu
    290                 295                 300

Glu Ala Ala Gly Glu Gly Leu Asn Val Ile Gln Gln Thr Thr Arg Tyr
305                 310                 315                 320

Phe Ser Thr Pro Gln Thr Met Asp Leu Phe Leu Asn Tyr Ser Met Asn
                325                 330                 335

Met Gln Pro Glu Asp Val
            340

<210> SEQ ID NO 20
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Gly Ser Ser His His His His His His Ser Ser Gly Leu Val Pro
1               5                   10                  15

Arg Gly Ser His Met Lys Lys Arg Lys Ser Val Asp Pro Ala Cys
                20                  25                  30

Pro Gln Ser Leu Pro Cys Phe Glu Ala Ser Asp Cys Lys Glu Ser Ser
            35                  40                  45

Pro Met Pro Val Ile Cys Gly Pro Glu Glu Asn Tyr Pro Ser Leu Gln
        50                  55                  60

Met Ser Ser Ala Glu Met Pro His Thr Glu Thr Val Ser Pro Leu Pro
65                  70                  75                  80

Ser Ser Met Asp Leu Leu Ile Gln Asp Ser Pro Asp Ser Ser Thr Ser
                85                  90                  95
```

```
Pro Lys Gly Lys Gln Pro Thr Ser Ala Glu Asn Ser Val Ala Lys Lys
            100                 105                 110

Glu Asp Lys Val Pro Val Lys Gln Lys Thr Arg Thr Val Phe Ser
            115                 120                 125

Ser Thr Gln Leu Cys Val Leu Asn Asp Arg Phe Gln Arg Gln Lys Tyr
130                 135                 140

Leu Ser Leu Gln Gln Met Gln Glu Leu Ser Asn Ile Leu Asn Leu Ser
145                 150                 155                 160

Tyr Lys Gln Val Lys Thr Trp Phe Gln Asn Gln Arg Met Lys Ser Lys
                165                 170                 175

Arg Trp Gln Lys Asn Asn Trp Pro Lys Asn Ser Asn Gly Val Thr Gln
            180                 185                 190

Lys Ala Ser Ala Pro Thr Tyr Pro Ser Leu Tyr Ser Tyr His Gln
            195                 200                 205

Gly Cys Leu Val Asn Pro Thr Gly Asn Leu Pro Met Trp Ser Asn Gln
            210                 215                 220

Thr Trp Asn Asn Ser Thr Trp Ser Asn Gln Thr Gln Asn Ile Gln Ser
225                 230                 235                 240

Trp Ser Asn His Ser Trp Asn Thr Gln Thr Trp Cys Thr Gln Ser Trp
                245                 250                 255

Asn Asn Gln Ala Trp Asn Ser Pro Phe Tyr Asn Cys Gly Glu Glu Ser
            260                 265                 270

Leu Gln Ser Cys Met Gln Phe Gln Pro Asn Ser Pro Ala Ser Asp Leu
            275                 280                 285

Glu Ala Ala Leu Glu Ala Gly Glu Gly Leu Asn Val Ile Gln Gln
            290                 295                 300

Thr Thr Arg Tyr Phe Ser Thr Pro Gln Thr Met Asp Leu Phe Leu Asn
305                 310                 315                 320

Tyr Ser Met Asn Met Gln Pro Glu Asp Val Ala Ala Val Leu Leu Pro
                325                 330                 335

Val Leu Leu Ala Ala Pro
            340

<210> SEQ ID NO 21
<211> LENGTH: 354
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Gly Ser Ser His His His His His His Ser Ser Gly Leu Val Pro
1               5                   10                  15

Arg Gly Ser His Met Lys Lys Lys Arg Lys Ala Ala Val Leu Leu Pro
            20                  25                  30

Val Leu Leu Ala Ala Pro Ser Val Asp Pro Ala Cys Pro Gln Ser Leu
            35                  40                  45

Pro Cys Phe Glu Ala Ser Asp Cys Lys Glu Ser Ser Pro Met Pro Val
        50                  55                  60

Ile Cys Gly Pro Glu Glu Asn Tyr Pro Ser Leu Gln Met Ser Ser Ala
65                  70                  75                  80

Glu Met Pro His Thr Glu Thr Val Ser Pro Leu Pro Ser Ser Met Asp
                85                  90                  95

Leu Leu Ile Gln Asp Ser Pro Asp Ser Ser Thr Ser Pro Lys Gly Lys
            100                 105                 110
```

```
Gln Pro Thr Ser Ala Glu Asn Ser Val Ala Lys Lys Glu Asp Lys Val
            115                 120                 125

Pro Val Lys Lys Gln Lys Thr Arg Thr Val Phe Ser Thr Gln Leu
130                 135                 140

Cys Val Leu Asn Asp Arg Phe Gln Arg Gln Lys Tyr Leu Ser Leu Gln
145                 150                 155                 160

Gln Met Gln Glu Leu Ser Asn Ile Leu Asn Leu Ser Tyr Lys Gln Val
                165                 170                 175

Lys Thr Trp Phe Gln Asn Gln Arg Met Lys Ser Lys Arg Trp Gln Lys
            180                 185                 190

Asn Asn Trp Pro Lys Asn Ser Asn Gly Val Thr Gln Lys Ala Ser Ala
            195                 200                 205

Pro Thr Tyr Pro Ser Leu Tyr Ser Ser Tyr His Gln Gly Cys Leu Val
            210                 215                 220

Asn Pro Thr Gly Asn Leu Pro Met Trp Ser Asn Gln Thr Trp Asn Asn
225                 230                 235                 240

Ser Thr Trp Ser Asn Gln Thr Gln Asn Ile Gln Ser Trp Ser Asn His
                245                 250                 255

Ser Trp Asn Thr Gln Thr Trp Cys Thr Gln Ser Trp Asn Asn Gln Ala
            260                 265                 270

Trp Asn Ser Pro Phe Tyr Asn Cys Gly Glu Glu Ser Leu Gln Ser Cys
            275                 280                 285

Met Gln Phe Gln Pro Asn Ser Pro Ala Ser Asp Leu Glu Ala Ala Leu
            290                 295                 300

Glu Ala Ala Gly Glu Gly Leu Asn Val Ile Gln Gln Thr Thr Arg Tyr
305                 310                 315                 320

Phe Ser Thr Pro Gln Thr Met Asp Leu Phe Leu Asn Tyr Ser Met Asn
                325                 330                 335

Met Gln Pro Glu Asp Val Ala Ala Val Leu Leu Pro Val Leu Leu Ala
            340                 345                 350

Ala Pro

<210> SEQ ID NO 22
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Gly Ser Ser His His His His His His Ser Ser Gly Leu Val Pro
1               5                   10                  15

Arg Gly Ser His Met Lys Lys Arg Lys Ser Val Asp Pro Ala Cys
            20                  25                  30

Pro Gln Ser Leu Pro Cys Phe Glu Ala Ser Asp Cys Lys Glu Ser Ser
            35                  40                  45

Pro Met Pro Val Ile Cys Gly Pro Glu Glu Asn Tyr Pro Ser Leu Gln
    50                  55                  60

Met Ser Ser Ala Glu Met Pro His Thr Glu Thr Val Ser Pro Leu Pro
65                  70                  75                  80

Ser Ser Met Asp Leu Leu Ile Gln Asp Ser Pro Asp Ser Ser Thr Ser
                85                  90                  95

Pro Lys Gly Lys Gln Pro Thr Ser Ala Glu Asn Ser Val Ala Lys Lys
            100                 105                 110

Glu Asp Lys Val Pro Val Lys Lys Ala Ala Val Leu Leu Pro Val Leu
```

Leu Ala Ala Pro
    130

<210> SEQ ID NO 23
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Gly Ser Ser His His His His His Ser Ser Gly Leu Val Pro
1               5                   10                  15

Arg Gly Ser His Met Lys Lys Arg Lys Gln Lys Thr Arg Thr Val
                20                  25                  30

Phe Ser Ser Thr Gln Leu Cys Val Leu Asn Asp Arg Phe Gln Arg Gln
                35                  40                  45

Lys Tyr Leu Ser Leu Gln Gln Met Gln Glu Leu Ser Asn Ile Leu Asn
50                  55                  60

Leu Ser Tyr Lys Gln Val Lys Thr Trp Phe Gln Asn Gln Arg Met Lys
65                  70                  75                  80

Ser Lys Arg Trp Gln Lys Ala Ala Val Leu Leu Pro Val Leu Leu Ala
                85                  90                  95

Ala Pro

<210> SEQ ID NO 24
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Gly Ser Ser His His His His His Ser Ser Gly Leu Val Pro
1               5                   10                  15

Arg Gly Ser His Met Lys Lys Arg Lys Asn Asn Trp Pro Lys Asn
                20                  25                  30

Ser Asn Gly Val Thr Gln Lys Ala Ser Ala Pro Thr Tyr Pro Ser Leu
                35                  40                  45

Tyr Ser Ser Tyr His Gln Gly Cys Leu Val Asn Pro Thr Gly Asn Leu
50                  55                  60

Pro Met Trp Ser Asn Gln Thr Trp Asn Asn Ser Thr Trp Ser Asn Gln
65                  70                  75                  80

Thr Gln Asn Ile Gln Ser Trp Ser Asn His Ser Trp Asn Thr Gln Thr
                85                  90                  95

Trp Cys Thr Gln Ser Trp Asn Asn Gln Ala Trp Asn Ser Pro Phe Tyr
                100                 105                 110

Asn Cys Gly Glu Glu Ser Leu Gln Ser Cys Met Gln Phe Gln Pro Asn
                115                 120                 125

Ser Pro Ala Ser Asp Leu Glu Ala Ala Leu Glu Ala Ala Gly Glu Gly
                130                 135                 140

Leu Asn Val Ile Gln Gln Thr Thr Arg Tyr Phe Ser Thr Pro Gln Thr
145                 150                 155                 160

Met Asp Leu Phe Leu Asn Tyr Ser Met Asn Met Gln Pro Glu Asp Val
                165                 170                 175

```
Ala Ala Val Leu Leu Pro Val Leu Ala Ala Pro
            180                 185
```

```
<210> SEQ ID NO 25
<211> LENGTH: 192
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Gly Ser Ser His His His His His Ser Gly Leu Val Pro
1               5                   10                  15

Arg Gly Ser His Met Lys Lys Arg Lys Ser Val Asp Pro Ala Cys
                20                  25                  30

Pro Gln Ser Leu Pro Cys Phe Glu Ala Ser Asp Cys Lys Glu Ser Ser
            35                  40                  45

Pro Met Pro Val Ile Cys Gly Pro Glu Asn Tyr Pro Ser Leu Gln
50                  55                  60

Met Ser Ser Ala Glu Met Pro His Thr Glu Thr Val Ser Pro Leu Pro
65                  70                  75                  80

Ser Ser Met Asp Leu Leu Ile Gln Asp Ser Pro Asp Ser Ser Thr Ser
                85                  90                  95

Pro Lys Gly Lys Gln Pro Thr Ser Ala Glu Asn Ser Val Ala Lys Lys
            100                 105                 110

Glu Asp Lys Val Pro Val Lys Lys Gln Lys Thr Arg Thr Val Phe Ser
            115                 120                 125

Ser Thr Gln Leu Cys Val Leu Asn Asp Arg Phe Gln Arg Gln Lys Tyr
130                 135                 140

Leu Ser Leu Gln Gln Met Gln Glu Leu Ser Asn Ile Leu Asn Leu Ser
145                 150                 155                 160

Tyr Lys Gln Val Lys Thr Trp Phe Gln Asn Arg Met Lys Ser Lys
                165                 170                 175

Arg Trp Gln Lys Ala Ala Val Leu Leu Pro Val Leu Leu Ala Ala Pro
            180                 185                 190
```

```
<210> SEQ ID NO 26
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Gly Ser Ser His His His His His Ser Gly Leu Val Pro
1               5                   10                  15

Arg Gly Ser His Met Lys Lys Arg Lys Gln Lys Thr Arg Thr Val
                20                  25                  30

Phe Ser Ser Thr Gln Leu Cys Val Leu Asn Asp Arg Phe Gln Arg Gln
            35                  40                  45

Lys Tyr Leu Ser Leu Gln Gln Met Gln Glu Leu Ser Asn Ile Leu Asn
50                  55                  60

Leu Ser Tyr Lys Gln Val Lys Thr Trp Phe Gln Asn Gln Arg Met Lys
65                  70                  75                  80

Ser Lys Arg Trp Gln Lys Asn Asn Trp Pro Lys Asn Ser Asn Gly Val
                85                  90                  95

Thr Gln Lys Ala Ser Ala Pro Thr Tyr Pro Ser Leu Tyr Ser Ser Tyr
```

|  | 100 |  |  |  | 105 |  |  |  | 110 |  |  |
|---|---|---|---|---|---|---|---|---|---|---|---|
| His | Gln | Gly | Cys | Leu | Val | Asn | Pro | Thr | Gly | Asn | Leu | Pro | Met | Trp | Ser |
|  |  | 115 |  |  |  |  | 120 |  |  |  |  | 125 |  |  |  |

Asn Gln Thr Trp Asn Asn Ser Thr Trp Ser Gln Thr Gln Asn Ile
    130                 135                 140

Gln Ser Trp Ser Asn His Ser Trp Asn Thr Gln Thr Trp Cys Thr Gln
145                 150                 155                 160

Ser Trp Asn Asn Gln Ala Trp Asn Ser Pro Phe Tyr Asn Cys Gly Glu
                165                 170                 175

Glu Ser Leu Gln Ser Cys Met Gln Phe Gln Pro Asn Ser Pro Ala Ser
            180                 185                 190

Asp Leu Glu Ala Ala Leu Glu Ala Ala Gly Glu Gly Leu Asn Val Ile
        195                 200                 205

Gln Gln Thr Thr Arg Tyr Phe Ser Thr Pro Gln Thr Met Asp Leu Phe
    210                 215                 220

Leu Asn Tyr Ser Met Asn Met Gln Pro Glu Asp Val Ala Ala Val Leu
225                 230                 235                 240

Leu Pro Val Leu Leu Ala Ala Pro
                245

<210> SEQ ID NO 27
<211> LENGTH: 1158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

| atgggcagca | gccatcatca | tcatcatcac | agcagcggcc | tggtgccgcg | cggcagccat | 60 |
| atgaagaaga | gaggaaggc | gggacacctg | gcttcggatt | cgccttctc | gcccctcca | 120 |
| ggtggtggag | gtgatgggcc | aggggggccg | gagccgggct | gggttgatcc | tcggacctgg | 180 |
| ctaagcttcc | aaggccctcc | tggagggcca | ggaatcgggc | cggggggtgg | gccaggctct | 240 |
| gaggtgtggg | ggattccccc | atgccccccg | ccgtatgagt | tctgtggggg | gatggcgtac | 300 |
| tgtgggcccc | aggttggagt | ggggctagtg | ccccaaggcg | gcttggagac | ctctcagcct | 360 |
| gagggcgaag | caggagtcgg | ggtggagagc | aactccgatg | gggcctcccc | ggagccctgc | 420 |
| accgtcaccc | ctggtgccgt | gaagctggag | aaggagaagc | tggagcaaaa | cccggaggag | 480 |
| tcccaggaca | tcaaagctct | gcagaaagaa | ctcgagcaat | tgccaagct | cctgaagcag | 540 |
| aagaggatca | ccctgggata | tacacaggcc | gatgtggggc | tcaccctggg | ggttctattt | 600 |
| gggaaggtat | tcagccaaac | gaccatctgc | cgctttgagg | ctctgcagct | tagcttcaag | 660 |
| aacatgtgta | agctgcggcc | cttgctgcag | aagtgggtgg | aggaagctga | caacaatgaa | 720 |
| aatcttcagg | agatatgcaa | agcagaaacc | ctcgtgcagg | cccgaaagag | aaagcgaacc | 780 |
| agtatcgaga | accgagtgag | aggcaacctg | agaatttgt | tcctgcagtg | cccgaaaccc | 840 |
| acactgcagc | agatcagcca | catcgcccag | cagcttgggc | tcgagaagga | tgtggtccga | 900 |
| gtgtggttct | gtaaccggcg | ccagaagggc | aagcgatcaa | gcagcgacta | tgcacaacga | 960 |
| gaggattttg | aggctgctgg | gtctcctttc | tcagggggac | cagtgtcctt | cctctggcc | 1020 |
| ccagggccc | attttggtac | cccaggctat | gggagccctc | acttcactgc | actgtactcc | 1080 |
| tcggtcccctt | tccctgaggg | ggaagccttt | cccctgtct | ccgtcaccac | tctgggctct | 1140 |
| cccatgcatt | caaactga |  |  |  |  | 1158 |

<210> SEQ ID NO 28
<211> LENGTH: 1194
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

| | | | | | |
|---|---|---|---|---|---|
| atgggcagca | gccatcatca | tcatcatcac | agcagcggcc | tggtgccgcg | cggcagccat | 60 |
| atgaagaaga | agaggaaggc | agccgttctt | ctccctgttc | ttcttgccgc | acccgcggga | 120 |
| cacctggctt | cggatttcgc | cttctcgccc | cctccaggtg | gtggaggtga | tgggccaggg | 180 |
| gggccggagc | cgggctgggt | tgatcctcgg | acctggctaa | gcttccaagg | ccctcctgga | 240 |
| gggccaggaa | tcgggccggg | ggttgggcca | ggctctgagg | tgtggggat | ccccatgc | 300 |
| cccccgccgt | atgagttctg | tgggggatg | gcgtactgtg | gccccaggt | tggagtgggg | 360 |
| ctagtgcccc | aaggcggctt | ggagacctct | cagcctgagg | gcgaagcagg | agtcggggtg | 420 |
| gagagcaact | ccgatggggc | ctccccggag | ccctgcaccg | tcacccctgg | tgccgtgaag | 480 |
| ctggagaagg | agaagctgga | gcaaaacccg | gaggagtccc | aggacatcaa | agctctgcag | 540 |
| aaagaactcg | agcaatttgc | caagctcctg | aagcagaaga | ggatcaccct | gggatataca | 600 |
| caggccgatg | tggggctcac | cctgggggtt | ctatttggga | aggtattcag | ccaaacgacc | 660 |
| atctgccgct | ttgaggctct | gcagcttagc | ttcaagaaca | tgtgtaagct | gcggcccttg | 720 |
| ctgcagaagt | gggtggagga | agctgacaac | aatgaaaatc | ttcaggagat | atgcaaagca | 780 |
| gaaaccctcg | tgcaggcccg | aaagagaaag | cgaaccagta | tcgagaaccg | agtgagaggc | 840 |
| aacctggaga | atttgttcct | gcagtgcccg | aaacccacac | tgcagcagat | cagccacatc | 900 |
| gcccagcagc | ttgggctcga | aaggatgtg | gtccgagtgt | ggttctgtaa | ccggcgccag | 960 |
| aagggcaagc | gatcaagcag | cgactatgca | aacagagagg | attttgaggc | tgctgggtct | 1020 |
| cctttctcag | ggggaccagt | gtcctttcct | ctggccccag | gccccatttt | ggtaccccca | 1080 |
| ggctatggga | gccctcactt | cactgcactg | tactcctcgg | tcccttttccc | tgaggggaa | 1140 |
| gcctttcccc | ctgtctccgt | caccactctg | ggctctccca | tgcattcaaa | ctga | 1194 |

<210> SEQ ID NO 29
<211> LENGTH: 1194
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29

| | | | | | |
|---|---|---|---|---|---|
| atgggcagca | gccatcatca | tcatcatcac | agcagcggcc | tggtgccgcg | cggcagccat | 60 |
| atgaagaaga | agaggaaggc | gggacacctg | gcttcggatt | tcgccttctc | gccccctcca | 120 |
| ggtggtggag | gtgatgggcc | aggggggccg | gagccggct | gggttgatcc | tcggacctgg | 180 |
| ctaagcttcc | aaggccctcc | tggagggcca | ggaatcgggc | cggggttgg | gccaggctct | 240 |
| gaggtgtggg | ggattccccc | atgccccccg | ccgtatgagt | tctgtggggg | gatggcgtac | 300 |
| tgtgggcccc | aggttggagt | ggggctagtg | ccccaaggcg | gcttggagac | ctctcagcct | 360 |
| gagggcgaag | caggagtcgg | ggtggagagc | aactccgatg | gggcctcccc | ggagccctgc | 420 |
| accgtcaccc | ctggtgccgt | gaagctggag | aaggagaagc | tggagcaaaa | cccggaggag | 480 |
| tcccaggaca | tcaaagctct | gcagaaagaa | ctcgagcaat | ttgccaagct | cctgaagcag | 540 |

-continued

```
aagaggatca ccctgggata tacacaggcc gatgtggggc tcaccctggg ggttctattt    600
gggaaggtat tcagccaaac gaccatctgc cgctttgagg ctctgcagct tagcttcaag    660
aacatgtgta agctgcggcc cttgctgcag aagtgggtgg aggaagctga caacaatgaa    720
aatcttcagg agatatgcaa agcagaaacc ctcgtgcagg cccgaaagag aaagcgaacc    780
agtatcgaga accgagtgag aggcaacctg gagaatttgt tcctgcagtg cccgaaaccc    840
acactgcagc agatcagcca catcgcccag cagcttgggc tcgagaagga tgtggtccga    900
gtgtggttct gtaaccggcg ccagaagggc aagcgatcaa gcagcgacta tgcacaacga    960
gaggattttg aggctgctgg gtctcctttc tcagggggac cagtgtcctt tcctctggcc   1020
ccagggcccc attttggtac cccaggctat gggagccctc acttcactgc actgtactcc   1080
tcggtccctt tccctgaggg ggaagccttt cccctgtct ccgtcaccac tctgggctct    1140
cccatgcatt caaacgcagc cgttcttctc cctgttcttc ttgccgcacc ctga         1194
```

<210> SEQ ID NO 30
<211> LENGTH: 1230
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
atgggcagca gccatcatca tcatcatcac agcagcggcc tggtgccgcg cggcagccat     60
atgaagaaga gaggaaggc agccgttctt ctccctgttc ttcttgccgc acccgcggga    120
cacctggctt cggatttcgc cttctcgccc cctccaggtg gtggaggtga tgggccaggg    180
gggccggagc cgggctgggt tgatcctcgg acctggctaa gcttccaagg ccctcctgga    240
gggccaggaa tcgggccggg ggttgggcca ggctctgagg tgtgggggat tccccccatgc    300 ccccccgccgt atgagttctg tggggggatg gcgtactgtg ggcccaggt tggagtgggg    360 ctagtgcccc aaggcggctt ggagacctct cagcctgagg gcgaagcagg agtcggggtg    420
gagagcaact ccgatggggc ctccccggag ccctgcaccg tcaccctggg tgccgtgaag    480
ctggagaagg agaagctgga gcaaaaccccg gaggagtccc aggacatcaa agctctgcag    540
aaagaactcg agcaatttgc caagctcctg aagcagaaga ggatcaccct gggatataca    600
caggccgatg tgggctcac cctgggggtt ctatttggga aggtattcag ccaaacgacc    660
atctgccgct ttgaggctct gcagcttagc ttcaagaaca tgtgtaagct gcggcccttg    720
ctgcagaagt gggtggagga agctgacaac aatgaaaatc ttcaggagat atgcaaagca    780
gaaaccctcg tgcaggcccg aaagagaaag cgaaccagta tcgagaaccg agtgagaggc    840
aacctggaga atttgttcct gcagtgcccg aaacccacac tgcagcagat cagccacatc    900
gcccagcagc ttgggctcga aggatgtg tccgagtgt ggttctgtaa ccggcgccag    960
aagggcaagc gatcaagcag cgactatgca caacgagagg attttgaggc tgctgggtct   1020
cctttctcag ggggaccagt gtcctttcct ctggccccag ggcccatttt ggtaccccca   1080
ggctatggga gccctcactt cactgcactg tactcctcgg tccctttccc tgaggggaa    1140 gcctttcccc tgtctccgt caccactctg gctctccca tgcattcaaa cgcagccgtt    1200
cttctccctg ttcttcttgc cgcaccctga                                    1230
```

<210> SEQ ID NO 31
<211> LENGTH: 385
<212> TYPE: PRT
<213> ORGANISM: Artificial Sequence -continued

```
<220> FEATURE:
<223> OTHER INFORMATION: Description of Artificial Sequence: Synthetic
      polypeptide

<400> SEQUENCE: 31

Met Gly Ser Ser His His His His His His Ser Gly Leu Val Pro
1               5                   10                  15

Arg Gly Ser His Met Lys Lys Arg Lys Ala Gly His Leu Ala Ser
            20                  25                  30

Asp Phe Ala Phe Ser Pro Pro Gly Gly Gly Asp Gly Pro Gly
            35                  40                  45

Gly Pro Glu Pro Gly Trp Val Asp Pro Arg Thr Trp Leu Ser Phe Gln
50                  55                  60

Gly Pro Gly Gly Pro Gly Ile Gly Pro Gly Val Gly Pro Gly Ser
65                  70                  75                  80

Glu Val Trp Gly Ile Pro Pro Cys Pro Pro Tyr Glu Phe Cys Gly
                85                  90                  95

Gly Met Ala Tyr Cys Gly Pro Gln Val Gly Val Gly Leu Val Pro Gln
                100                 105                 110

Gly Gly Leu Glu Thr Ser Gln Pro Glu Gly Glu Ala Gly Val Gly Val
            115                 120                 125

Glu Ser Asn Ser Asp Gly Ala Ser Pro Glu Pro Cys Thr Val Thr Pro
130                 135                 140

Gly Ala Val Lys Leu Glu Lys Glu Lys Leu Glu Gln Asn Pro Glu Glu
145                 150                 155                 160

Ser Gln Asp Ile Lys Ala Leu Gln Lys Glu Leu Glu Gln Phe Ala Lys
                165                 170                 175

Leu Leu Lys Gln Lys Arg Ile Thr Leu Gly Tyr Thr Gln Ala Asp Val
            180                 185                 190

Gly Leu Thr Leu Gly Val Leu Phe Gly Lys Val Phe Ser Gln Thr Thr
            195                 200                 205

Ile Cys Arg Phe Glu Ala Leu Gln Leu Ser Phe Lys Asn Met Cys Lys
210                 215                 220

Leu Arg Pro Leu Leu Gln Lys Trp Val Glu Glu Ala Asp Asn Asn Glu
225                 230                 235                 240

Asn Leu Gln Glu Ile Cys Lys Ala Glu Thr Leu Val Gln Ala Arg Lys
                245                 250                 255

Arg Lys Arg Thr Ser Ile Glu Asn Arg Val Arg Gly Asn Leu Glu Asn
            260                 265                 270

Leu Phe Leu Gln Cys Pro Lys Pro Thr Leu Gln Gln Ile Ser His Ile
            275                 280                 285

Ala Gln Gln Leu Gly Leu Glu Lys Asp Val Val Arg Val Trp Phe Cys
290                 295                 300

Asn Arg Arg Gln Lys Gly Lys Arg Ser Ser Asp Tyr Ala Gln Arg
305                 310                 315                 320

Glu Asp Phe Glu Ala Ala Gly Ser Pro Phe Ser Gly Pro Val Ser
                325                 330                 335

Phe Pro Leu Ala Pro Gly Pro His Phe Gly Thr Pro Gly Tyr Gly Ser
            340                 345                 350

Pro His Phe Thr Ala Leu Tyr Ser Ser Val Pro Phe Pro Glu Gly Glu
            355                 360                 365

Ala Phe Pro Pro Val Ser Val Thr Thr Leu Gly Ser Pro Met His Ser
370                 375                 380

Asn
385
```

<210> SEQ ID NO 32
<211> LENGTH: 397
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

```
Met Gly Ser Ser His His His His His Ser Ser Gly Leu Val Pro
 1               5                  10                  15

Arg Gly Ser His Met Lys Lys Arg Lys Ala Ala Val Leu Leu Pro
             20                  25                  30

Val Leu Leu Ala Ala Pro Ala Gly His Leu Ala Ser Asp Phe Ala Phe
         35                  40                  45

Ser Pro Pro Pro Gly Gly Gly Asp Gly Pro Gly Gly Pro Glu Pro
     50                  55                  60

Gly Trp Val Asp Pro Arg Thr Trp Leu Ser Phe Gln Gly Pro Pro Gly
 65                  70                  75                  80

Gly Pro Gly Ile Gly Pro Gly Val Gly Pro Gly Ser Glu Val Trp Gly
                 85                  90                  95

Ile Pro Pro Cys Pro Pro Tyr Glu Phe Cys Gly Gly Met Ala Tyr
            100                 105                 110

Cys Gly Pro Gln Val Gly Val Gly Leu Val Pro Gln Gly Gly Leu Glu
            115                 120                 125

Thr Ser Gln Pro Glu Gly Glu Ala Gly Val Gly Val Glu Ser Asn Ser
        130                 135                 140

Asp Gly Ala Ser Pro Glu Pro Cys Thr Val Thr Pro Gly Ala Val Lys
145                 150                 155                 160

Leu Glu Lys Glu Lys Leu Glu Gln Asn Pro Glu Glu Ser Gln Asp Ile
                165                 170                 175

Lys Ala Leu Gln Lys Glu Leu Glu Gln Phe Ala Lys Leu Leu Lys Gln
            180                 185                 190

Lys Arg Ile Thr Leu Gly Tyr Thr Gln Ala Asp Val Gly Leu Thr Leu
        195                 200                 205

Gly Val Leu Phe Gly Lys Val Phe Ser Gln Thr Thr Ile Cys Arg Phe
    210                 215                 220

Glu Ala Leu Gln Leu Ser Phe Lys Asn Met Cys Lys Leu Arg Pro Leu
225                 230                 235                 240

Leu Gln Lys Trp Val Glu Glu Ala Asp Asn Asn Glu Asn Leu Gln Glu
                245                 250                 255

Ile Cys Lys Ala Glu Thr Leu Val Gln Ala Arg Lys Arg Lys Arg Thr
            260                 265                 270

Ser Ile Glu Asn Arg Val Arg Gly Asn Leu Glu Asn Leu Phe Leu Gln
        275                 280                 285

Cys Pro Lys Pro Thr Leu Gln Gln Ile Ser His Ile Ala Gln Gln Leu
    290                 295                 300

Gly Leu Glu Lys Asp Val Val Arg Val Trp Phe Cys Asn Arg Arg Gln
305                 310                 315                 320

Lys Gly Lys Arg Ser Ser Ser Asp Tyr Ala Gln Arg Glu Asp Phe Glu
                325                 330                 335

Ala Ala Gly Ser Pro Phe Ser Gly Gly Pro Val Ser Phe Pro Leu Ala
            340                 345                 350

Pro Gly Pro His Phe Gly Thr Pro Gly Tyr Gly Ser Pro His Phe Thr
        355                 360                 365
```

```
Ala Leu Tyr Ser Ser Val Pro Phe Pro Glu Gly Glu Ala Phe Pro Pro
    370                 375                 380

Val Ser Val Thr Thr Leu Gly Ser Pro Met His Ser Asn
385                 390                 395
```

<210> SEQ ID NO 33
<211> LENGTH: 397
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

```
Met Gly Ser Ser His His His His His His Ser Gly Leu Val Pro
1               5                   10                  15

Arg Gly Ser His Met Lys Lys Arg Lys Ala Gly His Leu Ala Ser
            20                  25                  30

Asp Phe Ala Phe Ser Pro Pro Gly Gly Gly Asp Gly Pro Gly
            35                  40                  45

Gly Pro Glu Pro Gly Trp Val Asp Pro Arg Thr Trp Leu Ser Phe Gln
50                  55                  60

Gly Pro Pro Gly Gly Pro Gly Ile Gly Pro Val Gly Pro Gly Ser
65                  70                  75                  80

Glu Val Trp Gly Ile Pro Pro Cys Pro Pro Tyr Glu Phe Cys
                85                  90                  95

Gly Met Ala Tyr Cys Gly Pro Gln Val Gly Val Gly Leu Val Pro Gln
            100                 105                 110

Gly Gly Leu Glu Thr Ser Gln Pro Glu Gly Glu Ala Gly Val Gly Val
            115                 120                 125

Glu Ser Asn Ser Asp Gly Ala Ser Pro Glu Pro Cys Thr Val Thr Pro
130                 135                 140

Gly Ala Val Lys Leu Glu Lys Glu Lys Leu Glu Gln Asn Pro Glu Glu
145                 150                 155                 160

Ser Gln Asp Ile Lys Ala Leu Gln Lys Glu Leu Glu Gln Phe Ala Lys
                165                 170                 175

Leu Leu Lys Gln Lys Arg Ile Thr Leu Gly Tyr Thr Gln Ala Asp Val
            180                 185                 190

Gly Leu Thr Leu Gly Val Leu Phe Gly Lys Val Phe Ser Gln Thr Thr
            195                 200                 205

Ile Cys Arg Phe Glu Ala Leu Gln Leu Ser Phe Lys Asn Met Cys Lys
210                 215                 220

Leu Arg Pro Leu Leu Gln Lys Trp Val Glu Glu Ala Asp Asn Asn Glu
225                 230                 235                 240

Asn Leu Gln Glu Ile Cys Lys Ala Glu Thr Leu Val Gln Ala Arg Lys
                245                 250                 255

Arg Lys Arg Thr Ser Ile Glu Asn Arg Val Arg Gly Asn Leu Glu Asn
            260                 265                 270

Leu Phe Leu Gln Cys Pro Lys Pro Thr Leu Gln Gln Ile Ser His Ile
            275                 280                 285

Ala Gln Gln Leu Gly Leu Glu Lys Asp Val Val Arg Val Trp Phe Cys
290                 295                 300

Asn Arg Arg Gln Lys Gly Lys Arg Ser Ser Asp Tyr Ala Gln Arg
305                 310                 315                 320

Glu Asp Phe Glu Ala Ala Gly Ser Pro Phe Ser Gly Gly Pro Val Ser
                325                 330                 335
```

```
Phe Pro Leu Ala Pro Gly Pro His Phe Gly Thr Pro Gly Tyr Gly Ser
            340                 345                 350

Pro His Phe Thr Ala Leu Tyr Ser Ser Val Pro Phe Pro Glu Gly Glu
            355                 360                 365

Ala Phe Pro Pro Val Ser Val Thr Thr Leu Gly Ser Pro Met His Ser
        370                 375                 380

Asn Ala Ala Val Leu Leu Pro Val Leu Leu Ala Ala Pro
385                 390                 395

<210> SEQ ID NO 34
<211> LENGTH: 409
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Gly Ser Ser His His His His Ser Ser Gly Leu Val Pro
1               5                   10                  15

Arg Gly Ser His Met Lys Lys Arg Lys Ala Ala Val Leu Pro
            20                  25                  30

Val Leu Leu Ala Ala Pro Ala Gly His Leu Ala Ser Asp Phe Ala Phe
            35                  40                  45

Ser Pro Pro Gly Gly Gly Asp Gly Pro Gly Gly Pro Glu Pro
        50                  55                  60

Gly Trp Val Asp Pro Arg Thr Trp Leu Ser Phe Gln Gly Pro Pro Gly
65                  70                  75                  80

Gly Pro Gly Ile Gly Pro Gly Val Gly Pro Gly Ser Glu Val Trp Gly
            85                  90                  95

Ile Pro Pro Cys Pro Pro Tyr Glu Phe Cys Gly Gly Met Ala Tyr
            100                 105                 110

Cys Gly Pro Gln Val Gly Val Gly Leu Val Pro Gln Gly Gly Leu Glu
        115                 120                 125

Thr Ser Gln Pro Glu Gly Glu Ala Gly Val Gly Val Glu Ser Asn Ser
    130                 135                 140

Asp Gly Ala Ser Pro Glu Pro Cys Thr Val Thr Pro Gly Ala Val Lys
145                 150                 155                 160

Leu Glu Lys Glu Lys Leu Glu Gln Asn Pro Glu Glu Ser Gln Asp Ile
                165                 170                 175

Lys Ala Leu Gln Lys Glu Leu Glu Gln Phe Ala Lys Leu Leu Lys Gln
            180                 185                 190

Lys Arg Ile Thr Leu Gly Tyr Thr Gln Ala Asp Val Gly Leu Thr Leu
        195                 200                 205

Gly Val Leu Phe Gly Lys Val Phe Ser Gln Thr Thr Ile Cys Arg Phe
    210                 215                 220

Glu Ala Leu Gln Leu Ser Phe Lys Asn Met Cys Lys Leu Arg Pro Leu
225                 230                 235                 240

Leu Gln Lys Trp Val Glu Glu Ala Asp Asn Asn Glu Asn Leu Gln Glu
                245                 250                 255

Ile Cys Lys Ala Glu Thr Leu Val Gln Ala Arg Lys Arg Lys Arg Thr
            260                 265                 270

Ser Ile Glu Asn Arg Val Arg Gly Asn Leu Glu Asn Leu Phe Leu Gln
        275                 280                 285

Cys Pro Lys Pro Thr Leu Gln Gln Ile Ser His Ile Ala Gln Gln Leu
    290                 295                 300
```

```
Gly Leu Glu Lys Asp Val Val Arg Val Trp Phe Cys Asn Arg Arg Gln
305                 310                 315                 320

Lys Gly Lys Arg Ser Ser Asp Tyr Ala Gln Arg Glu Asp Phe Glu
            325                 330                 335

Ala Ala Gly Ser Pro Phe Ser Gly Pro Val Ser Phe Pro Leu Ala
            340                 345                 350

Pro Gly Pro His Phe Gly Thr Pro Gly Tyr Gly Ser Pro His Phe Thr
        355                 360                 365

Ala Leu Tyr Ser Ser Val Pro Phe Pro Glu Gly Glu Ala Phe Pro Pro
    370                 375                 380

Val Ser Val Thr Thr Leu Gly Ser Pro Met His Ser Asn Ala Ala Val
385                 390                 395                 400

Leu Leu Pro Val Leu Leu Ala Ala Pro
                405
```

<210> SEQ ID NO 35
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ccgcatatga agaagaagag gaagagtgtg gatccagctt gtccc          45

<210> SEQ ID NO 36
<211> LENGTH: 84
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ccgcatatga agaagaagag gaaggcagcc gttcttctcc ctgttcttct tgccgcaccc    60
agtgtggatc cagcttgtcc ccaa                                          84

<210> SEQ ID NO 37
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ccgcatatga agaagaagag gaagcagaag accagaactg tgttctcttc c            51

<210> SEQ ID NO 38
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ccgcatatga agaagaagag gaagaacaac tggccgaaga atagcaatgg t            51

<210> SEQ ID NO 39
<211> LENGTH: 36
<212> TYPE: DNA

<213> ORGANISM: Artificial Sequence
<220> FEATURE:
<223> OTHER INFORMATION: Description of Artificial Sequence: Synthetic primer

<400> SEQUENCE: 39
ccgcatatgt cacacgtctt caggttgcat gttcat                            36

<210> SEQ ID NO 40
<211> LENGTH: 72
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
ccgcatatgt cagggtgcgg caagaagaac agggagaaga acggctgcca cgtcttcagg    60
ttgcatgttc at                                                       72

<210> SEQ ID NO 41
<211> LENGTH: 72
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
ccgcatatgt cagggtgcgg caagaagaac agggagaaga acggctgctt tctgccacct    60
cttagatttc at                                                       72

<210> SEQ ID NO 42
<211> LENGTH: 75
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
ccgcatatgt cagggtgcgg caagaagaac agggagaaga acggctgctt tcttgactgg    60
gaccttgtct tcctt                                                    75

<210> SEQ ID NO 43
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
ccgcatatga agaagaagag gaaggcggga cacctggctt cggat                   45

<210> SEQ ID NO 44
<211> LENGTH: 84
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
ccgcatatga agaagaagag gaaggcagcc gttcttctcc ctgttcttct tgccgcaccc    60

```
<210> SEQ ID NO 45
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ccgcatatgt cagtttgaat gcatgggaga gcccag                                  36

<210> SEQ ID NO 46
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ccgcatatgt cagggtgcgg caagaagaac agggagaaga acggctgcgt ttgaatgcat        60
gggagagccc ag                                                            72

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 47

His His His His His His
1               5
```